(12) United States Patent
Tolstorukov et al.

(10) Patent No.: US 11,555,194 B2
(45) Date of Patent: Jan. 17, 2023

(54) YEAST PROMOTORS FOR PROTEIN EXPRESSION

(71) Applicant: BIOGRAMMATICS, INC., Carlsbad, CA (US)

(72) Inventors: Ilya I. Tolstorukov, Claremont, CA (US); James M. Cregg, Claremont, CA (US); Thomas G. Chappell, San Marcos, CA (US); Knut R. Madden, Carlsbad, CA (US)

(73) Assignee: BIOGRAMMATICS, INC., Carlsbad, CA (US)

( * ) Notice: Subject to any disclaimer, the term of this patent is extended or adjusted under 35 U.S.C. 154(b) by 0 days.

(21) Appl. No.: 16/861,384

(22) Filed: Apr. 29, 2020

(65) Prior Publication Data
US 2021/0032643 A1 Feb. 4, 2021

Related U.S. Application Data

(63) Continuation of application No. 14/773,482, filed as application No. PCT/US2014/022086 on Mar. 7, 2014, now Pat. No. 10,676,750.

(60) Provisional application No. 61/775,029, filed on Mar. 8, 2013.

(51) Int. Cl.
| | |
|---|---|
| *C12N 15/81* | (2006.01) |
| *C07K 14/39* | (2006.01) |
| *C12P 21/02* | (2006.01) |
| *C12N 9/40* | (2006.01) |

(52) U.S. Cl.
CPC ............ *C12N 15/815* (2013.01); *C07K 14/39* (2013.01); *C12N 9/2465* (2013.01); *C12P 21/02* (2013.01); *C12N 2800/60* (2013.01); *C12Y 302/01022* (2013.01)

(58) Field of Classification Search
None
See application file for complete search history.

(56) References Cited

U.S. PATENT DOCUMENTS

2022/0025387 A1* 1/2022 Achmüller .............. C12P 21/02

FOREIGN PATENT DOCUMENTS

WO WO-2012129036 A2 * 9/2012 .............. C12P 21/00

OTHER PUBLICATIONS

Li et al., Expression of Recombinant Proteins in Pichia Pastoris, Appl. Biochem. Biotechnol. 142, 2007, 1045-24. (Year: 2007).*
Wu et al., Combined use of GAP and AOX1 promoter to enhance the expression of human granulocyte-macrophage colony-stimulating factor in Pichia pastoris, Enz. Microbial. Technol. 33, 2003, 453-59. (Year: 2003).*
Duan et al., Both the AOX1 promoter and the FLD1 promoter work together in a Pichia pastoris expression vector, World . Microbiol . Biotechnol. 25, 2009, 1779-83. (Year: 2009).*

* cited by examiner

*Primary Examiner* — Robert B Mondesi
*Assistant Examiner* — Todd M Epstein
(74) *Attorney, Agent, or Firm* — Barnes & Thornburg LLP

(57) ABSTRACT

Isolated nucleic acids, expression methods, host cells, expression vectors, and DNA constructs for producing proteins, and proteins produced using the expression methods are disclosed. More specifically, nucleic acids isolated from *Pichia pastons* having promoter activity and expression methods, host cells, expression vectors, and DNA constructs of using the *Pichia pastons* promoters to produce different proteins and polypeptides are disclosed.

20 Claims, 20 Drawing Sheets

Specification includes a Sequence Listing.

METHANOL-INDUCIBLE PROMOTER SEQUENCE
CAM1_(FR839630_178837..180488)_SELECTION (SEQ ID NO: 1)

ATTGTTGTGAATACTCTCCTTCATTTGGATTTCTTGGACTTCGGACTCTCTTGATCTC
TCTTCGAAAGTTTTAACTCTGTTCATGTATAATTTTACCCGCTGTAGGTCGCTCATA
ATACCATGAGTATGCACATCTTTTACTCCATTAACTTTCAGGTATGCAAAATACAAT
GAAGATAGTATATAGCTCAAAGAATTTAGCATTTTGCATTGATCTAATTGTGACATT
TTCTCTATGATATCATCTAGCTTCTTAAACTCGAGAATCTCGTCCAACGAGGCAGAA
ACATTGTCCAGTCTTACGTCAAGATTATTCACGAGTTTCTGGACCGTATCAACGTTT
TCCATCTTAAGATTACAGTAAGTATCGTCCTTTTGAACTGCAAAGGTAGAAAAGTT
AATTTTTGATTTGGTAGTACACTATGAAACTTGCTCACCCCAATCTTTCCTCCTGAC
AGGTTGATCTTTATCCCTCTACTAAATTGCCCCAAGTGTATCAAGTAGACTAGATCT
CGCGAAAGAACAGCCTAATAAACTCCGAAGCATGATGGCCTCTATCCGGAAAACG
TTAAGAGATGTGGCAACAGGAGGGCACATAGAATTTTTAAAGACGCTGAAGAATG
CTATCATAGTCCGTAAAATGTGATAGTACTTTGTTTAGTGCGTACGCCACTTATTC
GGGGCCAATAGCTAAACCCAGGTTTGCTGGCAGCAAATTCAACTGTAGATTGAATC
TCTCTAACAATAATGGTGTTCAATCCCCTGGCTGGTCACGGGGAGGACTATCTTGC
GTGATCCGCTTGGAAAATGTTGTGTATCCCTTTCTCAATTGCGGAAAGCATCTGCTA
CTTCCCATAGGCACCAGTTACCCAATTGATATTCCAAAAAGATTACCATATGTTC
ATCTAGAAGTATAAATACAAGTGGACATTCAATGAATATTTCATTCAATTAGTCAT
TGACACTTTCATCAACTTACTACGTCTTATTCAACAAT

FIG. 1

METHANOL-INDUCIBLE PROMOTER SEQUENCE
PP7435_CHR1-1351_SELECTION (SEQ ID NO: 2)

GTCAACTGCGTACTCTTTTGTCGAATGGACTACTGAATCTGCCTCGATAGCCACTAT
AGGAAGGTCCATAGAGGCCAGTTTTTCAACTAGTCTTGGTGGAAAGAAACCGACA
AAGCCTTTCATGGAGTCACCGATACTGAAAGGTTCAAACAAAGAATGCTTGGGTAG
TCTCTTAATACCCATGGCAACGAAAAGGGGTCTTCATTGTTCAACATGAATTCGT
ATCCACCTTTAATGTAGTCATAAAGCTGCTGAAGTTCCGAATCAGTGATGGAACTG
TCTACAGTGACAATATAGGAGTTCTCAATCACCTTATATCCAGTCGAATATATCTGG
ATAGGGTCGGGTCTCACTGTGGAAGATTCAAATGGGTTAGATCCCTGTAATTTCAG
CGATGGAGACTCAGTATGATGGGCAAGGAAAACGGCAATTGGATATTCAATTGG
TCAAGAGATGGTATCAAAAGCGAGTGTGCCAGGGTAGCCACGGTAGCCACTGATG
CTAATCTGATAATTTTCATTTCTGGAGTGTCAAAACAGTAGTGATAAAAGGCTATG
AAGGAGGTTGTCTAGGGGCTCGCGGAGGAAAGTGATTCAAACAGACCTGCCAAAA
AGAGAAAAAGAGGGAATCCCTGTTCTTTCCAATGGAAATGACGTAACTTTAACTT
GAAAAATACCCCAACCAGAAGGGTTCAAACTCAACAAGGATTGCGTAATTCCTAC
AAGTAGCTTAGAGCTGGGGGAGAGACAACTGAAGGCAGCTTAACGATAACGCGGG
GGGATTGGTGCACGACTCGAAAGGAGGTATCTTAGTCTTGTAACCTCTTTTTTCCAG
AGGCTATTCAAGATTCATAGGCGATATCGATGTGGAGAAGGGTGAACAATATAAA
AGGCTGGAGAGATGTCAATGAAGCAGCTGGATAGATTTCAAATTTTCTAGATTTCA
GAGTAATCGCACAAAACGAAGGAATCCCACCAAGCAAAAAAAAAAATCTAA

FIG. 2

METHANOL-INDUCIBLE PROMOTER SEQUENCE
TH14_SELECTION (SEQ ID NO: 3)

TGCTGTTTTGGGCTCGTACGGATGTTTCTTAGGTCCGATGATTGGTGTTATGACTTG
TGACTACTACTTCGTACGTCATCAGAAACTCAAGCTGACAGACCTCTACAAAGCCG
ACAAGAGTTCTATTTACTGGTTCTACAAAGGATTCAACTGGAGAGGTTTCGTTGCCT
GGATTTGCGGTTTTACTCCAGGTATTACAGGGTTTCCTAGCGTCAACCCCAACTTGA
CTGGGGTTCCTACAGCCTGTATCAAGATGTTCTACATTTCGTTTATCATTGGTTACC
CGATCGGATTCTTAGTTCATCTGGCACTCAATAAGCTATTCCCTCCACCAGGTCTTG
GTGAAGTCGATGAGTATGACTACTACCACTCTTTCACCGAAAAGGAAGCACTGAAA
TTAGGAATGGCCCCTAGTTCCGAGTTGGACAGAGTCAGCACCGATGACCCGATCAA
TATTCCTTACGACGAGAAGTCTTTAGGCTAATGTAGTTAAATAGTTAATCGAAACA
ATCGTGTATCCTCTTTATCGTACCAGCGGGATTCGCTGCTTGGATGGGTGACTCCTG
TCCAGTTGACTCAAAGTAGTCAAAATAGGCCTGGAGACCCTTAACAGGTCGATGAG
TAGCCTACTATGAGAAAACCCCTCACCACAACTGGACTATAAAGGGCACGTCAAT
CCCCAAAGCAACTCTTTTCTTTCATCCCTACTTTATTACTTTATCCTTTGATCTTCAT
TGAAGAAAATCTGAAACAATTGTAAGCAGCAATCCACACCTCCCCAGCAATGACTC
AATTTACTAACCCCATTGACAGAAATGTGAGCATCTTTTTAGATGTCATGATGAT
AGGTGGAGTATTCTTAATTATTGCTTTCAGCAAACCGGTGCCCATAAAGTGTTTCCC
ATTAAATCAATGAGAGGCATTAAGGCTGAGATTAAACGGTTGAACTTGAACTAGAT
AATTCTAGCGGAAAGAATTGCTCTTTTATTACGTCGT

FIG. 3

METHANOL-INDUCIBLE PROMOTER SEQUENCE
GPM2_SELECTION (SEQ ID NO: 4)

AGGCTCTGCGCAAGGCAACTGAGAAATTGAATAGTGGTTTCAAGCCCGCTGACTTT
TTGTATTATCTCAATGTCGGTGTTTCACAGTCCCCAGAAGGGGGCTTTGCCTTCAAG
GGAGACGGAAGAGACATCGTCAACCCTGGGGAGAAGTATTTCAAATGGCGCAAGT
TCGCTAATTTTTACGATTAAGCAGTGCTGTATGGGGTAGTTAATAAATCGGGAATA
TCCTTCTGACGTGACTGTAACAAATCTCTTTTACGTGGTGCGCATACTGGACAGAG
GCAGAGTCTCAATTTCTTCTTTTGAGACAGGCTACTACAGCCTGTGATTCCTCTTGG
TACTTGGATTTGCTTTTATCTGGCTCCGTTGGGAACTGTGCCTGGGTTTTGAAGTAT
CTTGTGGATGTGTTTCTAACACTTTTTCAATCTTCTTGGAGTGAGAATGCAGGACTT
TGAACATCGTCTAGCTCGTTGGTAGGTGAACCGTTTTACCTTGCATGTGGTTAGGAG
TTTTCTGGAGTAACCAAGACCGTCTTATCATCGCCGTAAAATCGCTCTTACTGTCGC
TAATAATCCCGCTGGAAGAGAAGTTCGAACAGAAGTAGCACGCAAAGCTCTTGTC
AAATGAGAATTGTTAATCGTTTGACAGGTCACACTCGTGGGCTATGTACGATCAAC
TTGCCGGCTGTTGCTGGAGAGATGACACCAGTTGTGGCATGGCCAATTGGTATTCA
GCCGTACCACTGTATGGAAAATGAGATTATCTTGTTCTTGATCTAGTTTCTTGCCAT
TTTAGAGTTGCCACATTCGTAGGTTTCAGTACCAATAATGGTAACTTCCAAACTTCC
AACGCAGATACCAGAGATCTGCCGATCCTTCCCCAACAATAGGAGCTTACTACGCC
ATACATATAGCCTATCTATTTTCACTTTCGCGTGGGTGCTTCTATATAAACGGTTCC
CCATCTTCCGTTTCATACTACTTGAATTTTAAGCACTAAA

FIG. 4

METHANOL-INDUCIBLE PROMOTER SEQUENCE
PP7435_CHR2-0790_SELECTION (SEQ ID NO: 5)

CAAACTTAACCGACCGTTCTTCCATCCGTTTATTAATATACACACCTATGAACTGAG
CCAGGTTTTCAGGTCTCTGTGACTCTCTATACATTGACGGAACAACATCCGTTCAGT
CTCATCCAATTGCAGCCCAAACTCTGAGTTTAGCAATTGCAAATGGTTATTATCTGA
CGAGTAATCGTTGATGGCACATGCCCTCTGTTTGAACATCTCTTGAACAATAGCCAT
CAGTTCTGTGTCATTAAACATGCTTCCCCATTTCACTGACAGTTTGTAGAAATAGGG
CAACAATTGATGCAAATCGATTTTCAACGCATTGGTTTTGATAGCATTGATGATCTT
GGAGCTGTAAAAGTCCGGCTGGATAAGCTCAATGAAATAGGTTGGTTGATCTGGAT
CTTCTTTTGGGTCATTTGTTCGCTCTGTATTTCACAAATTGCCAGAATCTCTGCCAA
CCACAGTGGTAGGTCCAACTTGGTGTTCTGAATCACAGGCTTCCCCGGGTTGTTCTC
TAAATAACCGAGGCCCGGCACAGAAATCGTAAACCGACACGGTATCTTTTGTCCGT
CCGCCAGTATCTCATCAAGGTCGTAGTAGCCCATGATGAGTATCAAAGGGGATTTG
GTTATGCGATGCAACGAGAGATTGTTTATCCCAGATGCTGATGTAAAAACCTTAAC
CAGCGTGACAGTAGAAATAAGACACGTTAAAATTACCCGCGCTTCCCTAACAATTG
GCTCTGCCTTTCGGCAAGTTTCTAACTGCCCTCCCTCTCACATGCACCACGAACTT
ACCGTTCGCTCCTAGCAGAACCACCCCAAAGTTTAATCAGGACCGCATTTTAGCCT
ATTGCTGTAGAACCCCACAACATAACCTGGTCCAGAGCCAGCCCTTTATATATGGT
AAATCCCGTTTGAACTTCGAAGTGGAATCGGAATTTTTACATCAAAGAAACTGATA
CTGAAACTTTTGGCTTCGACTTGGACTTTCTCTTAATC

FIG. 5

METHANOL-INDUCIBLE PROMOTER SEQUENCE
PP7435_CHR3-0842_SELECTION (SEQ ID NO: 6)

GTAAATAAGTTAAAGTTTAAAAAGGAAAGGATGCAAAAAATATCCTTGAAGGCAA
CGAATATTTTGAAATCCCCGATGCCAAATAAATGCTATCACTTAAAGAGCACAATA
GAGGTGGAAAAAGAAAAACTTGGTCAAGCTAAGGGTTAGCAAGTTTCTGTTTGTGA
TAATCAGGGAGAAGGTGTCAGAAAAAACATGATTATGTAAGTGGTGTTAGGAGCC
GTTAAAGCATTCTGTCGGCCAATAGCAAGCCCGCCTTTTGTCATCTTTTTGCGGTTT
CTCTGTGTGAGACACTAATCACCTTTGTAAGACATCGGGAAAACCGTTGCGCAAAA
TGAGATAGAGATTGTTCTCGATAGAGGAGCGTAGTAGCCTCTCCAGCCTGCTTTAG
CAACATAATAGAAAAGAAATATGCGTTGCCTAGGGAGGCTACGTATGCCCAGCAT
AAACGAGTGTTTACCTTACTTCGCACGAGCAGTAGCCACTAAGATCATTATAAACT
CACCTATTGTCTTCATGCTGTGCTCCGCGTATTTGTCTGTTCAGGGTGTCATTTCTCG
TCATGAGAATCTGATTGATGACTATGCGAGATTACCCCTGGATTTTTTTGATCCCG
TAACGCGAACTTGAACATTGACTTTGATATGGCAATGGGCCCTAATATGCCCTAAT
ATGCCCTAAGCTTAACAATTGACTTCTGTTCTCTGGCAGACTCCACAGAAACTGG
TTGACAGGTCTAATTTCTTTTTGAATCATTTCCGGTGATTCATTTGATGCTTAGAGT
GAGTCATGGGTTCTTTATCCGCATTCTTCTTCGCGTCTGCTGTGCTTAATAATAGCC
TACTAAAAATGTGGGGAGCCTCTTACCTTATGTCTATAAAACAAGCACATGACTA
TGCCATCGCCTTCATAGTTGTTCTGCGGGTTTTTGCTTGTTTATGACCGTAGAGAC
CAACCAATTTACATATCTACAGGGTAGCACATTCGATAAGAAA

FIG. 6

CONSTITUTIVE PROMOTER SEQUENCE
PP7435_CHR1-0269_SELECTION (SEQ ID NO: 7)

GAAGGGCTACAGGTTGTTCGAGTCAACCAAGAAAAAAATGTCTCCATTCCATTACC
TTCAGAAGTCTGTGATGTGAGATTCAGTAGCAACGAAACTACACCCATAGTCAGAC
CAAATGAAACCAGTCAAGACTTTTCAATCTGGCTCAAAGACCAGCCAGGAATCAG
AGAGTTTTTACAAAATTCGACCATCGCACTTGGATCTAGACTCAATCTCTTAAGCA
ATGTAAATATTGAGATACATGGGGAGACAGTGAATTATACCTTCACAGAAATCGAA
CAGAGGAGACAATTAGAACTGAATTACAGACAACACCTTCTTCAATATTCAGCAGT
GGAAGGAGGACTACTGGGTGGGAAAAGAACAGAAGTCAATCTGGTAAATATGGCT
GAAGCCCCTGCAACTACAGAGTCATTTGCCAAGTTTTCCAAGGACGTTCTGGATCT
TGTTCGTATACTAAGTTGTACATAGAGTGAATATAAGAACAGGGGCCCAGTTAAGA
CTAGATCTATCAATACTGTAATCTAGACTGAATAAACCTGAATGGCAAAGAAACAC
CAAATGGAGATTTCCGAGGTAGTATCGACCGCACTTACGAGGGCGGATATGTGTCC
TCCTGATGTATAGTTACGTCATAAAGTATTGATGCCTAGACCATTTCAATTTCGTAG
TCATCTATTCGTGAAAAGAGGCAAGGCTGATTGTTCAATTTGGCAATGATGAGCCA
ACAGTGCTTAAAACTGGACAAAACTTAGATCAAATATTCACCGTTGTAAAACACAG
TTCCTCTCGTCTTCATTTTAGCCCATTTGCACAAAACCCCAACTTTTACATTCCGGA
AAAAAAATGCTCCTCCACCTAGATGCAGAGTGTACCGCTCAAAGAACCCTCGATGA
GTTTCGACCATCTTCACCAAGTGAAATAATATTTATAGTGAGGGAAAGAACATTTT
TTTCCCTGTTCGTTTCTTTACCAGTTAACTACTACAGAATCTTCTAAA

FIG. 7

CONSTITUTIVE PROMOTER SEQUENCE
PP7435_CHR2-0207_SELECTION (SEQ ID NO: 8)

TGGATCTGGATGTAGATGCAACTGCCCGAAAAAATACAAAGAATTAGAAGATAGT
CCCAGCTGCTGTATTGGCAGATGGATGGTATTAACTAACGATAAGTATAAAGGCGA
AAAATACCTAGATAAATACTCAATGGCCGAAGAGGTCAAGCAGACTCTAAGCAAG
GGTGAAAAACTAAACGTTAAAGAGATATTGAAGAGGCACCACAAGTATCCAACAT
GAGAAGAGAACCCAGAAAGAGTCAAAATACAAACTCGAAAACATACCGATTGGCA
GAATACCAGCCATACATTACATTTGATACTAATATACATAAAATACACTAACCTCC
GAAACCATACAAGGTACGTCCTTGTCTTTTCAAAGCGTAGACGACATCCAGAGAAG
TAACAGTCTTTCTCTTGGCATGCTCAGTGTAAGTAACAGCATCTCTAATGACGTTCT
CTAAGAAAGTCTTCAGCACAGCTCTGACTTCTTCGTAGATCAAAGCGGAAATACGC
TTAACACCACCTCTTCTGGCCAATCTTCTGATAGCTGGCTTTGTGATACCTTGAATG
TTGTCTCTAAGAATCTTTCTGTGACGCTTAGCACCGGATTTTCCTAGACCTTTTCCA
CCTTTTCCTCTACCAGACATATTTATTGATTATTTGTTTATGGGTGAGTCTAGAAAA
GGACGCACTCGTCTTGTATTTATAGATGAAAGAGTTAAGGTGGACAATGCAGTGC
CAAACCGTAATGTTGATACGACACGGTACGCGATGAACTGAGCCGTACTCCAGAG
GCAGAGCGTGCGTAAATTTGAAACTGTAAGAACATGTCCCATTTCTATGCTACCAG
AACTCATAATAAACTTGCATCCCATTTCAGTCGGGAGTGTCGCAGTGCGAAATACT
GTTGGCACTGATGGCAAAAAGTGCCAAATCGTTATCTATGGGAGACTCTTATAAAT
ATCCAGATCCTCCCCCTCCTGCTTCTTCTTGTGTCTATCGTAGTAAAA

FIG. 8

CONSTITUTIVE PROMOTER SEQUENCE
PP7435_CHR2-0208_SELECTION (SEQ ID NO: 9)

GATCGAGGACATGGTGTTTTTTTTTTATAGAAGTATCATACTAAGTGTACTTTTC
ACTTGCTTATCCTCTTTTCTACCTCACCCTCATAAGCAGGAAATTCTTGACAATCGC
AAGAGTAAGCGTGCACTACACAGCCATCGGCAACACCGAATTTCACCTTACAGCCA
GTTTGTATCTCCCTTAAATATCGTATTCGATTAATATACACTACATTACACTTAGGA
TCTTTCACCTCTCAGTCTTCTAGCTAACAGGATATCCTTCTTTTGGATAGTAACTCTC
TTAGCGTGAATAGCACACAAGTTAGTATCTTCGAACAAGGAAACCAAGTAAGCTTC
GACGGATTCTTGCAAAGCACCGATGGCAGAAGATTGGAATCTCAGGTCAGTCTTGA
AGTCCTGAGCAATTTCTCTGACCAATCTTTGGAAAGGCAGCTTTCTGATAAGCAAC
TCAGTAGACTTTTGGAATCTTCTGATTTCTCTCAGAGCAACGGTACCTGGCTTATAT
CTGTGGGGCTTCTTGACACCTCCAGCAGCAGATGGAGCGGATTTTCTGGCAGCCTT
GGAAGCCAATTGCTTTCTTGGGGCTTTACCACCAGTGGATTTTCTTGCTGTTTGTTT
AGTTCTAGCCATTTTTACTACGATAGACACAAGAAGAAGCAGGAGGGGGAGGATC
TGGATATTTATAAGAGTCTCCCATAGATAACGATTTGGCACTTTTGCCATCAGTGC
CAACAGTATTTCGCACTGCGACACTCCCGACTGAAATGGGATGCAAGTTTATTATG
AGTTCTGGTAGCATAGAAATGGGACATGTTCTTACAGTTTCAAATTTACGCACGCT
CTGCCTCTAGGAGTACGGCTCAGTTCATCGCGTACCGTGTCGTATCAACATTACGGT
TTGGCACTGCATTGTCCACCTTAACTCTTTTCATCTATAAATACAAGACGAGTGCGT
CCTTTTCTAGACTCACCCATAAACAAATAATCAATAAAT

FIG. 9

CONSTITUTIVE PROMOTER SEQUENCE
PP7435_CHR2-0809_SELECTION (SEQ ID NO: 10)

TTCCATATTACTTCAGCAAATACAAGTACAAATCACTTGACTCGTATCAGTTCTTGG
ATACCCTTTATGAGTTTTTCTCAGATAAACATGAAATTTTAGACAAAGTTGACTGGG
AAACTTGGTTGTACAAGTTTGGATTACCACCAAAGCCAAAGTTTGATACCTCGCTA
GTTGATGAATGCTATGATTTAGCTGCCAAATGGGTTGATGTCACCAAGAAGGATAG
CAAAGATCTTTTGAAGAAAACTTTCAGCTCAGATGATATTTCTAATTTCACGGGTA
ACCAAACTAACGTCTTCCTTGATACTTTAGTATCTTATCAAGGAGTGGAAGGTTTCC
TGTGGAATTCCAAAGAAGGGGAACAAGCTTTGACGTTTATGAGAGAGCTATAG
CGTTTATGACGACTCCAAGAATGCAGAAGTCATTTTCCGCTGGTACAGACTACAAT
TAACAGGGAGAAGCAAGCAGTACTACCAGCGTCTGGCCGATTGGCTGGGAACAAT
CGGACGAATGAAATTTGTTCGACCATCTTATCGAATGCTAACGATGTGGACCCTC
AACTGGCCAAGGACACATTCTTGAAGTTTGAGCCAATCTACCATCCGATCTGTCGA
TCAATGATCCGCAAGGACTTACACTTGTAGAGAAAAAGGTATGTGGGGTATACGT
AAGTACGTTAAGTATGCCAAAAACATCACAATAGACAATACGCCCTACAACAGAA
CGTCAAGTTGTACGCGAGCACCGTTAAATCACACGTAACATCCAACACCTTTCTTT
GGTAGGGCATAGCCCCAGGTGGCACCACGTGCATAAACCATTTTACACCCCAACAC
CCACCAATCCTCGCCCTCTGGCATTTGCTCAAATTTTTTAACCAGCTTCTGATTACA
TAGGTAACCAGTTCAATTCATAGGTAAGTCAACGCCGAACAACAAGGGAAATCAC
CCATCCGCTCACATCAGTCCAGTTGAAGACTAACATTAAAAGACAAAA

FIG. 10

CONSTITUTIVE PROMOTER SEQUENCE
PP7435_CHR4-0069_SELECTION (SEQ ID NO: 11)

TGGTAATCAACTCACTATTTCATTCATGTCAACAGCCCCGAAAACGATAATTAATA
GACAACCCCAATCATATTTAGTGAGTTTTCGGATTAAAGCTTGTTCGCGTTCCGGTT
GATGATGGTTTCAAGAAAATGCTGAGCTCGCTCTTATACTGGGTCCCTTGAAATGA
TATGCATATGTTGGGAATACGCTAATGTACTTTGACAGATATTGCTTCTCCTTGTAG
CAAATTGACAGTTTCGTTTGCAACTGTAACACTTGGTGATCGATATTTGGATAAAC
ACAATTACTATTTTGGAGTTACAACCAGAATTCGTCTTAATGTTTCGCATCCTTGTT
CAAAGACTAAAACTTCTTCGATTTCGAATTTGTCTTAAGTATTGACTAGTCGGGCTC
AAAGAGCAACACTAGCTGGAAACGGCTCAGGATCACTTTCGTTTTTTTTCTAGAAA
ATGAGGCAATTGTAGGACTGGGTCTCTTTATCTGCAATTTGTGTAAGCTGGTTTACT
GTTCTCAACAAAATAGAAGTGAACCGTCCGTGATGTAAAATGAGACTACTCCGTTG
AATCGCAACAAGTATTATATCCTAGCTTAAGGTGATTCTTAACTTTGGAGCAAAAA
TATCGTGTAACAACGCCGGCTCAGTCAATCTTCTTTGAATTAACACTGCACCTCTAT
CTTGAACACTATCTACATGAGTGTGCAACCAGAAAGAATGCAAAGATTAATTTTCT
TACCCACAATGTGGTCCGATCCACAATTCTAGTGAATTCCTAACATGTTTAGTACCA
ACGTTTGAACAACAGATACATCACATTGAAAAAAAGGATTGAGAATAATAATCAA
ATTTTCAGCATTATATAGTACCACGAAACTAAATCGCTTTGGAAGGAGAAACATTT
TCAAGCTGTTAAACTGGATTTATCCAAAATAGTTAGTTTGCACAAGTTTAAAAGGA
GGTGTCTAACAGGTGGGGAAAAATCAGTTAATTGAGTTTTA

FIG. 11

CONSTITUTIVE PROMOTER SEQUENCE
PP7435_CHR4-0800_SELECTION (SEQ ID NO: 12)

CAGGGGGCAGTTACTTCATTATATGTAGTAAGTTGTCTAATAACACTTTAGAATTG
AGGGTTGTACTAACCAAACAGACACTGTTGCAAGTTATGGTGACAAGGTTGCTTTC
AAGCCCTGATACTAAAGTGGTTCATATTTGCATGAGTGGTTCGTATCCGGAGGATC
ATCTACAGAACGTGCTAAAATCATTATCTTTTGGTGACGAAAAAAAGAAGTTACCA
TTGGATGACAAGACAAAGAATACTATTTTAGATAGTATTTGGCTGGCTTACCCTGA
CGATCTGAATGAGTCGTACGAACAATTGGAGAAACTTCAAGAAGAGAATTCAGCG
GGTCTCTCAAAACTGATGATTGTTATTCAAGATTTGGATGATATGGCTGAGTTATAC
GCCTTCAGAGATTTCACATCAGGTAAGTTTACACTCTGAAATTTTGATTACAAAATA
TATACTAACACATTTAGCCTGTGCTACATTGATGAATTTCATGCTTAAATTAAGAAA
AATCAGTCAACTGGGAGCTACGGTCATAGTTACTAATATCAATCATGACTCTGGAG
TGTCTATGATATTCTCCTACATAGCCAAGTTTTACGACAATAAACTAACGTTCAGCT
TTCACAAAGGCTCAATACTTTTAGAGATACGTCCTCTAACGATATCAACCGAACTT
CAGCTCAGCACTACTACACTCTCTATCAACCCACAAACGATGTACCACATGCTTTTC
CCCAGCTCTGAAAATGCCCTTATCAGCACGTGATTAAAGATGAGGGCTCGCTGACA
AGATGTGACTAGACTGCCACCTTTACACCCTCAGAGAAGACAAACGTCTCATTTCG
CGGTTAGTAAGGTTAACCCACAAATTTTCAACGTGTACTACCCAAGAGCTCTCTGT
CTGCCATGGGCGCGCGCACACTCCCTGGTGTGCGAATCCAACCAAAGTATGAAAAA
AAAAAACCATTACTTCAAAGTTTTCTTTCAACACACAAAAGAAG

FIG. 12

CONSTITUTIVE PROMOTER SEQUENCE
TEF2_SELECTION PICHIA PASTORIS CBS 7435 CHROMOSOME 1,
COMPLETE REPLICON SEQUENCE (SEQ ID NO: 13)

GTATTTGACAGGTTGGGGAGCAAATAAGTGATGATGTCCCATGAAAGTAGAAAAT
GGCTAGTAGAAGGCAAAAATTTGAAATTCTTAGAGTCAAATAGTTAGACTCCAAGT
TCTAATCCACATTTGGTCAGTTTCATAGCATCCAGAGCTTTTGCCACTGGTGAACAT
ATCTACCCATTGCGATGCAACAAGTCACTGAAAGCCTAAAACGGAGATTCCCCTAT
CTTACAGCCTCGTTCAAAAAAACTGCTACCGTTTATCTGCTATGGCCGATGTGAGG
ATGCGCTCATGCCCAAGAGTCCAACTTTATCAAAAACTTGACCCGTCATACAGGCT
CTAGATCAAGAAGCAAACTTAATCTCAGCATCTGGTTACGTAACTCTGGCAACCAG
TAACACGCTTAAGGTTTGGAACAACACTAAACTACCTTGCGGTACTACCATTGACA
CTACACATCCTTAATTCCAATCCTGTCTGGCCTCCTTCACCTTTTAACCATCTTGCCC
ATTCCAACTCGTGTCAGATTGCGTATCAAGTGAAAAAAAAAAAATTTTAAATCTTT
AACCCAATCAGGTAATAACTGTCGCCTCTTTTATCTGCCGCACTGCATGAGGTGTCC
CCTTAGTGGGAAAGAGTACTGAGCCAACCCTGGAGGACAGCAAGGGAAAAATACC
TACAACTTGCTTCATAATGGTCGTAAAACAATCCTTGTCGGATATAAGTGTTGTA
GACTGTCCCTTATCCTCTGCGATGTTCTTCCTCTCAAAGTTTGCGATTTCTCTCTATC
AGAATTGCCATCAAGAGACTCAGGACTAATTTCGCAGTCCCACACGCACTCGTACA
TGATTGGCTGAAATTTCCCTAAAGAATTTCTTTTTCACGAAAATTTTTTTTTACACA
AGATTTTCAGCAGATATAAAATGGAGAGCAGGACCTCCGCTGTGACTCTTCTTTTTT
TTCTTTTATTCTCACTACATACATTTTAGTTATTCGCCAAC

FIG. 13

CONSTITUTIVE PROMOTER SEQUENCE
PP7435_CHR3-0476_SELECTION PICHIA PASTORIS CBS 7435 CHROMOSOME 3,
COMPLETE REPLICON SEQUENCE (SEQ ID NO: 14)

ATTGTTTATAGCCTATAATCGCAGACTTTGTTAACCCGTAGGAATAATCCTACCACT
AGAATTAGATCTTCCAACCATACATAGCGTGTACTACAACTTAAGCTGGTCCTCTTC
TTTTATCATTCGCGCGGCTCTATCTCATCTACACCTCCATTGAACTAATGGAAAGCA
AATACGCCGAAAAATATCAAGATCGATTGATTCTTGGAGATGATGGCGATGAGGA
CGAATTGTTTGACGAGCTGGAAAAGATATTGAGGATCAATTCTTGGCCAAATACA
GAGCAGAGAGAATCCAACAGTTAAAACAGGAGATTACCAAGATCAAGGACCATAG
TTCAAACATCAACCTCAATGACCACGGTAACATGAAAACAATAGATACTGATGACG
AACTATTGAAAGAAACTGTTGATAGCGAACGTGTTGTGATCCATTTCTTTAACCCAT
CGTTTAGCACTTGCCGTATCATGGATGAGAAGCTGTCTATAATCAGCACCAAACAT
ATTGGAACGCGTTTTTCAGAATTGAAGCACATAGAGCTCCATTTTTAGTTGCAAA
GCTTGGTATCAAAGTGCTTCCATGTGTTGTATTGTACTACAAAGGATTAGAAAGGG
ATAGAATTGTCGGATTTGACAGATTAAGTAATTCTCAGACCAATTTTGAGCTAGAA
GCTTTAGAGGAGTTACTCTTAGATAGTGGAATTGTGGAACGAAGAACTGTCGATTT
TAGCAACCTGAGAAACAAGGTCCAAAACAAGGTGGATCAGTCAAAATCAGACTCA
GAAAGTGATCTAGATATGTGATAGATGGCGGATGGCAGGTTCATTCTAGTGTTTCA
CGTGACACACGTGAGCGTTTAAGGGCACACACCCTGACTGACGCGCGAACATCTAA
TCTGTTCCGCATGAAAAAAAAAACTACCTCGACGAAATTCTCTTCTAGACAGTTT
TTACATTGGTAAGAAAGAAGCATTCACGTATTGCCGACGAAGCCAAA

FIG. 14

AOX1 PROMOTOR SEQUENCE (SEQ ID NO: 15)

GATCTAACATCCAAAGACGAAAGGTTGAATGAAACCTTTTTGCCATCCGACATCCA
CAGGTCCATTCTCACACATAAGTGCCAAACGCAACAGGAGGGGATACACTAGCAG
CAGACCGTTGCAAACGCAGGACCTCCACTCCTCTTCTCCTCAACACCCACTTTTGCC
ATCGAAAAACCAGCCCAGTTATTGGGCTTGATTGGAGCTCGCTCATTCCAATTCCTT
CTATTAGGCTACTAACACCATGACTTTATTAGCCTGTCTATCCTGGCCCCCTGGCG
AGGTTCATGTTTGTTTATTTCCGAATGCAACAAGCTCCGCATTACACCCGAACATCA
CTCCAGATGAGGGCTTTCTGAGTGTGGGGTCAAATAGTTTCATGTTCCCCAAATGG
CCCAAAACTGACAGTTTAAACGCTGTCTTGGAACCTAATATGACAAAAGCGTGATC
TCATCCAAGATGAACTAAGTTTGGTTCGTTGAAATGCTAACGGCCAGTTGGTCAAA
AAGAAACTTCCAAAAGTCGGCATACCGTTTGTCTTGTTTGGTATTGATTGACGAAT
GCTCAAAAATAATCTCATTAATGCTTAGCGCAGTCTCTCTATCGCTTCTGAACCCCG
GTGCACCTGTGCCGAAACGCAAATGGGGAAACACCCGCTTTTTGGATGATTATGCA
TTGTCTCCACATTGTATGCTTCCAAGATTCTGGTGGGAATACTGCTGATAGCCTAAC
GTTCATGATCAAAATTTAACTGTTCTAACCCCTACTTGACAGCAATATATAAACAG
AAGGAAGCTGCCCTGTCTTAAACCTTTTTTTTATCATCATTATTAGCTTACTTTCAT
AATTGCGACTGGTTCCAATTGACAAGCTTTTGATTTTAACGACTTTTAACGACAACT
TGAGAAGATCAAAAAACAACTAATTATTCGAAACG

FIG. 15

GENOMIC SEQUENCE, 1000BP UPSTREAM OF AOX1 PROMOTER ATG
(SEQ ID NO: 16)

CATGTTGGTATTGTGAAATAGACGCAGATCGGGAACACTGAAAAATAACAGTTATT
ATTCGAGATCTAACATCCAAAGACGAAAGGTTGAATGAAACCTTTTTGCCATCCGA
CATCCACAGGTCCATTCTCACACATAAGTGCCAAACGCAACAGGAGGGGATACACT
AGCAGCAGACCGTTGCAAACGCAGGACCTCCACTCCTCTTCTCCTCAACACCCACT
TTTGCCATCGAAAAACCAGCCCAGTTATTGGGCTTGATTGGAGCTCGCTCATTCCA
ATTCCTTCTATTAGGCTACTAACACCATGACTTTATTAGCCTGTCTATCCTGGCCCC
CCTGGCGAGGTTCATGTTTGTTTATTTCCGAATGCAACAAGCTCCGCATTACACCCG
AACATCACTCCAGATGAGGGCTTTCTGAGTGTGGGGTCAAATAGTTTCATGTTCCC
CAAATGGCCCAAAACTGACAGTTTAAACGCTGTCTTGGAACCTAATATGACAAAAG
CGTGATCTCATCCAAGATGAACTAAGTTTGGTTCGTTGAAATGCTAACGGCCAGTT
GGTCAAAAGAAACTTCCAAAAGTCGGCATACCGTTTGTCTTGTTTGGTATTGATT
GACGAATGCTCAAAAATAATCTCATTAATGCTTAGCGCAGTCTCTCTATCGCTTCTG
AACCCCGGTGCACCTGTGCCGAAACGCAAATGGGGAAACACCCGCTTTTTGGATGA
TTATGCATTGTCTCCACATTGTATGCTTCCAAGATTCTGGTGGGAATACTGCTGATA
GCCTAACGTTCATGATCAAAATTTAACTGTTCTAACCCCTACTTGACAGCAATATAT
AAACAGAAGGAAGCTGCCCTGTCTTAAACCTTTTTTTTTATCATCATTATTAGCTTA
CTTTCATAATTGCGACTGGTTCCAATTGACAAGCTTTTGATTTTAACGACTTTTAAC
GACAACTTGAGAAGATCAAAAAACAACTAATTATTCGAAACG

FIG. 16

Alpha-X-Gal plate assay for alpha-Galactosidase activity of *Pichia pastoris* transformants harboring a construct of a synthetic alpha-gal ORF fused with an isolated promoter sequences (SEQ ID NO:). No promoter has been inserted into a control plasmid. All constructs are integrated into genome of the transformants.

| Position | 1 | 2 | 3 | 4 | 5 |
|---|---|---|---|---|---|
| Row | | Plate 12 | | | |
| A |  | NO:7 | NO:7 | NO:7 | |
| B | NO:7 | NO:8 | NO:8 | NO:8 | NO:8 |
| C | Control | NO:8 | NO:5 | NO:10 | NO:10 |
| D | NO:10 | NO:14 | NO:14 | NO:14 | NO:14 |
| E | Control | Control | NO:12 | NO:12 | NO:12 |
| F | 09479 | 09479 | 09479 | NO:13 | UPP-513 |
| G | UPP-354 | DAS | 1-0469 | GAP | |
| H | NO:3 | NO:2 | NO:2 | NO:11 | NO:11 |
| I | NO:3 | NO:3 | NO:3 | NO:3 | |
| J |  | NO:3 | NO:3 | | |

| Position | 1 | 2 | 3 | 4 | 5 |
|---|---|---|---|---|---|
| Row | | Plate 23 | | | |
| A | NO:4 | NO:4 | NO:4 | NO:4 | |
| B | NO:4 | 11231 | 11231 | NO:1 | NO:1 |
| C | NO:1 | NO:14 | NO:14 | NO:14 | NO:14 |
| D | NO:14 | NO:14 | NO:2 | NO:2 | NO:2 |
| E | NO:2 | NO:2 | NO:2 | NO:2 | NO:2 |
| F | UPP-513 | UPP-354 | DAS | 1-0469 | GAP |
| G | 09479 | UPP 222 | NO:13 | NO:13 | |
| H | NO:2 | NO:2 | NO:13 | NO:2 | |
| I |  | NO:3 | NO:2 | NO:3 | |
| J |  | NO:3 | | | |

FIGURE 18, panel A

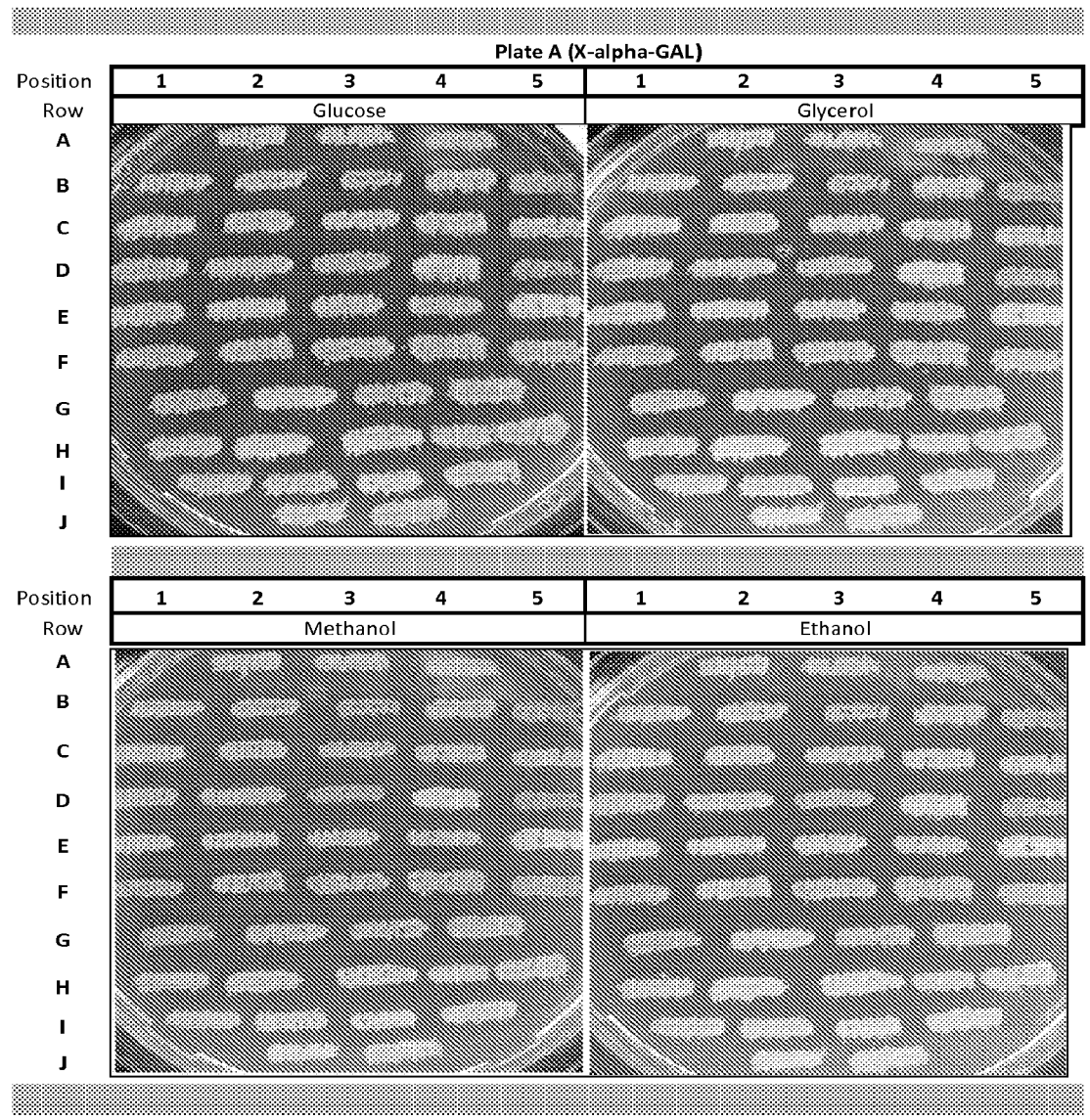
FIGURE 18, panel B

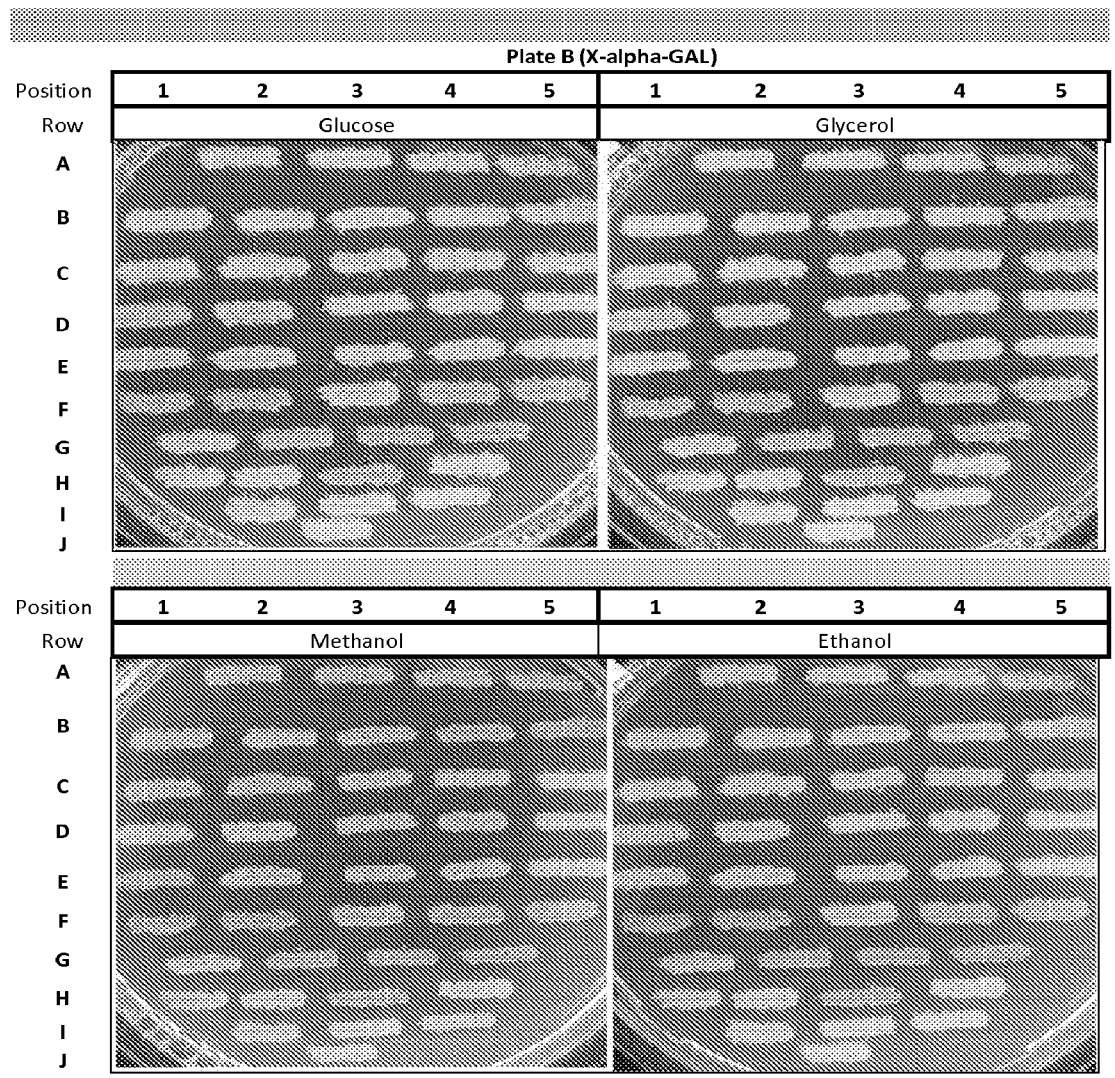
FIGURE 18, panel C

SEQUENCE LISTING

<160> NUMBER OF SEQ ID NOS: 37

<210> SEQ ID NO 1
<211> LENGTH: 1000
<212> TYPE: DNA
<213> ORGANISM: Pichia pastoris

<400> SEQUENCE: 1

| | | | | | |
|---|---|---|---|---|---|
| attgttgtga | atactctcct | tcatttggat | ttcttggact | tcggactctc | ttgatctctc | 60 |
| ttcgaaagtt | ttaactctgt | tcatgtataa | ttttacccgc | tgtaggtcgc | tcataatacc | 120 |
| atgagtatgc | acatctttta | ctccattaac | tttcaggtat | gcaaaataca | atgaagatag | 180 |
| tatatagctc | aaagaattta | gcattttgca | ttgatctaat | tgtgacattt | tctctatgat | 240 |
| atcatctagc | ttcttaaact | cgagaatctc | gtccaacgag | gcagaaacat | tgtccagtct | 300 |
| tacgtcaaga | ttattcacga | gtttctggac | cgtatcaacg | ttttccatct | taagattaca | 360 |
| gtaagtatcg | tccttttgaa | ctgcaaaggt | agaaaagtta | attttttgatt | tggtagtaca | 420 |
| ctatgaaact | tgctcacccc | aatctttcct | cctgacaggt | tgatctttat | ccctctacta | 480 |
| aattgcccca | gtgtatcaa | gtagactaga | tctcgcgaaa | gaacagccta | ataaactccg | 540 |
| aagcatgatg | gcctctatcc | ggaaaacgtt | aagagatgtg | gcaacaggag | ggcacataga | 600 |
| attttttaaag | acgctgaaga | atgctatcat | agtccgtaaa | aatgtgatag | tactttgttt | 660 |
| agtgcgtacg | ccacttattc | ggggccaata | gctaaaccca | ggtttgctgg | cagcaaattc | 720 |
| aactgtagat | tgaatctctc | taacaataat | ggtgttcaat | cccctggctg | gtcacgggga | 780 |
| ggactatctt | gcgtgatccg | cttggaaaat | gttgtgtatc | cctttctcaa | ttgcggaaag | 840 |
| catctgctac | ttcccatagg | caccagttac | ccaattgata | tttccaaaaa | agattaccat | 900 |
| atgttcatct | agaagtataa | atacaagtgg | acattcaatg | aatatttcat | tcaattagtc | 960 |
| attgacactt | tcatcaactt | actacgtctt | attcaacaat | | | 1000 |

<210> SEQ ID NO 2
<211> LENGTH: 1000
<212> TYPE: DNA
<213> ORGANISM: Pichia pastoris

<400> SEQUENCE: 2

| | | | | | |
|---|---|---|---|---|---|
| gtcaactgcg | tactcttttg | tcgaatggac | tactgaatct | gcctcgatag | ccactatagg | 60 |
| aaggtccata | gaggccagtt | tttcaactag | tcttggtgga | aagaaaccga | caaagccttt | 120 |
| catggagtca | ccgatactga | aaggttcaaa | caaagaatgc | ttgggtagtc | tcttaatacc | 180 |
| catggcaacg | aaaaagggt | cttcattgtt | caacatgaat | tcgtatccac | ctttaatgta | 240 |
| gtcataaagc | tgctgaagtt | ccgaatcagt | gatggaactg | tctacagtga | caatatagga | 300 |
| gttctcaatc | accttatatc | cagtcgaata | tatctggata | gggtcgggtc | tcactgtgga | 360 |
| agattcaaat | gggttagatc | cctgtaattt | cagcgatgga | gactcagtat | gatggggcaa | 420 |
| ggaaaacggc | aattggatat | tcaattggtc | aagagatggt | atcaaaagcg | agtgtgccag | 480 |
| ggtagccacg | gtagccactg | atgctaatct | gataattttc | atttctggag | tgtcaaaaca | 540 |
| gtagtgataa | aaggctatga | aggaggttgt | ctagggctc | gcggaggaaa | gtgattcaaa | 600 |
| cagacctgcc | aaaagagaa | aaagaggga | atccctgttc | tttccaatgg | aaatgacgta | 660 |
| actttaactt | gaaaaatacc | ccaaccagaa | gggttcaaac | tcaacaagga | ttgcgtaatt | 720 |
| cctacaagta | gcttagagct | gggggagaga | caactgaagg | cagcttaacg | ataacgcggg | 780 |
| gggattggtg | cacgactcga | aaggaggtat | cttagtcttg | taacctcttt | tttccagagg | 840 |

```
ctattcaaga ttcataggcg atatcgatgt ggagaagggt gaacaatata aaaggctgga    900
gagatgtcaa tgaagcagct ggatagattt caaattttct agatttcaga gtaatcgcac    960
aaaacgaagg aatcccacca agcaaaaaaa aaaaatctaa                         1000
```

<210> SEQ ID NO 3
<211> LENGTH: 1000
<212> TYPE: DNA
<213> ORGANISM: Pichia pastoris

<400> SEQUENCE: 3

```
tgctgttttg ggctcgtacg gatgtttctt aggtccgatg attggtgtta tgacttgtga     60
ctactacttc gtacgtcatc agaaactcaa gctgacagac ctctacaaag ccgacaagag    120
ttctatttac tggttctaca aaggattcaa ctggagaggt ttcgttgcct ggatttgcgg    180
ttttactcca ggtattacag ggtttcctag cgtcaacccc aacttgactg gggttcctac    240
agcctgtatc aagatgttct acatttcgtt tatcattggt tacccgatcg gattcttagt    300
tcatctggca ctcaataagc tattccctcc accaggtctt ggtgaagtcg atgagtatga    360
ctactaccac tctttcaccg aaaaggaagc actgaaatta ggaatggccc ctagttccga    420
gttggacaga gtcagcaccg atgacccgat caatattcct tacgacgaga agtctttagg    480
ctaatgtagt taaatagtta atcgaaacaa tcgtgtatcc tctttatcgt accagcggga    540
ttcgctgctt ggatgggtga ctcctgtcca gttgactcaa agtagtcaaa ataggcctgg    600
agacccttaa caggtcgatg agtagcctac tatgagaaaa cccctcacca caactggact    660 ataaagggc acgtcaatcc ccaaagcaac tcttttcttt catccctact ttattacttt    720
atcctttgat cttcattgaa gaaaatctga acaattgta agcagcaatc cacacctccc    780
cagcaatgac tcaatttact aaccccattg acagaaaatg tgagcatctt ttttagatgt    840
catgatgata ggtggagtat tcttaattat tgctttcagc aaaccggtgc ccataaagtg    900
tttcccatta aatcaatgag aggcattaag gctgagatta aacggttgaa cttgaactag    960
ataattctag cggaaagaat tgctcttttt attacgtcgt                         1000
```

<210> SEQ ID NO 4
<211> LENGTH: 1000
<212> TYPE: DNA
<213> ORGANISM: Pichia pastoris

<400> SEQUENCE: 4

```
aggctctgcg caaggcaact gagaaattga atagtggttt caagcccgct gacttttgt     60 attatctcaa tgtcggtgtt tcacagtccc cagaagggg ctttgccttc aagggagacg    120
gaagagacat cgtcaaccct ggggagaagt atttcaaatg cgcaagttc gctaattttt    180 acgattaagc agtgctgtat ggggtagtta ataaatcggg aatatccttc tgacgtgact    240
gtaacaaatc tctttttacg tggtgcgcat actggacaga ggcagagtct caatttcttc    300
ttttgagaca ggctactaca gcctgtgatt cctcttggta cttggatttg cttttatctg    360
gctccgttgg gaactgtgcc tgggttttga agtatcttgt ggatgtgttt ctaacacttt    420
ttcaatcttc ttggagtgag aatgcaggac tttgaacatc gtctagctcg ttggtaggtg    480
aaccgtttta ccttgcatgt ggttaggagt tttctggagt aaccaagacc gtcttatcat    540
cgccgtaaaa tcgctcttac tgtcgctaat aatcccgctg gaagagaagt tcgaacagaa    600
gtagcacgca aagctcttgt caaatgagaa ttgttaatcg tttgacaggt cacactcgtg    660
```

```
ggctatgtac gatcaacttg ccggctgttg ctggagagat gaccaccagtt gtggcatggc    720 caattggtat tcagccgtac cactgtatgg aaaatgagat tatcttgttc ttgatctagt    780
ttcttgccat tttagagttg ccacattcgt aggtttcagt accaataatg gtaacttcca    840
aacttccaac gcagataccca gagatctgcc gatccttccc caacaatagg agcttactac    900
gccatacata tagcctatct attttcactt tcgcgtgggt gcttctatat aaacggttcc    960
ccatcttccg tttcatacta cttgaatttt aagcactaaa                          1000
```

<210> SEQ ID NO 5
<211> LENGTH: 1000
<212> TYPE: DNA
<213> ORGANISM: Pichia pastoris

<400> SEQUENCE: 5

```
caaacttaac cgaccgttct tccatccgtt tattaatata cacacctatg aactgagcca     60
ggttttcagg tctctgtgac tctctataca ttgacggaac aacatccgtt cagtctcatc    120
caattgcagc ccaaactctg agtttagcaa ttgcaaatgg ttattatctg acgagtaatc    180
gttgatggca catgccctct gtttgaacat ctcttgaaca atagccatca gttctgtgtc    240
attaaacatg cttccccatt tcactgacag tttgtagaaa tagggcaaca attgatgcaa    300
atcgattttc aacgcattgg ttttgatagc attgatgatc ttggagctgt aaaagtccgg    360
ctggataagc tcaatgaaat aggttggttg atctggatct tcttttgggt cattttgttc    420
gctctgtatt tcacaaattg ccagaatctc tgccaaccac agtggtaggt ccaacttggt    480
gttctgaatc acaggcttcc ccgggttgtt ctctaaataa ccgaggcccg gcacagaaat    540
cgtaaaccga cacggtatct tttgtccgtc cgccagtatc tcatcaaggt cgtagtagcc    600
catgatgagt atcaaagggg atttggttat gcgatgcaac gagagattgt ttatcccaga    660
tgctgatgta aaaaccttaa ccagcgtgac agtagaaata agacacgtta aaattacccg    720
cgcttcccta acaattggct ctgccttccg gcaagtttct aactgccctc ccctctcaca    780
tgcaccacga acttaccgtt cgctcctagc agaaccaccc caaagtttaa tcaggaccgc    840
attttagcct attgctgtag aaccccacaa cataacctgg tccagagcca gccctttata    900
tatggtaaat cccgtttgaa cttcgaagtg gaatcggaat ttttacatca aagaaactga    960
tactgaaact tttggcttcg acttggactt tctcttaatc                         1000
```

<210> SEQ ID NO 6
<211> LENGTH: 1000
<212> TYPE: DNA
<213> ORGANISM: Pichia pastoris

<400> SEQUENCE: 6

```
gtaaataagt taaagtttaa aaaggaaagg atgcaaaaaa tatccttgaa ggcaacgaat     60
attttgaaat ccccgatgcc aaataaatgc tatcacttaa agagcacaat agaggtggaa    120
aaagaaaaac ttggtcaagc taagggttag caagtttctg tttgtgataa tcagggagaa    180
ggtgtcagaa aaaacatgat tatgtaagtg gtgttaggag ccgttaaagc attctgtcgg    240
ccaatagcaa gcccgccttt tgtcatcttt ttgcggtttc tctgtgtgag acactaatca    300
cctttgtaag acatcgggaa aaccgttgcg caaaatgaga tagagattgt tctcgataga    360
ggagcgtagt agcctctcca gcctgcttta gcaacataat agaaaagaaa tatgcgttgc    420
ctagggaggc tacgtatgcc cagcataaac gagtgtttac cttacttcgc acgagcagta    480
gccactaaga tcattataaa ctcacctatt gtcttcatgc tgtgctccgc gtatttgtct    540
```

```
gttcagggtg tcatttctcg tcatgagaat ctgattgatg actatgcgag attacccctg    600 gattttttt gatcccgtaa cgcgaacttg aacattgact ttgatatggc aatgggccct    660
aatatgccct aatatgccct aagcttaaca attgacttct gttctctggc agactccaca    720
gaaaactggt tgacaggtct aatttctttt tgaatcattt ccggtgattc attttgatgc    780
ttagagtgag tcatgggttc tttatccgca ttcttcttcg cgtctgctgt gcttaataat    840
agcctactaa aaatgtgggg agcctcttac cttatgtcta taaaaacaag cacatgacta    900
tgccatcgcc ttcatagttg ttctgcgggt ttttgcttgt tttatgaccg tagagaccaa    960
ccaatttaca tatctacagg gtagcacatt cgataagaaa                         1000

<210> SEQ ID NO 7
<211> LENGTH: 1000
<212> TYPE: DNA
<213> ORGANISM: Pichia pastoris

<400> SEQUENCE: 7
gaagggctac aggttgttcg agtcaaccaa gaaaaaaatg tctccattcc attccttca     60 gaagtctgtg atgtgagatt cagtagcaac gaaactacac ccatagtcag accaaatgaa    120
accagtcaag acttttcaat ctggctcaaa gaccagccag gaatcagaga gttttacaa    180 aattcgacca tcgcacttgg atctagactc aatctcttaa gcaatgtaaa tattgagata    240
catggggaga cagtgaatta taccttcaca gaaatcgaac agaggagaca attagaactg    300
aattacagac aacaccttct tcaatattca gcagtggaag gaggactact gggtgggaaa    360
agaacagaag tcaatctggt aaatatggct gaagcccctg caactacaga gtcatttgcc    420
aagttttcca aggacgttct ggatcttgtt cgtatactaa gttgtacata gagtgaatat    480
aagaacaggg gcccagttaa gactagatct atcaatactg taatctagac tgaataaacc    540
tgaatggcaa agaaacacca aatggagatt tccgaggtag tatcgaccgc acttacgagg    600
gcggatatgt gtcctcctga tgtatagtta cgtcataaag tattgatgcc tagaccattt    660
caatttcgta gtcatctatt cgtgaaaaga ggcaaggctg attgttcaat ttggcaatga    720
tgagccaaca gtgcttaaaa ctggacaaaa cttagatcaa atattcaccg ttgtaaaaca    780
cagttcctct cgtcttcatt ttagcccatt gcacaaaaac cccaactttt acattccgga    840
aaaaaaatgc tcctccacct agatgcagag tgtaccgctc aaagaaccct cgatgagttt    900
cgaccatctt caccaagtga ataatatttt atagtgaggg aaagaacatt ttttcccctg    960
ttcgtttctt taccagttaa ctactacaga atcttctaaa                         1000

<210> SEQ ID NO 8
<211> LENGTH: 1000
<212> TYPE: DNA
<213> ORGANISM: Pichia pastoris

<400> SEQUENCE: 8
tggatctgga tgtagatgca actgcccgaa aaaatacaaa gaattagaag atagtcccag    60
ctgctgtatt ggcagatgga tggtattaac taacgataag tataaaggcg aaaaatacct    120
agataaatac tcaatggccg aagaggtcaa gcagactcta agcaagggtg aaaaactaaa    180
cgttaaagag atattgaaga ggcaccacaa gtatccaaca tgagaagaga acccagaaag    240
agtcaaaata caaactcgaa acataccga ttggcagaat accagccata cattacattt    300
gatactaata tacataaaat acactaacct ccgaaaccat acaaggtacg tccttgtctt    360
```

| | |
|---|---|
| ttcaaagcgt agacgacatc cagagaagta acagtctttc tcttggcatg ctcagtgtaa | 420 |
| gtaacagcat ctctaatgac gttctctaag aaagtcttca gcacagctct gacttcttcg | 480 |
| tagatcaaag cggaaatacg cttaacacca cctcttctgg ccaatcttct gatagctggc | 540 |
| tttgtgatac cttgaatgtt gtctctaaga atctttctgt gacgcttagc accggatttt | 600 |
| cctagacctt ttccaccttt tcctctacca gacatattta ttgattattt gtttatgggt | 660 |
| gagtctagaa aaggacgcac tcgtcttgta tttatagatg aaaagagtta aggtggacaa | 720 |
| tgcagtgcca aaccgtaatg ttgatacgac acggtacgcg atgaactgag ccgtactcct | 780 |
| agaggcagag cgtgcgtaaa tttgaaactg taagaacatg tcccatttct atgctaccag | 840 |
| aactcataat aaacttgcat cccatttcag tcgggagtgt cgcagtgcga aatactgttg | 900 |
| gcactgatgg caaaaagtgc caaatcgtta tctatgggag actcttataa atatccagat | 960 |
| cctccccctc ctgcttcttc ttgtgtctat cgtagtaaaa | 1000 |

<210> SEQ ID NO 9
<211> LENGTH: 1000
<212> TYPE: DNA
<213> ORGANISM: Pichia pastoris

<400> SEQUENCE: 9

| | |
|---|---|
| gatcgaggac atggtgtttt tttttttat agaagtatca tactaagtgt acttttcact | 60 |
| tgcttatcct cttttctacc tcaccctcat aagcaggaaa ttcttgacaa tcgcaagagt | 120 |
| aagcgtgcac tacacagcca tcggcaacac cgaatttcac cttacagcca gtttgtatct | 180 |
| cccttaaata tcgtattcga ttaatataca ctacattaca cttaggatct ttcacctctc | 240 |
| agtcttctag ctaacaggat atccttcttt tggatagtaa ctctcttagc gtgaatagca | 300 |
| cacaagttag tatcttcgaa caaggaaacc aagtaagctt cgacggattc ttgcaaagca | 360 |
| ccgatggcag aagattggaa tctcaggtca gtcttgaagt cctgagcaat ttctctgacc | 420 |
| aatctttgga aaggcagctt tctgataagc aactcagtag acttttggaa tcttctgatt | 480 |
| tctctcagag caacggtacc tggcttatat ctgtggggct tcttgacacc tccagcagca | 540 |
| gatggagcga ttttctggc agccttggaa gccaattgct tcttggggc tttaccacca | 600 |
| gtggatttc ttgctgtttg tttagttcta gccattttta ctacgataga cacaagaaga | 660 |
| agcaggaggg ggaggatctg atatttata agagtctccc atagataacg atttggcact | 720 |
| ttttgccatc agtgccaaca gtatttcgca ctgcgacact cccgactgaa atgggatgca | 780 |
| agtttattat gagttctggt agcatagaaa tgggacatgt tcttacagtt tcaaatttac | 840 |
| gcacgctctg cctctaggag tacggctcag ttcatcgcgt accgtgtcgt atcaacatta | 900 |
| cggtttggca ctgcattgtc caccttaact cttttcatct ataaatacaa gacgagtgcg | 960 |
| tcctttttcta gactcaccca taaacaaata atcaataaat | 1000 |

<210> SEQ ID NO 10
<211> LENGTH: 1000
<212> TYPE: DNA
<213> ORGANISM: Pichia pastoris

<400> SEQUENCE: 10

| | |
|---|---|
| ttccatatta cttcagcaaa tacaagtaca aatcacttga ctcgtatcag ttcttggata | 60 |
| ccctttatga gttttctca gataaacatg aaatttaga caaagttgac tgggaaactt | 120 |
| ggttgtacaa gtttggatta ccaccaaagc caaagtttga tacctcgcta gttgatgaat | 180 |
| gctatgattt agctgccaaa tgggttgatg tcaccaagaa ggatagcaaa gatctttga | 240 |

```
agaaaacttt cagctcagat gatatttcta atttcacggg taaccaaact aacgtcttcc      300
ttgatacttt agtatcttat caaggagtgg aaggtttcct gtggaattcc aaagaagggg      360
aacaagcttt gacgtttatg agagagagct atagcgttta tgacgactcc aagaatgcag      420
aagtcatttt ccgctggtac agactacaat taacagggag aagcaagcag tactaccagc      480
gtctggccga ttggctggga acaatcggac gaatgaaatt tgttcgacca tcttatcgaa      540
tgctcaacga tgtggaccct caactggcca aggacacatt cttgaagttt gagccaatct      600
accatccgat ctgtcgatca atgatccgca aggacttaca cttgtagaga aaaaggtat       660 gtggggtata cgtaagtacg ttaagtatgc caaaaacatc acaatagaca atacgcccta      720
caacagaacg tcaagttgta cgcgagcacc gttaaatcac acgtaacatc caacacctt       780 cttttggtagg gcatagcccc aggtggcacc acgtgcataa accattttac accccaacac     840
ccaccaatcc tcgccctctg gcatttgctc aaattttta accagcttct gattacatag       900
gtaaccagtt caattcatag gtaagtcaac gccgaacaac aagggaaatc acccatccgc      960
tcacatcagt ccagttgaag actaacatta aaagacaaaa                           1000

<210> SEQ ID NO 11
<211> LENGTH: 1000
<212> TYPE: DNA
<213> ORGANISM: Pichia pastoris

<400> SEQUENCE: 11
tggtaatcaa ctcactattt cattcatgtc aacagccccg aaaacgataa ttaatagaca       60
accccaatca tatttagtga gttttcggat taaagcttgt tcgcgttccg gttgatgatg      120
gtttcaagaa aatgctgagc tcgctcttat actgggtccc ttgaaatgat atgcatatgt      180
tgggaatacg ctaatgtact ttgacagata ttgcttctcc ttgtagcaaa ttgacagttt      240
cgtttgcaac tgtaacactt ggtgatcgat atttggataa acacaattac tattttggag      300
ttacaaccag aattcgtctt aatgtttcgc atccttgttc aaagactaaa acttcttcga      360
tttcgaattt gtcttaagta ttgactagtc gggctcaaag agcaacacta gctggaaacg      420
gctcaggatc actttcgttt tttttctaga aaatgaggca attgtaggac tgggtctctt      480
tatctgcaat ttgtgtaagc tggtttactg ttctcaacaa aatagaagtg aaccgtccgt      540
gatgtaaaat gagactactc cgttgaatcg caacaagtat tatatcctag cttaaggtga      600
ttcttaactt tggagcaaaa atatcgtgta acaacgccgg ctcagtcaat cttctttgaa      660
ttaacactgc acctctatct tgaacactat ctacatgagt gtgcaaccag aaagaatgca      720
aagattaatt ttcttaccca caatgtggtc cgatccacaa ttctagtgaa ttcctaacat      780
gtttagtacc aacgtttgaa caacagatac atcacattga aaaaaggat tgagaataat       840 aatcaaattt tcagcattat atagtaccac gaaactaaat cgctttggaa ggagaaacat      900
tttcaagctg ttaaactgga tttatccaaa atagttagtt tgcacaagtt taaaaggagg      960
tgtctaacag gtggggaaaa atcagttaat tgagttttta                           1000

<210> SEQ ID NO 12
<211> LENGTH: 1000
<212> TYPE: DNA
<213> ORGANISM: Pichia pastoris

<400> SEQUENCE: 12 caggggggcag ttacttcatt atatgtagta agttgtctaa taacacttta gaattgaggg      60
```

| | |
|---|---:|
| ttgtactaac caaacagaca ctgttgcaag ttatggtgac aaggttgctt tcaagccctg | 120 |
| atactaaagt ggttcatatt tgcatgagtg gttcgtatcc ggaggatcat ctacagaacg | 180 |
| tgctaaaatc attatctttt ggtgacgaaa aaagaagtt accattggat gacaagacaa | 240 |
| agaatactat tttagatagt atttggctgg cttaccctga cgatctgaat gagtcgtacg | 300 |
| aacaattgga gaaacttcaa gaagagaatt cagcgggtct ctcaaaactg atgattgtta | 360 |
| ttcaagattt ggatgatatg gctgagttat acgccttcag agatttcaca tcaggtaagt | 420 |
| ttacactctg aaattttgat tacaaaatat atactaacac atttagcctg tgctacattg | 480 |
| atgaatttca tgcttaaatt aagaaaaatc agtcaactgg gagctacggt catagttact | 540 |
| aatatcaatc atgactctgg agtgtctatg atattctcct acatagccaa gttttacgac | 600 |
| aataaactaa cgttcagctt tcacaaaggc tcaatacttt tagagatacg tcctctaacg | 660 |
| atatcaaccg aacttcagct cagcactact acactctcta tcaacccaca aacgatgtac | 720 |
| cacatgcttt tccccagctc tgaaaatgcc cttatcagca cgtgattaaa gatgagggct | 780 |
| cgctgacaag atgtgactag actgccacct ttacaccctc agagaagaca aacgtctcat | 840 |
| ttcgcggtta gtaaggttaa cccacaaatt ttcaacgtgt actacccaag agctctctgt | 900 |
| ctgccatggg cgcgcgcaca ctccctggtg tgcgaatcca accaaagtat gaaaaaaaaa | 960 |
| aaccattact tcaaagtttt ctttcaacac acaaagaag | 1000 |

<210> SEQ ID NO 13
<211> LENGTH: 1000
<212> TYPE: DNA
<213> ORGANISM: Pichia pastoris

<400> SEQUENCE: 13

| | |
|---|---:|
| gtatttgaca ggttggggag caaataagtg atgatgtccc atgaaagtag aaaatggcta | 60 |
| gtagaaggca aaaatttgaa attcttagag tcaaatagtt agactccaag ttctaatcca | 120 |
| catttggtca gtttcatagc atccagagct tttgccactg tgaacatat ctacccattg | 180 |
| cgatgcaaca agtcactgaa agcctaaaac ggagattccc ctatcttaca gcctcgttca | 240 |
| aaaaaactgc taccgtttat ctgctatggc cgatgtgagg atgcgctcat gcccaagagt | 300 |
| ccaactttat caaaaacttg acccgtcata caggctctag atcaagaagc aaacttaatc | 360 |
| tcagcatctg gttacgtaac tctggcaacc agtaacacgc ttaaggtttg gaacaacact | 420 |
| aaactacctt gcggtactac cattgacact acacatcctt aattccaatc ctgtctggcc | 480 |
| tccttcacct tttaaccatc ttgcccattc caactcgtgt cagattgcgt atcaagtgaa | 540 |
| aaaaaaaaaa ttttaaatct ttaacccaat caggtaataa ctgtcgcctc ttttatctgc | 600 |
| cgcactgcat gaggtgtccc cttagtggga aagagtactg agccaaccct ggaggacagc | 660 |
| aagggaaaaa tacctacaac ttgcttcata atggtcgtaa aaacaatcct tgtcggatat | 720 |
| aagtgttgta gactgtccct tatcctctgc gatgttcttc ctctcaaagt ttgcgatttc | 780 |
| tctctatcag aattgccatc aagagactca ggactaattt cgcagtccca cacgcactcg | 840 |
| tacatgattg gctgaaattt ccctaaagaa tttcttttc acgaaaattt ttttttttaca | 900 |
| caagattttc agcagatata aaatggagag caggacctcc gctgtgactc ttctttttt | 960 |
| tcttttattc tcactacata catttagtt attcgccaac | 1000 |

<210> SEQ ID NO 14
<211> LENGTH: 1000
<212> TYPE: DNA
<213> ORGANISM: Pichia pastoris

<400> SEQUENCE: 14

```
attgtttata gcctataatc gcagactttg ttaacccgta ggaataatcc taccactaga      60
attagatctt ccaaccatac atagcgtgta ctacaactta agctggtcct cttctttat     120
cattcgcgcg gctctatctc atctacacct ccattgaact aatggaaagc aaatacgccg     180
aaaaatatca agatcgattg attcttggag atgatggcga tgaggacgaa ttgtttgacg     240
agctggaaaa agatattgag gatcaattct tggccaaata cagagcagag agaatccaac     300
agttaaaaca ggagattacc aagatcaagg accatagttc aaacatcaac ctcaatgacc     360
acggtaacat gaaaacaata gatactgatg acgaactatt gaaagaaact gttgatagcg     420
aacgtgttgt gatccatttc tttaacccat cgtttagcac ttgccgtatc atggatgaga     480
agctgtctat aatcagcacc aaacatattg gaacgcgttt tttcagaatt gaagcacata     540
gagctccatt tttagttgca aagcttggta tcaaagtgct tccatgtgtt gtattgtact     600
acaaaggatt agaaagggat agaattgtcg gatttgacag attaagtaat tctcagacca     660
attttgagct agaagcttta gaggagttac tcttagatag tggaattgtg aacgaagaa     720
ctgtcgattt tagcaacctg agaaacaagg tccaaaacaa ggtggatcag tcaaaatcag     780
actcagaaag tgatctagat atgtgataga tggcggatgg caggttcatt ctagtgtttc     840
acgtgacaca cgtgagcgtt taagggcaca caccctgact gacgcgcgaa catctaatct     900
gttccgcatg aaaaaaaaaa actacctcga cgaaattctc ttctagacag tttttacatt     960
ggtaagaaag aagcattcac gtattgccga cgaagccaaa                          1000
```

<210> SEQ ID NO 15
<211> LENGTH: 939
<212> TYPE: DNA
<213> ORGANISM: Pichia pastoris

<400> SEQUENCE: 15

```
gatctaacat ccaaagacga aaggttgaat gaaacctttt tgccatccga catccacagg      60
tccattctca cacataagtg ccaaacgcaa caggagggga tacactagca gcagaccgtt     120
gcaaacgcag gacctccact cctcttctcc tcaacaccca cttttgccat cgaaaaacca     180
gcccagttat tgggcttgat tggagctcgc tcattccaat tccttctatt aggctactaa     240
caccatgact ttattagcct gtctatcctg gcccccctgg cgaggttcat gtttgtttat     300
ttccgaatgc aacaagctcc gcattacacc cgaacatcac tccagatgag ggctttctga     360
gtgtggggtc aaatagtttc atgttcccca aatgggccaa aactgacagt ttaaacgctg     420
tcttggaacc taatatgaca aaagcgtgat ctcatccaag atgaactaag tttggttcgt     480
tgaaatgcta acggccagtt ggtcaaaaag aaacttccaa aagtcggcat accgtttgtc     540
ttgtttggta ttgattgacg aatgctcaaa ataatctca ttaatgctta gcgcagtctc     600
tctatcgctt ctgaacccg gtgcacctgt gccgaaacgc aaatgggaa acacccgctt     660
tttggatgat tatgcattgt ctccacattg tatgcttcca agattctggt gggaatactg     720
ctgatagcct aacgttcatg atcaaaattt aactgttcta accctactt gacagcaata     780
tataaacaga aggaagctgc cctgtcttaa accttttttt ttatcatcat tattagctta     840
ctttcataat tgcgactggt tccaattgac aagcttttga ttttaacgac ttttaacgac     900
aacttgagaa gatcaaaaaa caactaatta ttcgaaacg                           939
```

<210> SEQ ID NO 16

```
<211> LENGTH: 1001
<212> TYPE: DNA
<213> ORGANISM: Pichia pastoris

<400> SEQUENCE: 16
catgttggta ttgtgaaata gacgcagatc gggaacactg aaaaataaca gttattattc      60
gagatctaac atccaaagac gaaaggttga atgaaacctt tttgccatcc gacatccaca     120
ggtccattct cacacataag tgccaaacgc aacaggaggg gatacactag cagcagaccg     180
ttgcaaacgc aggacctcca ctcctcttct cctcaacacc cacttttgcc atcgaaaaac     240
cagcccagtt attgggcttg attggagctc gctcattcca attccttcta ttaggctact     300
aacaccatga ctttattagc ctgtctatcc tggcccccct ggcgaggttc atgtttgttt     360
atttccgaat gcaacaagct ccgcattaca cccgaacatc actccagatg agggctttct     420
gagtgtgggg tcaaatagtt tcatgttccc caaatggccc aaaactgaca gtttaaacgc     480
tgtcttggaa cctaatatga caaaagcgtg atctcatcca agatgaacta agtttggttc     540
gttgaaatgc taacggccag ttggtcaaaa agaaacttcc aaaagtcggc ataccgtttg     600
tcttgtttgg tattgattga cgaatgctca aaaataatct cattaatgct tagcgcagtc     660
tctctatcgc ttctgaaccc cggtgcacct gtgccgaaac gcaaatgggg aaacacccgc     720
tttttggatg attatgcatt gtctccacat tgtatgcttc caagattctg gtgggaatac     780
tgctgatagc ctaacgttca tgatcaaaat ttaactgttc taacccctac ttgacagcaa     840
tatataaaca gaaggaagct gccctgtctt aaacctttt ttttatcatc attattagct     900
tactttcata attgcgactg gttccaattg acaagctttt gattttaacg acttttaacg     960
acaacttgag aagatcaaaa acaactaat tattcgaaac g                         1001

<210> SEQ ID NO 17
<211> LENGTH: 34
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(3)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other

<400> SEQUENCE: 17
nnnggtctcn atccacgagt ttctggaccg tatc                                  34

<210> SEQ ID NO 18
<211> LENGTH: 32
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(3)
<223> OTHER INFORMATION: a, c, t, g, unknown or other

<400> SEQUENCE: 18
nnnggtctct atccggaaaa cgttaagaga tg                                    32
```

```
<210> SEQ ID NO 19
<211> LENGTH: 36
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(3)
<223> OTHER INFORMATION: a, c, t, g, unknown or other

<400> SEQUENCE: 19
nnnggtctct atccctctac taaattgccc caagtg                              36

<210> SEQ ID NO 20
<211> LENGTH: 38
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(3)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other

<400> SEQUENCE: 20
nnnggtctcn atccgatgga gactcagtat gatggggc                            38

<210> SEQ ID NO 21
<211> LENGTH: 37
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(3)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other

<400> SEQUENCE: 21
nnnggtctcn atccagtatg atggggcaag gaaaacg                             37

<210> SEQ ID NO 22
<211> LENGTH: 34
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(3)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other

<400> SEQUENCE: 22
nnnggtctcn atcctggaga cccttaacag gtcg                                34
```

<210> SEQ ID NO 23
<211> LENGTH: 31
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (1)..(3)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other

<400> SEQUENCE: 23
nnnggtctcn atccgttggg aactgtgcct g                              31

<210> SEQ ID NO 24
<211> LENGTH: 35
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (1)..(3)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other

<400> SEQUENCE: 24
nnnggtctcn atccacagtg gtaggtccaa cttgg                          35

<210> SEQ ID NO 25
<211> LENGTH: 34
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (1)..(3)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other

<400> SEQUENCE: 25
nnncgtctcn atccgtagta gcctctccag cctg                           34

<210> SEQ ID NO 26
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (1)..(3)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other

<400> SEQUENCE: 26
nnnggtctcn atcctgaagc ccctgcaact acagag        36

<210> SEQ ID NO 27
<211> LENGTH: 40
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(3)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other

<400> SEQUENCE: 27
nnnggtctcn atccgtagac gacatccaga gaagtaacag        40

<210> SEQ ID NO 28
<211> LENGTH: 38
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(3)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other

<400> SEQUENCE: 28
nnnggtctcn atcctcaggt cagtcttgaa gtcctgag        38

<210> SEQ ID NO 29
<211> LENGTH: 35
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(3)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other

<400> SEQUENCE: 29
nnnggtctcn atcctgtgga attccaaaga agggg        35

<210> SEQ ID NO 30
<211> LENGTH: 38
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(3)

```
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other

<400> SEQUENCE: 30
nnnggtctcn atccgtccgt gatgtaaaat gagactac                                38

<210> SEQ ID NO 31
<211> LENGTH: 34
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(3)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other

<400> SEQUENCE: 31
nnnggtctcn atccagtcaa ctgggagcta cggt                                    34

<210> SEQ ID NO 32
<211> LENGTH: 31
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(3)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other

<400> SEQUENCE: 32
nnnggtctcn atccgatgtg aggatgcgct c                                       31

<210> SEQ ID NO 33
<211> LENGTH: 39
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(3)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other

<400> SEQUENCE: 33
nnnggtctcn atcctcaatg accacggtaa catgaaaac                               39

<210> SEQ ID NO 34
<211> LENGTH: 37
<212> TYPE: DNA
<213> ORGANISM: Artificial Sequence
<220> FEATURE:
```

```
<223> OTHER INFORMATION: Description of Artificial Sequence: Synthetic
      primer
<220> FEATURE:
<221> NAME/KEY: modified_base
<222> LOCATION: (1)..(3)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other

<400> SEQUENCE: 34
nnnggtctcn atccaatgga ccaaattgtt gcaaggt                              37

<210> SEQ ID NO 35
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(3)
<223> OTHER INFORMATION: a, c, t, g, unknown or other

<400> SEQUENCE: 35
nnnggtctcc atccctttgt tgagcaaca                                      29

<210> SEQ ID NO 36
<211> LENGTH: 28
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(3)
<223> OTHER INFORMATION: a, c, t, g, unknown or other

<400> SEQUENCE: 36
nnnggtctcg atccgcccaa acgaacag                                       28

<210> SEQ ID NO 37
<211> LENGTH: 34
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(3)
<223> OTHER INFORMATION: a, c, t, g, unknown or other

<400> SEQUENCE: 37
nnnggtctcc atccaaagac gaaaggttga atga                                34
```

YEAST PROMOTORS FOR PROTEIN EXPRESSION

CROSS-REFERENCE TO RELATED APPLICATIONS

This application is a continuation of U.S. application Ser. No. 14/773,482, filed Sep. 8, 2015, which is a U.S. national application filed under 37 C.F.R. § 371(b) of International Application Serial No. PCT/US2014/022086, filed Mar. 7, 2014, which claims the benefit of U.S. Provisional Appl. Ser. No. 61/775,029, filed Mar. 8, 2013, each of which are incorporated herein by reference.

INCORPORATION BY REFERENCE OF MATERIAL SUBMITTED ELECTRONICALLY

Incorporated by reference in its entirety is a computer-readable nucleotide/amino acid sequence listing submitted to the United States Patent Office on Oct. 16, 2020 and identified as follows: 30 kilobytes acii (text) file named "U.S. Ser. No. 14/773,482" created on Sep. 28, 2016.

FIELD OF THE DISCLOSURE

The present invention is related to isolated nucleic acids, expression methods, host cells, expression vectors, and DNA constructs for producing proteins, and polypeptides, and to the proteins and the polypeptides produced using the expression methods. More particularly, the invention relates to nucleic acids isolated from *Pichia pastoris* wherein the nucleic acids have promoter activity. The invention also relates to expression methods, host cells, expression vectors, and DNA constructs, for using the *Pichia pastoris* promoters to produce proteins and polypeptides, and to the proteins and the polypeptides produced using the expression methods.

BACKGROUND AND SUMMARY OF THE INVENTION

Yeast expression systems can be used to effectively produce proteins, such as enzymes, hormones, and vaccine proteins, in part, because some yeast grow rapidly to high cell densities, are grown in simple and inexpensive media, and are eukaryotes so they can modify proteins in a manner similar to native proteins in mammals. Additionally, with a proper signal sequence, the expressed protein can be secreted into the culture medium for convenient isolation and purification. Some yeast expression systems are also accepted in the food and pharmaceutical industries as being safe for the production of pharmaceuticals and food products, unlike fungal and bacterial expression systems which may in some cases be unsafe, for example, for human food manufacturing.

Thus, it is beneficial for a variety of industries, such as the food and animal feed industries, the human and animal health industries, and the like, to develop or improve yeast expression systems that can be used to express high levels of proteins to increase yield, reduce the expense of isolation and purification of proteins, and reduce the costs of human and animal health products and food products.

A variety of types of yeast expression systems have been developed involving either the use of inducible or constitutive expression of proteins using nucleic acids encoding homologous or heterologous proteins, under the control of a yeast promoter. Promoters are regulatory elements that are linked to the 5' end of a nucleic acid encoding a protein, and may interact with various regulatory factors in the host cell (e.g., a yeast host cell) to control transcription of RNA from DNA. Promoters may also control the timing of transcription of RNA from DNA. For example, the AOX 1 promoter has been identified in the yeast *Pichia pastoris*, and is commonly used in yeast expression systems because it is a tightly regulated, strong promoter.

Due to the importance of yeast expression systems for a variety of industries, including the human pharmaceuticals industry, and the human food and animal feed industries, the improvement of yeast expression systems is the focus of much research and development. Accordingly, the present inventors have identified promoters from *Pichia pastoris* that are particularly effective for use in expression of proteins in yeast. The promoters described herein can be used, for example, in methanol-inducible yeast expression systems, or in expression systems for the constitutive expression of proteins.

In one illustrative embodiment of the invention, an isolated nucleic acid is provided wherein the sequence of the isolated nucleic acid comprises a sequence, for example, at least 90%, 95%, or 98% identical to a sequence selected from the group consisting of SEQ ID NO:1, SEQ ID NO:2, SEQ ID NO:3, SEQ ID NO:4, SEQ ID NO:5, and SEQ ID NO:6 as described herein, or at least 90%, 95%, or 98% identical to a fragment thereof, wherein the isolated nucleic acid comprises the sequence of a methanol-inducible *Pichia pastoris* promoter. In other embodiments, expression vectors, host cells, and DNA constructs comprising these promoter sequences are provided.

In another embodiment, a method of producing a protein using these promoter sequences is provided. The method comprises the steps of culturing in a culture medium a host cell comprising a first expression cassette comprising any of the above promoter sequences operably linked to a heterologous coding sequence encoding a protein, wherein the culturing is done under conditions permitting expression of the protein. In another illustrative embodiment, an isolated protein produced according to this method is provided.

In one illustrative embodiment of the invention, an isolated nucleic acid is provided wherein the sequence of the isolated nucleic acid comprises a sequence, for example, at least 90%, 95%, or 98% identical to a sequence selected from the group consisting of SEQ ID NO:7, SEQ ID NO:8, SEQ ID NO:9, SEQ ID NO:10, SEQ ID NO:11, SEQ ID NO:12, SEQ ID NO:13, and SEQ ID NO:14 as described herein, or at least 90%, 95%, or 98% identical to a fragment thereof, wherein the isolated nucleic acid comprises the sequence of a constitutive *Pichia pastoris* promoter. In other embodiments, expression vectors, host cells, and DNA constructs comprising these promoter sequences are provided.

In another embodiment, a method of producing a protein using these promoter sequences is provided. The method comprises the steps of culturing in a culture medium a host cell comprising a first expression cassette comprising any of the above promoter sequences operably linked to a heterologous coding sequence encoding a protein, wherein the culturing is done under conditions permitting expression of the protein. In another illustrative embodiment, an isolated protein produced according to this method is provided.

All of the embodiments described in the following clause list are also contemplated for use in accordance with the invention. For all of the embodiments described in the following clauses, any applicable combination of embodiments is considered to be in accordance with the invention.

1. An isolated nucleic acid wherein the sequence of the isolated nucleic acid comprises a sequence at least 90% identical to a sequence selected from the group consisting of SEQ ID NO:1, SEQ ID NO:2, SEQ ID NO:3, SEQ ID NO:4, SEQ ID NO:5, and SEQ ID NO:6, or at least 90% identical to a fragment thereof, wherein the isolated nucleic acid comprises the sequence of a methanol-inducible *Pichia pastoris* promoter.

2. The isolated nucleic acid of clause 1 wherein the sequence of the isolated nucleic acid is at least 95% identical to a sequence selected from the group consisting of SEQ ID NO:1, SEQ ID NO:2, SEQ ID NO:3, SEQ ID NO:4, SEQ ID NO:5, and SEQ ID NO:6, or at least 95% identical to a fragment thereof.

3. The isolated nucleic acid of clause 1 wherein the sequence of the isolated nucleic acid is at least 98% identical to a sequence selected from the group consisting of SEQ ID NO:1, SEQ ID NO:2, SEQ ID NO:3, SEQ ID NO:4, SEQ ID NO:5, and SEQ ID NO:6, or at least 98% identical to a fragment thereof.

4. The isolated nucleic acid sequence of clause 1 wherein the sequence of the isolated nucleic acid is a sequence selected from the group consisting of SEQ ID NO:1, SEQ ID NO:2, SEQ ID NO:3, SEQ ID NO:4, SEQ ID NO:5, and SEQ ID NO:6, or a fragment thereof.

5. The isolated nucleic acid of any one of clauses 1 to 4 operably linked to a heterologous coding sequence.

6. The isolated nucleic acid of clause 5 wherein the heterologous coding sequence encodes a protein selected from the group consisting of a toxin, an antibody, a hormone, an enzyme, a growth factor, a cytokine, a structural protein, an immunogenic protein, and a cell signaling protein.

7. The isolated nucleic acid of clause 6 wherein the protein is an enzyme for use in animal feed.

8. The isolated nucleic acid of clause 7 wherein the protein is selected from the group consisting of a phytase, a mannanase, a galactosidase, an amylase, a glucanase, a protease, a cellulase, and a xylanase.

9. The isolated nucleic acid of clause 8 wherein the protein is a phytase.

10. The isolated nucleic acid of clause 8 wherein the protein is a galactosidase.

11. An expression vector comprising the isolated nucleic acid of any one of clauses 1 to 10.

12. A host cell comprising the expression vector of clause 11.

13. A host cell comprising the isolated nucleic acid of any one of clauses 1 to 10.

14. The host cell of any one of clauses 12 or 13 wherein the host cell is a *Pichia* species.

15. The host cell of clause 14 wherein the *Pichia* species is *Pichia pastoris*.

16. A DNA construct comprising the isolated nucleic acid of any one of clauses 1 to 10.

17. A method of producing a protein, the method comprising the step of
culturing in a culture medium a host cell comprising a first expression cassette comprising the isolated nucleic acid of any one of clauses 1 to 4 operably linked to a heterologous coding sequence encoding a protein, wherein the culturing is done under conditions permitting expression of the protein.

18. The method of clause 17 wherein the protein is selected from the group consisting of a toxin, an antibody, a hormone, an enzyme, a growth factor, a cytokine, a structural protein, an immunogenic protein, and a cell signaling protein.

19. The method of clause 18 wherein the protein is an enzyme for use in animal feed.

20. The method of clause 19 wherein the protein is selected from the group consisting of a phytase, a mannanase, a galactosidase, an amylase, a glucanase, a cellulase, a protease, and a xylanase.

21. The method of clause 20 wherein the protein is a phytase.

22. The method of clause 20 wherein the protein is a galactosidase.

23. The method of any one of clauses 17 to 22 wherein the protein is expressed using the first expression cassette in combination with a second expression cassette.

24. The method of clause 23 wherein the second expression cassette comprises the heterologous coding sequence encoding the protein operably linked to an isolated nucleic acid having a sequence comprising the sequence of SEQ ID NO:15 or SEQ ID NO:16 wherein SEQ ID NO:15 and SEQ ID NO:16 have promoter activity, or any other AOX 1 or AOX 2 promoter sequence.

25. The method of clause 24 wherein the protein is expressed using the first expression cassette, the second expression cassette, and a third expression cassette.

26. The method of clause 25 wherein the third expression cassette comprises the heterologous coding sequence encoding the protein operably linked to an isolated nucleic acid having a sequence at least 90% identical to a sequence selected from the group consisting of SEQ ID NO:1, SEQ ID NO:2, SEQ ID NO:3, SEQ ID NO:4, SEQ ID NO:5, and SEQ ID NO:6, or at least 90% identical to a fragment thereof.

27. The method of clause 23 wherein the second expression cassette comprises the heterologous coding sequence encoding the protein operably linked to an isolated nucleic acid having a sequence at least 90% identical to a sequence selected from the group consisting of SEQ ID NO:1, SEQ ID NO:2, SEQ ID NO:3, SEQ ID NO:4, SEQ ID NO:5, and SEQ ID NO:6, or at least 90% identical to a fragment thereof.

28. An isolated protein produced according to the method of any one of clauses 17 to 27.

29. An isolated nucleic acid wherein the sequence of the isolated nucleic acid comprises a sequence at least 90% identical to a sequence selected from the group consisting of SEQ ID NO:7, SEQ ID NO:8, SEQ ID NO:9, SEQ ID NO:10, SEQ ID NO:11, SEQ ID NO:12, SEQ ID NO:13, and SEQ ID NO:14, or at least 90% identical to a fragment thereof, wherein the nucleic acid comprises the sequence of a constitutive *Pichia pastoris* promoter.

30. The isolated nucleic acid of clause 29 wherein the sequence of the isolated nucleic acid is at least 95% identical to a sequence selected from the group consisting of SEQ ID NO:7, SEQ ID NO:8, SEQ ID NO:9, SEQ ID NO:10, SEQ ID NO:11, SEQ ID NO:12, SEQ ID NO:13, and SEQ ID NO:14 or at least 95% identical to a fragment thereof.

31. The isolated nucleic acid of clause 29 wherein the sequence of the isolated nucleic acid is at least 98% identical to a sequence selected from the group consisting of SEQ ID NO:7, SEQ ID NO:8, SEQ ID NO:9, SEQ ID NO:10, SEQ ID NO: SEQ ID NO: SEQ ID NO:13, and SEQ ID NO: or at least 98% identical to a fragment thereof.

32. The isolated nucleic acid sequence of clause 29 wherein the sequence of the isolated nucleic acid is a sequence selected from the group consisting of SEQ ID NO:7, SEQ ID NO:8, SEQ ID NO:9, SEQ ID NO:10, SEQ ID NO:11, SEQ ID NO:12, SEQ ID NO:13, and SEQ ID NO:14, or a fragment thereof.

33. The isolated nucleic acid of any one of clauses 29 to 32 operably linked to a heterologous coding sequence.

34. The isolated nucleic acid of clause 33 wherein the heterologous coding sequence encodes a protein selected from the group consisting of a toxin, an antibody, a hormone, an enzyme, a growth factor, a cytokine, a structural protein, an immunogenic protein, and a cell signaling protein.

35. The isolated nucleic acid of clause 34 wherein the protein is an enzyme for use in animal feed.

36. The isolated nucleic acid of clause 35 wherein the protein is selected from the group consisting of a phytase, a mannanase, a galactosidase, an amylase, a glucanase, a cellulase, a protease, and a xylanase.

37. The isolated nucleic acid of clause 36 wherein the protein is a phytase.

38. The isolated nucleic acid of clause 36 wherein the protein is a galactosidase.

39. An expression vector comprising the isolated nucleic acid of any one of clauses 29 to 38.

40. A host cell comprising the expression vector of clause 39.

41. A host cell comprising the isolated nucleic acid of any one of clauses 29 to 38.

42. The host cell of any one of clauses 40 or 41 wherein the host cell is a *Pichia* species.

43. The host cell of clause 42 wherein the *Pichia* species is *Pichia pastoris*.

44. A DNA construct comprising the isolated nucleic acid of any one of clauses 29 to 38.

45. A method of producing a protein, the method comprising the step of culturing in a culture medium a host cell comprising a first expression cassette comprising the isolated nucleic acid of any one of clauses 29 to 38 operably linked to a heterologous coding sequence encoding a protein, wherein the culturing is done under conditions permitting expression of the protein.

46. The method of clause 45 wherein the protein is selected from the group consisting of a toxin, an antibody, a hormone, an enzyme, a growth factor, a cytokine, a structural protein, an immunogenic protein, and a cell signaling protein.

47. The method of clause 46 wherein the protein is an enzyme for use in animal feed.

48. The method of clause 47 wherein the protein is selected from the group consisting of a phytase, a mannanase, a galactosidase, an amylase, a glucanase, a cellulase, a protease, and a xylanase.

49. The method of clause 48 wherein the protein is a phytase.

50. The method of clause 48 wherein the protein is a galactosidase.

51. The method of any one of clauses 45 to 50 wherein the protein is expressed using the first expression cassette in combination with a second expression cassette.

52. The method of clause 51 wherein the second expression cassette comprises the heterologous coding sequence encoding the protein operably linked to an isolated nucleic acid having a sequence comprising the sequence of SEQ ID NO:15 or SEQ ID NO:16 wherein SEQ ID NO:15 and SEQ ID NO:16 have promoter activity, or any other AOX 1 or AOX 2 promoter sequence.

53. The method of clause 51 wherein the protein is expressed using the first expression cassette, the second expression cassette, and a third expression cassette.

54. The method of clause 53 wherein the third expression cassette comprises the heterologous coding sequence encoding the protein operably linked to an isolated nucleic acid having a sequence at least 90% identical to a sequence selected from the group consisting of SEQ ID NO:7, SEQ ID NO:8, SEQ ID NO:9, SEQ ID NO:10, SEQ ID NO:11, SEQ ID NO:12, SEQ ID NO:13, or at least 90% identical to a fragment thereof.

55. The method of clause 51 wherein the second expression cassette comprises the heterologous coding sequence encoding the protein operably linked to an isolated nucleic acid having a sequence at least 90% identical to a sequence selected from the group consisting of SEQ ID NO:7, SEQ ID NO:8, SEQ ID NO:9, SEQ ID NO:10, SEQ ID NO:11, SEQ ID NO:12, SEQ ID NO:13, or at least 90% identical to a fragment thereof.

56. An isolated protein produced according to the method of any one of clauses 45 to 55.

57. The host cell of any one of clauses 40 or 41 wherein the host cell is selected from the group consisting of *Hansenula* species, *Pichia* species, *Saccharomyces* species, *Schizosaccharomyces* species, *Torulaspora* species, a *Candida* species, a *Yarrowia* species, and *Kluveromyces* species.

58. A host cell comprising the DNA construct of clause 44 wherein the host cell is selected from the group consisting of *Hansenula* species, *Pichia* species, *Saccharomyces* species, *Schizosaccharomyces* species, *Torulaspora* species, a *Candida* species, a *Yarrowia* species, and *Kluveromyces* species.

59. The method of any one of clauses 45 to 55 wherein the host cell is selected from the group consisting of *Hansenula* species, *Pichia* species, *Saccharomyces* species, *Schizosaccharomyces* species, a *Yarrowia* species, *Torulaspora* species, *Candida* species, and *Kluveromyces* species.

60. The host cell of any one of clauses 12 or 13 wherein the host cell is a methylotrophic yeast.

61. The host cell of clause 60 wherein the host cell is selected from the group consisting of *Hansenula* species, *Pichia* species, and *Candida* species.

62. A host cell comprising the DNA construct of clause 16 wherein the host cell is a methylotrophic yeast.

63. The host cell of clause 62 selected from the group consisting of *Hansenula* species, *Pichia* species, and *Candida* species.

64. The method of any one of clauses 17 to 27 wherein the host cell is a methylotrophic yeast.

65. The method of clause 64 wherein the host cell is selected from the group consisting of *Hansenula* species, *Pichia* species, and *Candida* species.

66. The method of any one of clauses 25 or 53 wherein the third expression cassette comprises the heterologous coding sequence encoding the protein operably linked to an isolated nucleic acid having a sequence of SEQ ID NO:15 or SEQ ID NO:16 wherein SEQ ID NO:15 and SEQ ID NO:16 have promoter activity, or any other AOX 1 or AOX 2 promoter sequence.

67. A method of producing one or more proteins, the method comprising the step of culturing in a culture medium a host cell comprising a first expression cassette, a second expression cassette, and one or more additional expression cassettes, wherein each of the one or more additional expression cassettes comprises the isolated nucleic acid of any one of clauses 1 to 4 operably linked to a heterologous coding sequence encoding the one or more proteins, wherein the culturing is done under conditions permitting expression of the one or more proteins.

68. A method of producing one or more proteins, the method comprising the step of
culturing in a culture medium a host cell comprising a first expression cassette, a second expression cassette, and one or more additional expression cassettes, wherein each of the one or more additional expression cassettes comprises the isolated nucleic acid of any one of clauses 29 to 38 operably linked to a heterologous coding sequence encoding the one or more proteins, wherein the culturing is done under conditions permitting expression of the one or more proteins.

69. The method of any one of clauses 17 or 45 further comprising the step of purifying the protein from the medium of the cultured host cell.

70. The method of any one of clauses 67 or 68 further comprising the step of purifying one or more of the one or more proteins from the medium of the cultured host cell.

71. The isolated nucleic acid, host cell, expression vector, isolated protein, DNA construct, or method of any one of clauses 1 to 70 wherein the isolated nucleic acid consists of any one of SEQ ID NOS. 1 to 14, or a fragment thereof.

72. An isolated nucleic acid consisting of any one of SEQ ID NOS. 1 to 14, or a fragment thereof.

73. The isolated nucleic acid of clause 5 wherein the heterologous coding sequence encodes a protein or a polypeptide selected from the group consisting of a toxin, an antibody, a hormone, an enzyme, a growth factor, a cytokine, a structural protein, an immunogenic protein, and a cell signaling protein.

74. The isolated nucleic acid of clause 29 wherein the heterologous coding sequence encodes a protein or a polypeptide selected from the group consisting of a toxin, an antibody, a hormone, an enzyme, a growth factor, a cytokine, a structural protein, an immunogenic protein, and a cell signaling protein.

75. A method of producing a protein or a polypeptide, the method comprising the step of culturing in a culture medium a host cell comprising a first expression cassette comprising the isolated nucleic acid of any one of clauses 1 to 4 operably linked to a heterologous coding sequence encoding the protein or the polypeptide, wherein the culturing is done under conditions permitting expression of the protein or the polypeptide.

76. A method of producing a protein or a polypeptide, the method comprising the step of culturing in a culture medium a host cell comprising a first expression cassette comprising the isolated nucleic acid of any one of clauses 29 to 38 operably linked to a heterologous coding sequence encoding the protein or the polypeptide, wherein the culturing is done under conditions permitting expression of the protein or the polypeptide.

BRIEF DESCRIPTION OF THE DRAWINGS

FIG. 1 shows the nucleotide sequence of a methanol-inducible promoter, CAM1_(FR839630_178837 . . . 180488)_selection (SEQ ID NO:1).

FIG. 2 shows the nucleotide sequence of a methanol-inducible promoter, PP7435_Chr1-1351_selection (SEQ ID NO:2).

FIG. 3 shows the nucleotide sequence of a methanol-inducible promoter, THI4_selection (SEQ ID NO:3).

FIG. 4 shows the nucleotide sequence of a methanol-inducible promoter, GPM2_selection (SEQ ID NO:4).

FIG. 5 shows the nucleotide sequence of a methanol-inducible promoter, PP7435_Chr2-0790_selection (SEQ ID NO:5).

FIG. 6 shows the nucleotide sequence of a methanol-inducible promoter, PP7435_Chr3-0842_selection (SEQ ID NO:6).

FIG. 7 shows the nucleotide sequence of a constitutive promoter, PP7435_Chr1-0269_selection (SEQ ID NO:7).

FIG. 8 shows the nucleotide sequence of a constitutive promoter, PP7435_Chr2-0207_selection (SEQ ID NO:8).

FIG. 9 shows the nucleotide sequence of a constitutive promoter, PP7435_Chr2-0208_selection (SEQ ID NO:9).

FIG. 10 shows the nucleotide sequence of a constitutive promoter, PP7435_Chr2-0809_selection (SEQ ID NO:10).

FIG. 11 shows the nucleotide sequence of a constitutive promoter, PP7435_Chr4-0069_selection (SEQ ID NO:11).

FIG. 12 shows the nucleotide sequence of a constitutive promoter, PP7435_Chr4-0800_selection (SEQ ID NO:12).

FIG. 13 shows the nucleotide sequence of a constitutive promoter, TEF2_selection *Pichia pastoris* CBS 7435 chromosome 1, complete replicon sequence (SEQ ID NO:13).

FIG. 14 shows the nucleotide sequence of a constitutive promoter, PP7435_Chr3-0476_selection *Pichia pastoris* CBS 7435 chromosome 3, complete replicon sequence (SEQ ID NO:14).

FIG. 15. shows the nucleotide sequence of the AOX1 promoter sequence (SEQ ID NO:15).

FIG. 16. shows the genomic sequence 1000 bp upstream of the AOX1 promoter ATG start codon (SEQ ID NO:16).

FIG. 18 (panels a-c). shows the images of A-gal expression from *Pichia* clones with the reporter plasmid and different promoters.

DETAILED DESCRIPTION OF THE ILLUSTRATIVE EMBODIMENTS

Figure 17:
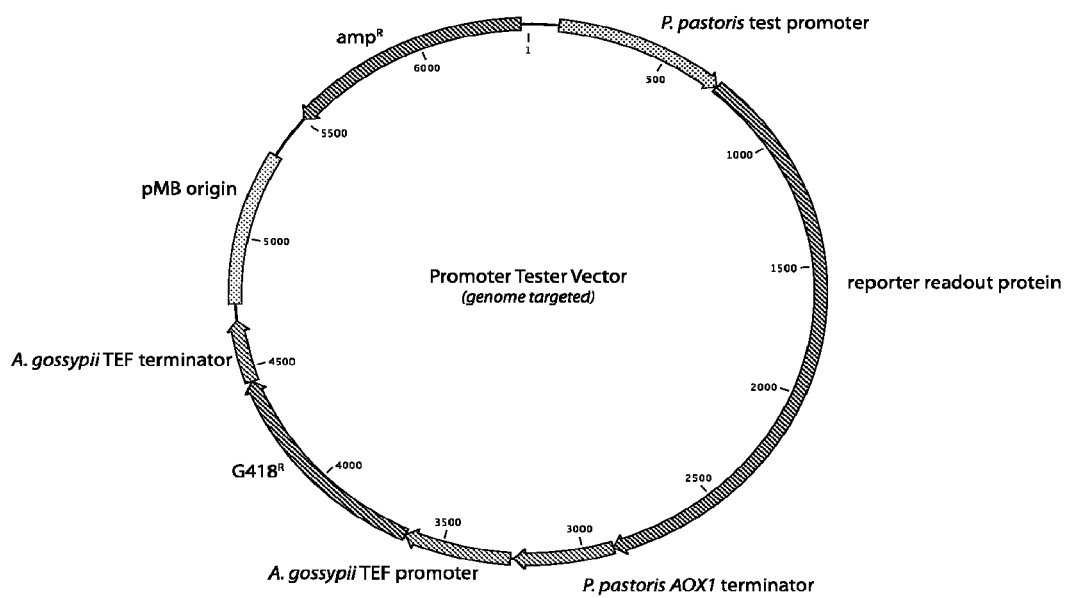
FIG. 17. shows the reporter plasmid for testing expression of alpha-galactosidase (A-gal) with the promoters.

In one illustrative embodiment of the invention, an isolated nucleic acid is provided wherein the sequence of the isolated nucleic acid comprises a sequence, for example, at least 90%, 95%, or 98% identical to a sequence selected from the group consisting of SEQ ID NO:1, SEQ ID NO:2, SEQ ID NO:3, SEQ ID NO:4, SEQ ID NO:5, and SEQ ID NO:6 as described herein, or at least 90%, 95%, or 98% identical to a fragment thereof, wherein the nucleic acid comprises the sequence of a methanol-inducible *Pichia pastoris* promoter. In another embodiment, the isolated nucleic acid sequence is a sequence selected from the group consisting of SEQ ID NO:1, SEQ ID NO:2, SEQ ID NO:3, SEQ ID NO:4, SEQ ID NO:5, and SEQ ID NO:6, or a fragment thereof. In other embodiments, expression vectors, host cells, and DNA constructs comprising these promoter sequences are provided.

In another embodiment, a method of producing a protein using these promoter sequences is provided. The method comprises the steps of culturing in a culture medium a host cell comprising a first expression cassette comprising any of the above promoter sequences operably linked to a heterologous coding sequence encoding a protein, wherein the culturing is done under conditions permitting expression of the protein. In another illustrative embodiment, an isolated protein produced according to this method is provided.

In one illustrative embodiment of the invention, an isolated nucleic acid is provided wherein the sequence of the isolated nucleic acid comprises a sequence, for example, at least 90%, 95%, or 98% identical to a sequence selected from the group consisting of SEQ ID NO:7, SEQ ID NO:8, SEQ ID NO:9, SEQ ID NO:10, SEQ ID NO:11, SEQ ID NO:12, SEQ ID NO:13, and SEQ ID NO:14 as described herein, or at least 90%, 95%, or 98% identical to a fragment thereof, wherein the nucleic acid comprises the sequence of a constitutive *Pichia pastoris* promoter. In another embodiment, the isolated nucleic acid sequence is a sequence selected from the group consisting of SEQ ID NO:7, SEQ ID NO:8, SEQ ID NO:9, SEQ ID NO:10, SEQ ID NO:11, SEQ ID NO:12, SEQ ID NO:13, and SEQ ID NO:14, or a fragment thereof. In other embodiments, expression vectors, host cells, and DNA constructs comprising these promoter sequences are provided. The above-described promoters have been isolated from a yeast strain (i.e., NRRL Y11430) currently classified as a *Pichia pastoris* yeast strain. However, the classification may change at some point to a *Komagataella* species (e.g., *Komagataella phaffii*).

In another embodiment, a method of producing a protein using any of the promoter sequences in the preceding paragraph is provided. The method comprises the steps of culturing in a culture medium a host cell comprising a first expression cassette comprising any of the above promoter sequences operably linked to a heterologous coding sequence encoding a protein, wherein the culturing is done under conditions permitting expression of the protein. In another illustrative embodiment, an isolated protein produced according to this method is provided.

All of the embodiments described in the following clause list are contemplated for use in accordance with the invention. For all of the embodiments described in the following clauses, any applicable combination of embodiments is considered to be in accordance with the invention. Any embodiment described in the following clause list is also contemplated for use with any embodiment described in the Summary of Invention section of this application or in the Detailed Description of the Illustrative Embodiments section of this application.

1. An isolated nucleic acid wherein the sequence of the isolated nucleic acid comprises a sequence at least 90% identical to a sequence selected from the group consisting of SEQ ID NO:1, SEQ ID NO:2, SEQ ID NO:3, SEQ ID NO:4, SEQ ID NO:5, and SEQ ID NO:6, or at least 90% identical to a fragment thereof, wherein the isolated nucleic acid comprises the sequence of a methanol-inducible *Pichia pastoris* promoter.

2. The isolated nucleic acid of clause 1 wherein the sequence of the isolated nucleic acid is at least 95% identical to a sequence selected from the group consisting of SEQ ID NO:1, SEQ ID NO:2, SEQ ID NO:3, SEQ ID NO:4, SEQ ID NO:5, and SEQ ID NO:6, or at least 95% identical to a fragment thereof.

3. The isolated nucleic acid of clause 1 wherein the sequence of the isolated nucleic acid is at least 98% identical to a sequence selected from the group consisting of SEQ ID NO:1, SEQ ID NO:2, SEQ ID NO:3, SEQ ID NO:4, SEQ ID NO:5, and SEQ ID NO:6, or at least 98% identical to a fragment thereof.

4. The isolated nucleic acid sequence of clause 1 wherein the sequence of the isolated nucleic acid is a sequence selected from the group consisting of SEQ ID NO:1, SEQ ID NO:2, SEQ ID NO:3, SEQ ID NO:4, SEQ ID NO:5, and SEQ ID NO:6, or a fragment thereof.

5. The isolated nucleic acid of any one of clauses 1 to 4 operably linked to a heterologous coding sequence.

6. The isolated nucleic acid of clause 5 wherein the heterologous coding sequence encodes a protein selected from the group consisting of a toxin, an antibody, a hormone, an enzyme, a growth factor, a cytokine, a structural protein, an immunogenic protein, and a cell signaling protein.

7. The isolated nucleic acid of clause 6 wherein the protein is an enzyme for use in animal feed.

8. The isolated nucleic acid of clause 7 wherein the protein is selected from the group consisting of a phytase, a mannanase, a galactosidase, an amylase, a glucanase, a protease, a cellulase, and a xylanase.

9. The isolated nucleic acid of clause 8 wherein the protein is a phytase.

10. The isolated nucleic acid of clause 8 wherein the protein is a galactosidase.

11. An expression vector comprising the isolated nucleic acid of any one of clauses 1 to 10.

12. A host cell comprising the expression vector of clause 11.

13. A host cell comprising the isolated nucleic acid of any one of clauses 1 to 10.

14. The host cell of any one of clauses 12 or 13 wherein the host cell is a *Pichia* species.

15. The host cell of clause 14 wherein the *Pichia* species is *Pichia pastoris*.

16. A DNA construct comprising the isolated nucleic acid of any one of clauses 1 to 10.

17. A method of producing a protein, the method comprising the step of
culturing in a culture medium a host cell comprising a first expression cassette comprising the isolated nucleic acid of any one of clauses 1 to 4 operably linked to a heterologous coding sequence encoding a protein, wherein the culturing is done under conditions permitting expression of the protein.

18. The method of clause 17 wherein the protein is selected from the group consisting of a toxin, an antibody, a hormone, an enzyme, a growth factor, a cytokine, a structural protein, an immunogenic protein, and a cell signaling protein.

19. The method of clause 18 wherein the protein is an enzyme for use in animal feed.

20. The method of clause 19 wherein the protein is selected from the group consisting of a phytase, a mannanase, a galactosidase, an amylase, a glucanase, a cellulase, a protease, and a xylanase.

21. The method of clause 20 wherein the protein is a phytase.

22. The method of clause 20 wherein the protein is a galactosidase.

23. The method of any one of clauses 17 to 22 wherein the protein is expressed using the first expression cassette in combination with a second expression cassette.

24. The method of clause 23 wherein the second expression cassette comprises the heterologous coding sequence encoding the protein operably linked to an isolated nucleic acid having a sequence comprising the sequence of SEQ ID NO:15 or SEQ ID NO:16 wherein SEQ ID NO:15 and SEQ ID NO:16 have promoter activity, or any other AOX 1 or AOX 2 promoter sequence.

25. The method of clause 24 wherein the protein is expressed using the first expression cassette, the second expression cassette, and a third expression cassette.

26. The method of clause 25 wherein the third expression cassette comprises the heterologous coding sequence encoding the protein operably linked to an isolated nucleic acid having a sequence at least 90% identical to a sequence selected from the group consisting of SEQ ID NO:1, SEQ ID NO:2, SEQ ID NO:3, SEQ ID NO:4, SEQ ID NO:5, and SEQ ID NO:6, or at least 90% identical to a fragment thereof.

27. The method of clause 23 wherein the second expression cassette comprises the heterologous coding sequence encoding the protein operably linked to an isolated nucleic acid having a sequence at least 90% identical to a sequence selected from the group consisting of SEQ ID NO:1, SEQ ID NO:2, SEQ ID NO:3, SEQ ID NO:4, SEQ ID NO:5, and SEQ ID NO:6, or at least 90% identical to a fragment thereof.

28. An isolated protein produced according to the method of any one of clauses 17 to 27.

29. An isolated nucleic acid wherein the sequence of the isolated nucleic acid comprises a sequence at least 90% identical to a sequence selected from the group consisting of SEQ ID NO:7, SEQ ID NO:8, SEQ ID NO:9, SEQ ID NO:10, SEQ ID NO:11, SEQ ID NO:12, SEQ ID NO:13, and SEQ ID NO:14, or at least 90% identical to a fragment thereof, wherein the nucleic acid comprises the sequence of a constitutive *Pichia pastoris* promoter.

30. The isolated nucleic acid of clause 29 wherein the sequence of the isolated nucleic acid is at least 95% identical to a sequence selected from the group consisting of SEQ ID NO:7, SEQ ID NO:8, SEQ ID NO:9, SEQ ID NO:10, SEQ ID NO:11, SEQ ID NO:12, SEQ ID NO:13, and SEQ ID NO:14 or at least 95% identical to a fragment thereof.

31. The isolated nucleic acid of clause 29 wherein the sequence of the isolated nucleic acid is at least 98% identical to a sequence selected from the group consisting of SEQ ID NO:7, SEQ ID NO:8, SEQ ID NO:9, SEQ ID NO:10, SEQ ID NO:11, SEQ ID NO:12, SEQ ID NO:13, and SEQ ID NO:14 or at least 98% identical to a fragment thereof.

32. The isolated nucleic acid sequence of clause 29 wherein the sequence of the isolated nucleic acid is a sequence selected from the group consisting of SEQ ID NO:7, SEQ ID NO:8, SEQ ID NO:9, SEQ ID NO:10, SEQ ID NO:11, SEQ ID NO:12, SEQ ID NO:13, and SEQ ID NO:14, or a fragment thereof. 33. The isolated nucleic acid of any one of clauses 29 to 32 operably linked to a heterologous coding sequence.

34. The isolated nucleic acid of clause 33 wherein the heterologous coding sequence encodes a protein selected from the group consisting of a toxin, an antibody, a hormone, an enzyme, a growth factor, a cytokine, a structural protein, an immunogenic protein, and a cell signaling protein.

35. The isolated nucleic acid of clause 34 wherein the protein is an enzyme for use in animal feed.

36. The isolated nucleic acid of clause 35 wherein the protein is selected from the group consisting of a phytase, a mannanase, a galactosidase, an amylase, a glucanase, a cellulase, a protease, and a xylanase.

37. The isolated nucleic acid of clause 36 wherein the protein is a phytase.

38. The isolated nucleic acid of clause 36 wherein the protein is a galactosidase.

39. An expression vector comprising the isolated nucleic acid of any one of clauses 29 to 38.

40. A host cell comprising the expression vector of clause 39.

41. A host cell comprising the isolated nucleic acid of any one of clauses 29 to 38.

42. The host cell of any one of clauses 40 or 41 wherein the host cell is a *Pichia* species.

43. The host cell of clause 42 wherein the *Pichia* species is *Pichia pastoris*.

44. A DNA construct comprising the isolated nucleic acid of any one of clauses 29 to 38.

45. A method of producing a protein, the method comprising the step of culturing in a culture medium a host cell comprising a first expression cassette comprising the isolated nucleic acid of any one of clauses 29 to 38 operably linked to a heterologous coding sequence encoding a protein, wherein the culturing is done under conditions permitting expression of the protein.

46. The method of clause 45 wherein the protein is selected from the group consisting of a toxin, an antibody, a hormone, an enzyme, a growth factor, a cytokine, a structural protein, an immunogenic protein, and a cell signaling protein.

47. The method of clause 46 wherein the protein is an enzyme for use in animal feed.

48. The method of clause 47 wherein the protein is selected from the group consisting of a phytase, a mannanase, a galactosidase, an amylase, a glucanase, a cellulase, a protease, and a xylanase.

49. The method of clause 48 wherein the protein is a phytase.

50. The method of clause 48 wherein the protein is a galactosidase.

51. The method of any one of clauses 45 to 50 wherein the protein is expressed using the first expression cassette in combination with a second expression cassette.

52. The method of clause 51 wherein the second expression cassette comprises the heterologous coding sequence encoding the protein operably linked to an isolated nucleic acid having a sequence comprising the sequence of SEQ ID NO:15 or SEQ ID NO:16 wherein SEQ ID NO:15 and SEQ ID NO:16 have promoter activity, or any other AOX 1 or AOX 2 promoter sequence.

53. The method of clause 51 wherein the protein is expressed using the first expression cassette, the second expression cassette, and a third expression cassette.

54. The method of clause 53 wherein the third expression cassette comprises the heterologous coding sequence encoding the protein operably linked to an isolated nucleic acid having a sequence comprising a sequence at least 90% identical to a sequence selected from the group consisting of SEQ ID NO:7, SEQ ID NO:8, SEQ ID NO:9, SEQ ID NO:10, SEQ ID NO:11, SEQ ID NO:12, SEQ ID NO:13, or at least 90% identical to a fragment thereof.

55. The method of clause 51 wherein the second expression cassette comprises the heterologous coding sequence encoding the protein operably linked to an isolated nucleic acid having a sequence comprising a sequence at least 90% identical to a sequence selected from the group consisting of SEQ ID NO:7, SEQ ID NO:8, SEQ ID NO:9, SEQ ID NO:10, SEQ ID NO:11, SEQ ID NO:12, SEQ ID NO:13, or at least 90% identical to a fragment thereof.

56. An isolated protein produced according to the method of any one of clauses 45 to 55.

57. The host cell of any one of clauses 40 or 41 wherein the host cell is selected from the group consisting of *Hansenula* species, *Pichia* species, *Saccharomyces* species, *Schizosaccharomyces* species, *Torulaspora* species, a *Candida* species, a *Yarrowia* species, and *Kluveromyces* species.

58. A host cell comprising the DNA construct of clause 44 wherein the host cell is selected from the group consisting of *Hansenula* species, *Pichia* species, *Saccharomyces* species, *Schizosaccharomyces* species, *Torulaspora* species, a *Candida* species, a *Yarrowia* species, and *Kluveromyces* species.

59. The method of any one of clauses 45 to 55 wherein the host cell is selected from the group consisting of *Hansenula* species, *Pichia* species, *Saccharomyces* species, *Schizosaccharomyces* species, *Torulaspora* species, *Candida* species, a *Yarrowia* species, and *Kluveromyces* species.

60. The host cell of any one of clauses 12 or 13 wherein the host cell is a methylotrophic yeast.

61. The host cell of clause 60 wherein the host cell is selected from the group consisting of *Hansenula* species, *Pichia* species, and *Candida* species.

62. A host cell comprising the DNA construct of clause 16 wherein the host cell is a methylotrophic yeast.

63. The host cell of clause 62 selected from the group consisting of *Hansenula* species, *Pichia* species, and *Candida* species.

64. The method of any one of clauses 17 to 27 wherein the host cell is a methylotrophic yeast.

65. The method of clause 64 wherein the host cell is selected from the group consisting of *Hansenula* species, *Pichia* species, and *Candida* species.

66. The method of any one of clauses 25 or 53 wherein the third expression cassette comprises the heterologous coding sequence encoding the protein operably linked to an isolated nucleic acid having a sequence comprising the sequence of SEQ ID NO:15 or SEQ ID NO:16 wherein SEQ ID NO:15 and SEQ ID NO:16 have promoter activity, or any other AOX 1 or AOX 2 promoter sequence.

67. A method of producing one or more proteins, the method comprising the step of culturing in a culture medium a host cell comprising a first expression cassette, a second expression cassette, and one or more additional expression cassettes, wherein each of the one or more additional expression cassettes comprises the isolated nucleic acid of any one of clauses 1 to 4 operably linked to a heterologous coding sequence encoding the one or more proteins, wherein the culturing is done under conditions permitting expression of the one or more proteins.

68. A method of producing one or more proteins, the method comprising the step of culturing in a culture medium a host cell comprising a first expression cassette, a second expression cassette, and one or more additional expression cassettes, wherein each of the one or more additional expression cassettes comprises the isolated nucleic acid of any one of clauses 29 to 38 operably linked to a heterologous coding sequence encoding the one or more proteins, wherein the culturing is done under conditions permitting expression of the one or more proteins.

69. The method of any one of clauses 17 or 45 further comprising the step of purifying the protein from the medium of the cultured host cell.

70. The method of any one of clauses 67 or 68 further comprising the step of purifying one or more of the one or more proteins from the medium of the cultured host cell.

71. The isolated nucleic acid, host cell, expression vector, isolated protein, DNA construct, or method of any one of clauses 1 to 70 wherein the isolated nucleic acid consists of any one of SEQ ID NOS. 1 to 14, or a fragment thereof.

72. An isolated nucleic acid consisting of any one of SEQ ID NOS. 1 to 14, or a fragment thereof.

The phrase "consists of" or "consisting of" means that the sequence specified by the SEQ ID NO. has no additional nucleotide sequences other than those corresponding to the SEQ ID NO.

73. The isolated nucleic acid of clause 5 wherein the heterologous coding sequence encodes a protein or a polypeptide selected from the group consisting of a toxin, an antibody, a hormone, an enzyme, a growth factor, a cytokine, a structural protein, an immunogenic protein, and a cell signaling protein.

74. The isolated nucleic acid of clause 29 wherein the heterologous coding sequence encodes a protein or a polypeptide selected from the group consisting of a toxin, an antibody, a hormone, an enzyme, a growth factor, a cytokine, a structural protein, an immunogenic protein, and a cell signaling protein.

75. A method of producing a protein or a polypeptide, the method comprising the step of
culturing in a culture medium a host cell comprising a first expression cassette comprising the isolated nucleic acid of any one of clauses 1 to 4 operably linked to a heterologous coding sequence encoding the protein or the polypeptide, wherein the culturing is done under conditions permitting expression of the protein or the polypeptide.

76. A method of producing a protein or a polypeptide, the method comprising the step of culturing in a culture medium a host cell comprising a first expression cassette comprising the isolated nucleic acid of any one of clauses 29 to 38 operably linked to a heterologous coding sequence encoding the protein or the polypeptide, wherein the culturing is done under conditions permitting expression of the protein or the polypeptide.

Any yeast expression system known to those skilled in the art can be used in accordance with the present invention. For example, various yeast expression systems are described in U.S. Pat. Nos. 6,451,572, 6,841,370, 6,974,690, 7,320,876, 7,078,035, 7,138,260, and PCT Publication No. WO 2007/112739, all incorporated herein by reference. In any of the embodiments described herein, any of these yeast expression systems can be used. Alternatively, any yeast species or yeast expression system suitable for expression of a protein can be used including yeast species, such as *Saccharomyces* species (e.g., *Saccharomyces cerevisiae*), *Kluyveromyces* species (e.g., *Kluyveromyces lactis*), *Torulaspora* species, *Yarrowia* species (e.g., *Yarrowia lipolitica*), *Schizosaccharomyces* species (e.g., *Schizosaccharomyces pombe*). In another embodiment, methylotrophic yeast species such as *Pichia* species (e.g., *Pichia pastoris* or *Pichia methanolica*), *Hansenula* species (e.g., *Hansenula polymorpha*), *Torulopsis* species, *Komagataella* species, *Candida* species (e.g., *Candida boidinii*), and *Karwinskia* species can be used, in particular when the promoter is a methanol-inducible promoter. In one embodiment the protein can be expressed in the methylotrophic yeast *Pichia pastoris*. Methylotrophic yeast are capable of utilizing methanol as a sole carbon source for the production of the energy resources necessary to maintain cellular function. Methylotrophic yeast contain genes encoding enzymes for methanol utilization such as the genes encoding alcohol oxidase. Any of these host cells can be a host cell strain that is heterologous to the promoter described herein (i.e., the host cell does not normally contain in nature the promoter described herein).

A yeast expression system can be used to produce a sufficient amount of the protein intracellularly, or secreted from the yeast cells so that the protein can be conveniently isolated and purified from the culture medium. As used herein, the term "expression" means transcription and/or translation of a nucleic acid in a host cell. A yeast expression system may include, but is not limited to, the yeast host cell and the expression vector (e.g., a DNA construct) used to express the protein. The expression vector can contain a promoter described herein and, as is known in the art, the promoter is heterologous to the expression vector (i.e., the combination does not occur in nature). In one embodiment, secretion of the protein into the culture medium is controlled by a signal peptide (e.g., the yeast α-factor signal peptide, the yeast KILM1 signal peptide, the yeast PHO1 signal peptide, or the yeast SUC2 signal peptide) incorporated into the expression vector and which is capable of directing the secretion of the expressed protein out of the yeast cell. In other embodiments, other signal peptides suitable for facilitating secretion of the protein from yeast cells are known to those skilled in the art. In one aspect, the signal peptide is typically cleaved from the protein after secretion.

In various embodiments, any expression vector known to the skilled artisan (e.g., a vector that replicates autonomously or integrates into the host genome) and compatible with a yeast expression system can be used. As used herein, the term "vector" means any plasmid, or other vector, in double-stranded or single-stranded form or in linear or circular form that can transform a yeast cell by integration into the yeast cell genome or by existing extrachromosomally (e.g., an autonomously replicating plasmid). As is known in the art, a vector (e.g., expression vector or expression cassette) is a nucleic acid construct used to transform a host cell for expression of a protein, polypeptide, or peptide and the vector is not found in nature in the host cell it transforms.

In one embodiment, the expression vector has restriction endonuclease cleavage sites for the insertion of DNA fragments (e.g., one or more cloning sites and/or a multiple cloning site), and genetic markers for selection of transformants. For example, the genetic markers for selection of transformants can include a selection marker that allows a transformed yeast to grow on a medium devoid of a necessary nutrient that cannot be produced by a deficient strain, a selection marker that encodes an enzyme for which chromogenic substrates are known, or a selection marker that provides resistance to a drug, including, but not limited to, G418, Nourseothricin (Nat), Zeocin, Blasticidin, or Hygromycin. In another embodiment, the expression vector has a terminator sequence for transcription termination (e.g., the AOX 1 or HSP150 terminator). In another embodiment, the expression vector has a 3' untranslated region downstream from the protein coding sequence with a polyadenylation site. As used herein, "3' untranslated region" means nucleotide sequences that are not translated into protein and are located downstream from a coding sequence for a protein. Typically, a 3' untranslated region includes regulatory sequences for mRNA processing. In another embodiment, the expression vector has an origin of replication (e.g., a bacterial origin of replication) for use in synthesizing and amplifying the vector, for example, in a bacterial host. Various expression vectors are described in U.S. Pat. Nos. 6,451,572, 6,841,370, 6,974,690, 7,320,876, 7,078,035, 7,138,260, and PCT Publication No. WO 2007/112739, all incorporated herein by reference. The construction and use of expression vectors is described in Sambrook et al., "Molecular Cloning: A Laboratory Manual", 3rd Edition, Cold Spring Harbor Laboratory Press, (2001), incorporated herein by reference. In another embodiment, the expression vector, or a fragment thereof, can be synthesized de novo or PCR can be used to amplify and join sections of expression vectors.

As used herein, "regulatory sequences" means nucleotide sequences that are typically upstream or downstream from the 5' or 3' end, respectively, of a protein coding sequence. Regulatory sequences are not translated into protein. Regulatory sequences include, but are not limited to, sequences that affect RNA processing or stability, such as polyadenylation signal sequences, enhancers, repressor binding sites, and promoters.

In one embodiment, the protein coding sequence can be operably linked in the expression vector to the promoter sequence capable of directing the expression of the protein, for example, in yeast. As used herein, "operably linked" means functionally linked. As described herein, the promoter can be a constitutive or an inducible promoter, such as a methanol inducible promoter. As used herein, a "constitutive promoter" means a promoter that regulates expression of a gene of interest. The term "constitutive promoter" is known in the art. As used herein, an "inducible promoter" means a regulated promoter that is turned on in a cell by an external stimulus, such as a chemical, light, a change in temperature, a change in cell density, or a protein, such as a hormone. A methanol inducible promoter can have some constitutive activity, although a methanol inducible promoter has maximal activity when induced in the presence of methanol. Likewise, a constitutive promoter can have some inducible activity, but a "constitutive promoter" as used herein does not have maximal activity when induced in the presence of methanol.

As used herein "promoter" means a nucleotide sequence typically located upstream from the 5' end of a coding sequence for a protein that controls the transcription of RNA from DNA, in part, by interacting with various regulatory factors that control transcription. In one embodiment, the promoter may be derived from the same species of yeast as the yeast host cell used for protein expression. In another embodiment, the promoter may be derived from a different yeast species than the yeast host cell used for protein expression. In one embodiment, a promoter may include a TATA box sequence that acts as a recognition site to direct initiation of transcription, including, but not limited to one or more transcriptional enhancer elements. The enhancer elements may be proximal or distal to the TATA box sequence and may be in a normal 5' to 3' orientation or may be in a 3' to 5' orientation. In another embodiment, an enhancer element may be an enhancer element native to the promoter sequence or it may be a heterologous enhancer element inserted into the expression vector construct. An "enhancer element" as used herein is a regulatory element that can stimulate promoter activity.

In various illustrative embodiments described herein, the promoter can be an isolated nucleic acid wherein the sequence of the isolated nucleic acid comprises a sequence at least 80%, at least 85%, at least 90%, at least 92%, at least 95%, at least 96%, at least 97%, at least 98%, or at least 99% identical to a sequence selected from the group consisting of SEQ ID NO:1, SEQ ID NO:2, SEQ ID NO:3, SEQ ID NO:4, SEQ ID NO:5, and SEQ ID NO:6, or at least 80%, at least 85%, at least 90%, at least 92%, at least 95%, at least 96%, at least 97%, at least 98%, or at least 99% identical to a fragment thereof, wherein the isolated nucleic acid comprises the sequence of a methanol-inducible *Pichia pastoris* promoter. In another embodiment, the isolated nucleic acid sequence is a sequence selected from the group consisting of SEQ ID NO:1, SEQ ID NO:2, SEQ ID NO:3, SEQ ID NO:4, SEQ ID NO:5, and SEQ ID NO:6, or a fragment thereof wherein the isolated nucleic acid comprises the sequence of a methanol-inducible *Pichia pastoris* promoter.

In other embodiments, the promoter can be an isolated nucleic acid wherein the sequence of the isolated nucleic acid comprises a sequence at least 80%, at least 85%, at least 90%, at least 92%, at least 95%, at least 96%, at least 97%, at least 98%, or at least 99% identical to a sequence selected from the group consisting of SEQ ID NO:7, SEQ ID NO:8, SEQ ID NO:9, SEQ ID NO:10, SEQ ID NO:11, SEQ ID NO:12, SEQ ID NO:13, and SEQ ID NO:14 or at least 80%, at least 85%, at least 90%, at least 92%, at least 95%, at least 96%, at least 97%, at least 98%, or at least 99% identical to a fragment thereof, wherein the isolated nucleic acid comprises the sequence of a constitutive *Pichia pastoris* promoter. In another embodiment, the isolated nucleic acid sequence is a sequence selected from the group consisting of SEQ ID NO:7, SEQ ID NO:8, SEQ ID NO:9, SEQ ID NO:10, SEQ ID NO:11, SEQ ID NO:12, SEQ ID NO:13, and SEQ ID NO:14, or a fragment thereof wherein the isolated nucleic acid comprises the sequence of a constitutive *Pichia pastoris* promoter.

As used herein "an isolated nucleic acid" means a nucleic acid that is substantially free of sequences that naturally flank the nucleic acid in the genomic DNA of the organism from which the nucleic acid is derived. For example, in various embodiments, an isolated nucleic acid in accordance with the invention can contain less than about 2 kb, less than about 1 kb, less than about 0.5 kb, less than about 0.1 kb of nucleotide sequences, less than about 0.05 kb, or no nucleotide sequences that naturally flank the nucleic acid molecule in genomic DNA of the organism from which the isolated nucleic acid is derived.

As used herein, "a fragment thereof" when referring to the isolated nucleic acid molecule means a fragment of the isolated nucleic acid of SEQ ID NOS: 1 to 14. In various illustrative embodiments, the fragment can be about 50 nucleotides in length, about 100 nucleotides in length, about 200 nucleotides in length, about 300 nucleotides in length, about 400 nucleotides in length, about 500 nucleotides in length, about 600 nucleotides in length, about 700 nucleotides in length, about 800 nucleotides in length, or about 900 nucleotides in length. In other embodiments, the fragment can extend about 50 nucleotides, about 100 nucleotides, about 200 nucleotides, about 300 nucleotides, about 400 nucleotides, about 500 nucleotides, about 600 nucleotides, about 700 nucleotides, about 800 nucleotides, or about 900 nucleotides upstream from the 3' end of the isolated nucleic acid of any of SEQ ID NOS: 1 to 14. In yet other embodiments, the fragment can include about 50 nucleotides, about 100 nucleotides, about 200 nucleotides, about 300 nucleotides, or about 350 nucleotides upstream and/or downstream from the TATA box sequence found in each of SEQ ID NOS: 1 to 14.

In various embodiments, the isolated nucleic acids described herein may be purified by techniques for purification of nucleic acids (e.g., DNA) that are well-known in the art. For example, the nucleic acids may be separated from contaminants by physical methods including, but not limited to, centrifugation, pressure techniques, or by using a substance with affinity for nucleic acids (e.g., DNA), such as, for example, silica beads. After sufficient washing, the isolated nucleic acids may be suspended in either water or a buffer. In other embodiments, commercial kits are available, such as Qiagen™, Nuclisensm™, and Wizard™ (Promega), and Promegam™. Methods for purifying nucleic acids are described in Sambrook et al., "Molecular Cloning: A Laboratory Manual", 3rd Edition, Cold Spring Harbor Laboratory Press, (2001), incorporated herein by reference. An isolated nucleic acid as described herein may be an isolated nucleic acid that is also purified, or the isolated nucleic acid may be impure. A "purified nucleic acid" is substantially free of other cellular material, or culture medium when produced by recombinant techniques, or substantially free of chemical precursors or other chemicals when chemically synthesized.

The isolated nucleic acids described herein are capable of specific hybridization, under appropriate hybridization conditions (e.g., appropriate buffer, ionic strength, temperature, formamide, and MgCl$_2$ concentrations), to a complementary nucleic acid. The isolated nucleic acids described herein can be modified by substitution, deletion, truncation, and/or can be fused with other nucleic acid molecules wherein the resulting isolated nucleic acids hybridize specifically to the complemetary nucleic acids.

Also within the scope of the invention are nucleic acids complementary to the isolated nucleic acids, or fragments thereof, described herein, and those that hybridize to the isolated nucleic acids described herein or those that hybridize to their complements under highly stringent conditions. As used herein, the term "complementary" refers to the ability of purine and pyrimidine nucleotide sequences to associate through hydrogen bonding to form double-stranded nucleic acid molecules. Guanine and cytosine, adenine and thymine, and adenine and uracil are complementary and can associate through hydrogen bonding resulting in the formation of double-stranded nucleic acid molecules when two nucleic acid molecules have "complementary" sequences. The complementary DNA sequences are referred to as a "complement."

In accordance with the invention "highly stringent conditions" means hybridization at 65° C. in 5×SSPE and 50% formamide, and washing at 65° C. in 0.5×SSPE. Conditions for high stringency hybridization are described in Sambrook et al., "Molecular Cloning: A Laboratory Manual", 3rd Edition, Cold Spring Harbor Laboratory Press, (2001), incorporated herein by reference. In some illustrative aspects, hybridization can occur along the full-length of the isolated nucleic acid, or along part of its length, or to a fragment thereof.

Also included are isolated nucleic acid molecules having about 60%, about 70%, about 75%, about 80%, about 85%, about 90%, about 92%, about 95%, 96%, 97%, 98%, and 99% identity to the isolated nucleic acids described herein, or to a fragment thereof. Determination of percent identity or similarity between sequences can be done, for example, by using the GAP program (Genetics Computer Group, software; now available via Accelrys on http://www.accelrys.com), and alignments can be done using, for example, the ClustalW algorithm (VNTI software, InforMax Inc.). A sequence database can be searched using the isolated nucleic acid sequence of interest, or the sequence of a fragment thereof. Algorithms for database searching are typically based on the BLAST software (Altschul et al., 1990). In some embodiments, the percent identity can be determined along the full-length of the isolated nucleic acid.

Techniques for synthesizing the isolated nucleic acids described herein are well-known in the art and include chemical syntheses and recombinant methods. Such techniques are described in Sambrook et al., "Molecular Cloning: A Laboratory Manual", 3rd Edition, Cold Spring Harbor Laboratory Press, (2001), incorporated herein by reference. Isolated nucleic acid molecules can also be made commercially. Techniques for synthesizing the isolated nucleic acids described herein are well-known in the art. The isolated nucleic acids described herein can be analyzed by techniques known in the art, such as restriction enzyme analysis or sequencing, to determine the sequence of the isolated nucleic acids. Thus, isolated nucleic acids described herein may be synthetic.

In illustrative aspects, yeast cells are transformed with an expression vector comprising a heterologous nucleic acid encoding the protein of interest operably linked to one of the promoters described herein using procedures well-known to those skilled in the art. The term "transformation" means the transfer of a nucleic acid, or a nucleic acid fragment, into a host cell. In illustrative embodiments, such transformation protocols include electroporation, lithium acetate methods, and use of spheroplasts. In illustrative aspects, the expressed nucleic acid coding sequence can be a heterologous nucleic acid coding sequence. As used herein, a heterologous coding sequence is defined as an artificial or synthetic nucleic acid or a nucleic acid originating from a different species than the species from which the promoter sequence was derived. Thus, a heterologous coding sequence linked to a promoter described herein does not occur in nature.

In various embodiments, the transformed yeast cells may be grown by techniques including batch and continuous fermentation in a liquid medium or on a semi-solid medium, or a solid medium. Typically, "conditions permitting expression of the protein" as used herein means conditions for batch or continuous fermentation of yeast in a liquid medium, but growth on a semi-solid medium, such as agar, is not excluded. Culture media for yeast cells are known in the art and are typically supplemented with a carbon source (e.g., glucose). A typical yeast culture medium is YPD broth (Sunrise Science Products, Inc.) comprising yeast extract (10 grams), Bacto peptone (20 grams), and dextrose (20 grams). In one illustrative aspect, the transformed yeast cells can be grown aerobically at 30° C. in a controlled pH environment (a pH of about 6) and with the carbon source (e.g., glucose) maintained continuously at a predetermined level known to support growth of the yeast cells to a desired density within a specific period of time.

In one illustrative embodiment, a method of producing a protein is provided. The method comprises the step of culturing in a culture medium a host cell comprising a first expression cassette comprising an isolated nucleic acid of any one of SEQ ID NOS: 1 to 14, or a fragment thereof, operably linked to a heterologous coding sequence encoding a protein, wherein the culturing is done under conditions permitting expression of the protein. The method can further comprise the step of purifying the protein from the medium of the cultured host cell. As used herein, an "expression cassette" means the elements of an expression vector that direct the yeast cell to make RNA. An expression cassette comprises at least regulatory sequences (e.g., a promoter) and a coding sequence for the RNA and protein (i.e., an open reading frame). The isolated nucleic acid can be at least 80%, at least 85%, at least 90%, 92%, 95%, 96%, 97%, 98%, or 99% homologous to the isolated nucleic acid of any of SEQ ID NOS: 1 to 14, or a fragment thereof. In various illustrative aspects, the protein coding sequence can be from a bacterium, a yeast, a fungus, or a virus.

In this method embodiment, the protein can be expressed using the first expression cassette in combination with a second expression cassette. In another embodiment, the second expression cassette can comprise 1) the heterologous coding sequence encoding the protein operably linked to an isolated nucleic acid having a sequence comprising the sequence of SEQ ID NO:15 or SEQ ID NO:16 wherein SEQ ID NO:15 and SEQ ID NO:16 have promoter activity, or any other known methanol-regulated promoter, such as AOX 1, AOX 2, FLD, or DAS promoter sequences, or 2) the isolated nucleic acid of any one of SEQ ID NOS: 1 to 14, or a fragment thereof, operably linked to the heterologous coding sequence encoding the protein.

In yet another embodiment, the protein can be expressed using the first expression cassette, the second expression cassette, and a third expression cassette. In another illustrative aspect, the third expression cassette can comprise 1) the heterologous coding sequence encoding the protein operably linked to an isolated nucleic acid having a sequence comprising the sequence of SEQ ID NO:15 or SEQ ID NO:16 wherein SEQ ID NO:15 and SEQ ID NO:16 have promoter activity, or any other known methanol-regulated promoters, such as AOX 1, AOX 2, FLD, or DAS promoter sequences, or 2) the isolated nucleic acid of any one of SEQ ID NOS: 1 to 14, or a fragment thereof, operably linked to the heterologous coding sequence encoding the protein.

In another embodiment, any number of additional expression cassettes can be used and the expression cassettes can comprise 1) the heterologous coding sequence encoding the protein operably linked to an isolated nucleic acid having a sequence comprising the sequence of SEQ ID NO:15 or SEQ ID NO:16 wherein SEQ ID NO:15 and SEQ ID NO: have promoter activity, or any other known methanol-regulated promoters, such as AOX 1, AOX 2, FLD, or DAS promoter sequences, or 2) the isolated nucleic acid of any one of SEQ ID NOS: 1 to 14, or a fragment thereof, operably linked to the heterologous coding sequence encoding the protein. In another embodiment, the first expression cassette, the second expression cassette, and the third expression cassette as described above are used in the method, along with a fourth expression cassette, a fifth expression cassette, and a sixth expression cassette wherein all of the expression cassettes comprise the isolated nucleic acid of any one of SEQ ID NOS: 1 to 14, or a fragment thereof, operably linked to the heterologous coding sequence encoding the protein.

In still another embodiment, a method of producing one or more proteins is provided. The method comprises the step of culturing in a culture medium a host cell comprising a first expression cassette, a second expression cassette, and, optionally, one or more additional expression cassettes, wherein each of the expression cassettes comprises 1) a heterologous coding sequence encoding the one or more proteins operably linked to an isolated nucleic acid having a sequence comprising the sequence of SEQ ID NO:15 or SEQ ID NO:16 wherein SEQ ID NO:15 and SEQ ID NO:16 have promoter activity, or any other known methanol-regulated promoters, such as AOX 1, AOX 2, FLD, or DAS promoter sequences, or 2) the isolated nucleic acid of any one of SEQ ID NOS: 1 to 14, or a fragment thereof, operably linked to a heterologous coding sequence encoding the one or more proteins, wherein the culturing is done under conditions permitting expression of the one or more proteins. The method can further comprise the step of purifying one of the one or more proteins from the medium of the cultured host cell.

In any of the embodiments described in the preceding two paragraphs, the isolated nucleic acid can be at least 80%, at least 85%, at least 90%, 92%, 95%, 96%, 97%, 98%, or 99% homologous to the isolated nucleic acid of any of SEQ ID NOS: 1 to 14, or a fragment thereof. In any of the embodiments described in the preceding two paragraphs, the expression cassettes can be included in one expression vector or in multiple expression vectors. In any of the embodiments described in the preceding two paragraphs, the expression vectors into which the expression cassettes are incorporated can be vectors that replicate autonomously or that integrate into the host cell genome.

In various illustrative embodiments, the protein encoded by the any of the heterologous coding sequences described herein operably linked to the promoter can be a protein selected from the group consisting of a toxin, an antibody, a hormone, an enzyme, a growth factor, a cytokine, a structural protein, an immunogenic protein (e.g., a vaccine antigen), and a cell signaling protein. In one embodiment, the protein is an enzyme for use in animal feed. In this embodiment, the protein can be selected from the group consisting of a phytase, a mannanase, a galactosidase, an amylase, a glucanase, a cellulase, a protease, and a xylanase. In another embodiment, the protein can be an enzyme useful for glycosylation. In another aspect, more than one protein can be expressed by using multiple expression cassettes, each with a heterologous coding sequence, operably linked to a promoter. However, these protein examples are non-limiting and any protein, polypeptide, or peptide capable of being expressed in yeast can be expressed in accordance with the isolated nucleic acids, expression vectors, host cells, DNA constructs, methods, and isolated proteins described herein. The enzymes described above can be from any species (e.g., fungal species, such as a yeast species).

The yeast-expressed proteins for use in accordance with the present invention can be produced in purified form by conventional techniques. As used herein, "isolated protein" means a purified protein. A purified protein is substantially free from other yeast cell contaminants or contaminants from the culture medium. For example, "substantially free" from other yeast cell contaminants or contaminants from the culture medium means that the protein is at least about 60% pure, at least about 70% pure, at least about 80% pure, at least about 90% pure, at least about 95% pure, at least about 98% pure, about 60% pure, about 70% pure, about 80% pure, about 90% pure, about 95% pure, or about 98% pure (all based on dry weight). Typically, the protein is secreted into the yeast culture medium and is collected from the culture medium.

In one illustrative embodiment, for purification from the culture medium the protein can, for example, be subjected to ammonium sulfate precipitation followed by DEAE-Sepharose column chromatography. In other embodiments, conventional techniques known to those skilled in the art can be used such as ammonium sulfate or ethanol precipitation, acid extraction, gel filtration, anion or cation exchange chromatography, DEAE-Sepharose column chromatography, hydroxylapatite chromatography, lectin chromatography, affinity chromatography, solvent-solvent extraction, ultrafiltration, and HPLC.

Alternatively, purification steps may not be required because the protein may be present in such high concentrations in the culture medium that the protein is essentially pure in the culture medium (e.g., 70 to 80% pure). In one embodiment, the protein is collected from the culture medium without further purification steps by chilling the yeast culture (e.g., to about 4° C. to about 8° C.) and removing the yeast cells using such techniques as centrifugation, microfiltration, and rotary vacuum filtration. The protein in the cell-free medium can then be concentrated by such techniques as, for example, ultrafiltration and tangential flow filtration.

In some embodiments where the protein is not secreted into the culture medium, the yeast cells can be lysed, for example, by sonication, heat, or chemical treatment, and the homogenate centrifuged to remove cell debris. The supernatant can then be subjected to ammonium sulfate precipitation, and additional fractionation techniques as required, such as gel filtration, ion exchange chromatography, DEAE-Sepharose column chromatography, affinity chromatography, solvent-solvent extraction, ultrafiltration, and HPLC to purify the protein. It should be understood that the purification methods described above for purification of proteins from the culture medium or from lysed yeast cells are non-limiting and any purification techniques known to those skilled in the art can be used to purify the yeast-expressed protein if such techniques are required to obtain a substantially pure protein.

Various formulations of the purified protein preparations may be prepared in accordance with the invention. In some embodiments, the proteins can be stabilized through the addition of other proteins (e.g., gelatin and skim milk powder), chemical agents (e.g., glycerol, polyethylene glycol, EDTA, potassium sorbate, sodium benzoate, and reducing agents and aldehydes), polysaccharides, monosaccharides, lipids (hydrogenated vegetable oils), and the like. In one embodiment, proteins for addition to food products or animal feed blends can be dried (e.g., spray drying, drum drying, and lyophilization) and formulated as powders, granules, pills, mineral blocks, liquids, and gels through known processes. In one embodiment, gelling agents such as gelatin, alginate, collagen, agar, pectin and carrageenan can be used.

In alternate embodiments, the protein expression can be for intracellular expression, such as for enzymatic action in the yeast in a biotransformation process, or for display on the yeast cell surface. For such embodiments, the protein, expressed as described herein, is not purified.

In various embodiments, the proteins described above are selected from the group consisting of a toxin, an antibody, a hormone, an enzyme, a growth factor, a cytokine, a structural protein, an immunogenic protein (e.g., a vaccine antigen), and a cell signaling protein. In another embodiment, the proteins described above are selected from the group consisting of an antibody, a hormone, an enzyme, a growth factor, a cytokine, a structural protein, an immunogenic protein (e.g., a vaccine antigen), and a cell signaling protein. In yet another embodiment the coding sequence for a protein, a fragment thereof, a fusion protein (e.g., a chimeric protein), or a peptide, can be used in accordance with the invention. In another embodiment, a modified protein can be expressed, such as a mutated protein or a protein with non-natural amino acids.

In one embodiment, the toxins can be proteins such as, for example, botulinum toxin or verotoxin-1, and after preparation using the methods, isolated nucleic acids, expression vectors, host cells, and DNA constructs described herein, the toxins can be modified using a targeting agent so that they are directed specifically to diseased cells. In another illustrative aspect, the antibody can be a humanized antibody, an antibody that is not humanized, a nanobody, or an antibody fragment, such as an Fab fragment of an antibody or a single-chain antibody. In another embodiment, the hormone can be, for example, a gonadotropin, an adrenocorticotrophic hormone, a growth hormone, vasopressin, oxytocin, somatostatin, gastrin, or leptin. In another illustrative embodiment, the growth factor can be insulin, epidermal growth factor, fibroblast growth factor, vascular endothelial growth factor, erythropoietin, platelet-derived growth factor, thrombopoietin, or a bone morphogenic protein. In one aspect, the cytokine can be IL-2, IFN-α, IFN-γ, or GM-CSF. In another illustrative aspect, the vaccine proteins can be any suitable vaccine proteins that are immunogenic in a patient or an animal, including, but not limited to, HPV proteins (e.g., HPV 16 and HPV 18), and tetanus vaccine proteins, as examples. In another illustrative embodiment, the enzymes can be, for example, enzymes for animal feeds as discussed herein, acetylcholinesterase, or cyclooxygenase, or any other useful enzyme that can be expressed in yeast. In another embodiment, structural proteins can be expressed, for example, netrins, actin-binding proteins, or myosin, and, in another embodiment, cell signaling proteins such as ras proteins, kinases, the ErbB2 protein (the Her-2 receptor) can be expressed using the methods, isolated nucleic acids, expression vectors, host cells, and DNA constructs described herein.

In one embodiment, the protein is an enzyme for use in animal feed. In this embodiment, the protein can be selected from the group consisting of a phytase, a mannanase, a galactosidase, an amylase, a glucanase, a cellulase, a protease, and a xylanase, or a combination thereof. For example, a variety of phytases may be expressed according to the methods described herein. Exemplary of phytase genes (i.e., a phytase coding sequence) that can be expressed in accordance with the invention are phytase genes derived from bacteria, filamentous fungi, plants, and yeast, such as the appA (Gene Bank accession number M58708) and appA2 (Gene Bank accession number 250016) genes derived from *Escherichia coli* and the phyA and phyB genes derived from the fungus *Aspergillus niger*, or any mutant of these genes that retains or has improved myo-inositol hexakisphosphate phosphohydrolase activity (see, for example, Rodriguez et al., *Arch. of Biochem. and Biophys.* 382: 105-112 (2000), incorporated herein by reference). Substituted, deleted, and truncated phytase genes, or a fragment thereof, can also be expressed in accordance with the invention.

In one embodiment, the protein expressed using the methods described herein can be used in animal feed comprising an animal feed blend. In various embodiments, any animal feed blend known in the art can be used such as rapeseed meal, cottonseed meal, soybean meal, and cornmeal. Optional ingredients of the animal feed blend include sugars and complex carbohydrates such as both water-soluble and water-insoluble monosaccharides, disaccharides and polysaccharides. Optional amino acid ingredients that can be added to the feed blend are arginine, histidine, isoleucine, leucine, lysine, methionine, phenylalanine, threonine, tryptophan, valine, tyrosine ethyl HCl, alanine, aspartic acid, sodium glutamate, glycine, proline, serine, cysteine ethyl HCl, and analogs, and salts thereof. Vitamins that can be optionally added are thiamine HCl, riboflavin, pyridoxine HCl, niacin, niacinamide, inositol, choline chloride, calcium pantothenate, biotin, folic acid, ascorbic acid, and vitamins A, B, K, D, E, and the like. Minerals, protein ingredients, including protein obtained from meat meal or fish meal, liquid or powdered egg, fish solubles, whey protein concentrate, oils (e.g., soybean oil), cornstarch, calcium, inorganic phosphate, copper sulfate, salt, and limestone can also be added. Antioxidants can also be added.

In another embodiment, a kit comprising an expression vector comprising the isolated nucleic acid of SEQ ID NO: 1 to SEQ ID NO: 14, or a fragment thereof, is provided. In one illustrative aspect, the isolated nucleic acid, or the fragment, can be 80%, 85%, 90%, 92%, 95%, 96%, 97%, 98%, or 99% identical to the isolated nucleic acid of SEQ ID NO: 1 to SEQ ID NO: 14, or to the fragment thereof. In various illustrative embodiments, the fragment can be about 50 nucleotides in length, about 100 nucleotides in length, about 200 nucleotides in length, about 300 nucleotides in length, about 400 nucleotides in length, about 500 nucleotides in length, about 600 nucleotides in length, about 700 nucleotides in length, about 800 nucleotides in length, or about 900 nucleotides in length. In other embodiments, the fragment can extend about 50 nucleotides, about 100 nucleotides, about 200 nucleotides, about 300 nucleotides, about 400 nucleotides, about 500 nucleotides, about 600 nucleotides, about 700 nucleotides, about 800 nucleotides, or about 900 nucleotides upstream from the 3' end of the isolated nucleic acid of any of SEQ ID NOS: 1 to 14. In yet other embodiments, the fragment can include about 50 nucleotides, about 100 nucleotides, about 200 nucleotides, about 300 nucleotides, or about 350 nucleotides upstream and/or downstream from the TATA box sequence found in each of SEQ ID NOS: 1 to 14.

In one embodiment, the expression vector (i.e., with the heterologous promoter) included in the kit can have any of the other elements described herein, such as a selection marker, a cloning site, such as a multiple cloning site, an enhancer, a termination sequence, a signal peptide sequence, and the like. In another aspect, the expression vector can be a vector that replicates autonomously or integrates into the host cell genome. In another embodiment, the expression vector can be circularized or linearized (i.e., digested with a restriction enzyme so that a gene of interest can easily be cloned into the expression vector). In another embodiment, the kit can include an expression vector and a control open reading frame encoding a marker or control gene for expression (e.g., an open reading frame encoding a LacZ-α fragment) for use as a control to show that the expression vector is competent to be ligated and to be used with a gene of interest.

In another illustrative embodiment, the kit can contain a tube containing a circular expression plasmid. In another embodiment, the kit can contain a tube with a linear expression vector that is digested with a restriction enzyme so it is ready to clone a gene of interest. In one embodiment, the tube can be sterilized. In either of these embodiments, the kit can also include a circular or linear expression vector and a control open reading frame encoding a marker or control gene for expression (e.g., an open reading frame encoding a LacZ-α fragment) for use as a control in showing that the expression vector can be ligated with a gene of interest, and/or to show that the host cell is competent for transformation.

In yet another embodiment, the kit can contain multiple different expression vectors. In another embodiment, the multiple different expression vectors can contain the same promoter, but different selectable markers, such as genes for resistance to the drugs G418, Nourseothricin (Nat), Zeocin, Blasticidin, or Hygromycin. In this embodiment, the kit may also contain aliquots of the drugs (e.g., G418, Nourseothricin (Nat), Zeocin, Blasticidin, or Hygromycin) in tubes, or other containers, separate from the corresponding vectors.

In any of the kit embodiments described above, the isolated nucleic acid can consist of any one of SEQ ID NOS. 1 to 14, or a fragment thereof. The phrase "consists of" means that the sequence specified by the SEQ ID NO. has no additional nucleotide sequences other than those corresponding to the SEQ ID NO.

In another illustrative aspect, the kit can include other components for use with the expression vector, such as components for transformation of yeast cells, restriction enzymes for incorporating a protein coding sequence of interest into the expression vector, ligases, components for purification of expression vector constructs, buffers (e.g., a ligation buffer), instructions for use (e.g., to facilitate cloning), and any other components suitable for use in a kit for making and using the expression vectors described herein. In another embodiment, the expression vector or any other component of the kit can be included in the kit in a sealed tube (e.g., sterilized or not sterilized) or any other suitable container or package (e.g., sterilized or not sterilized). The kits described in the preceding paragraphs that include the expression vector comprise the expression vector comprising a promoter described herein operably linked to the vector which is heterologous to the promoter (i.e., the combination does not occur in nature).

The following examples provide illustrative methods for carrying out the practice of the present invention. As such, these examples are provided for illustrative purposes only and are not intended to be limiting.

EXAMPLES

Example 1

Promoter Expression Levels

TABLE 1

| Fermentation Samples | | | | | | | |
|---|---|---|---|---|---|---|---|
| Gene | glycerol starvation | 6 hr glycerol feed | 2 hr methanol induction | 6 hr methanol induction | 18 hr methanol induction | 48 hr methanol induction | 66 hr methanol induction |
| AOX1 | 958 | 54 | 21806 | 17607 | 10035 | 581 | 911 |
| AOX2 | 185 | 28 | 10035 | 1374 | 1697 | 64 | 119 |
| CAM1 | 316 | 166 | 13201 | 13201 | 24457 | 36959 | 36959 |
| FLD1 | 3405 | 1293 | 11173 | 10632 | 13473 | 21806 | 14995 |
| GPM2 | 884 | 549 | 7280 | 8614 | 8357 | 14995 | 17607 |
| PP7435_Chr1-1351 | 2102 | 149 | 12171 | 13473 | 14995 | 17607 | 11173 |
| PP7435_Chr1-0269 | 7766 | 8636 | 3252 | 3772 | 6615 | 9483 | 5969 |
| PP7435_Chr2-0207 | 13473 | 17607 | 1520 | 858 | 4496 | 3914 | 3742 |
| PP7435_Chr2-0208 | 21806 | 28506 | 2298 | 1136 | 7155 | 7280 | 8949 |
| PP7435_Chr2-0790 | 2457 | 356 | 7829 | 7502 | 6433 | 2064 | 822 |
| PP7435_Chr2-0809 | 5566 | 4305 | 1668 | 4205 | 4799 | 6758 | 2899 |
| PP7435_Chr3-0476 | 6758 | 9425 | 1648 | 5566 | 6104 | 10632 | 10035 |
| PP7435_Chr3-0842 | 243 | 134 | 8614 | 6987 | 5684 | 7155 | 12171 |
| PP7435_Chr4-0069 | 7502 | 12171 | 1746 | 1162 | 7829 | 9425 | 13473 |
| PP7435_Chr4-0800 | 5064 | 5916 | 2382 | 5415 | 5415 | 6987 | 3964 |
| SPI1 | 275 | 203 | 673 | 376 | 267 | 164 | 195 |
| TDH1 | 8949 | 841 | 2102 | 951 | 2965 | 813 | 104 |
| TEF2 | 7155 | 2248 | 4305 | 7829 | 10632 | 3246 | 757 |
| THI4 | 1668 | 68 | 14995 | 12171 | 2542 | 429 | 419 |

* All numbers as transcripts per million

TABLE 2

| Shake Flask Samples | | | | | |
|---|---|---|---|---|---|
| Gene | strain 1: glycerol shake flask | strain 2: glycerol shake flask | strain 3: glycerol shake flask | strain 4: glycerol shake flask | strain 5: methanol induction |
| AOX1 | 7 | 8 | 24 | 22 | 3167 |
| AOX2 | 12 | 16 | 9 | 8 | 109 |
| CAM1 | 537 | 513 | 661 | 789 | 24110 |
| FLD1 | 762 | 743 | 357 | 1202 | 17607 |
| GPM2 | 303 | 352 | 699 | 561 | 9425 |
| PP7435_Chr1-1351 | 9 | 10 | 15 | 19 | 10035 |
| PP7435_Chr1-0269 | 5587 | 5535 | 11983 | 10362 | 6375 |
| PP7435_Chr2-0207 | 2226 | 2152 | 3466 | 3246 | 680 |
| PP7435_Chr2-0208 | 3167 | 3121 | 7502 | 4402 | 864 |
| PP7435_Chr2-0790 | 41 | 48 | 31 | 26 | 1877 |
| PP7435_Chr2-0809 | 6542 | 6433 | 2965 | 4305 | 6758 |
| PP7435_Chr3-0476 | 28506 | 21806 | 28506 | 28506 | 7829 |
| PP7435_Chr3-0842 | 14 | 16 | 48 | 44 | 1171 |
| PP7435_Chr4-0069 | 4887 | 5684 | 8141 | 9425 | 6542 |
| PP7435_Chr4-0800 | 21806 | 17607 | 10035 | 21806 | 7502 |
| SPI1 | 2500 | 2035 | 4799 | 1529 | 136 |
| TDH1 | 1770 | 5415 | 1177 | 1095 | 2654 |
| TEF2 | 17607 | 28506 | 3914 | 3803 | 12171 |
| THI4 | 10 | 58 | 40 | 30 | 452 |

* All numbers as transcripts per million

Example 2

Strain Growth for RNA Isolation to Examine Promoter Expression Levels

The BG10 strain was maintained as patches on YPD Agar plates. For transcriptome analysis, 50 ml cultures of the strain were inoculated from a patch and grown in BMGY at 30° C. (200 rpm) for approximately 16 hours. The stationary culture was diluted 100-fold into fresh BMGY medium and grown at 30° C. (200 rpm) for 6 hours. This time point was considered exponential growth with glycerol as the carbon source. Aliquots were spun down in 15 ml tubes. Thereafter, supernatants were discarded and the cell pellets were rapidly frozen in liquid nitrogen. Cell pellets were stored at −80° C. for subsequent total RNA isolation.

For RNA-Seq analysis during fermentation, a shake flask culture grown as described above was expanded into a 1-liter fermentor using standard methanol induction conditions. Cell samples were taken at various time points before, during, and at the end of the methanol induction. Cell pellets were collected and frozen in liquid nitrogen. Cell pellets were stored at −80° C. for subsequent total RNA isolation.

Example 3

Total RNA Isolation

FastRNA SPIN kits (MP Bio) were used to isolate total RNA. Cell lysis was performed using a BioSpec Mini-Beadbeater 96. Total RNA was eluted from the spin column in 15 μl of RNase/DNase—free water, frozen in liquid nitrogen and stored at −80° C. RNA samples were shipped on dry ice for RNA-Seq analysis on an Illumina HiSeq machine. RNA samples were analyzed using an Agilent BioAnalyzer, and all showed intact yeast ribosomal RNA peaks.

Example 4

RNA Library Generation and Sequencing mRNA libraries were prepared using Illumina reagents. A TruSeq RNA Sample Preparation Kit was used to selectively generate bar-coded cDNA from polyA RNA. After bar-coding and amplification, a total of 12 samples were pooled (8 fermentation samples, 4 shake flask samples) for analysis. Fifty base, single end reads were performed. Data was supplied to BioGrammatics in standard FASTQ format. Reads were trimmed based on ambiguous bases and quality score and then filtered to eliminate all trimmed reads that were less than 40 bases in length. Approximately 0.3% of reads were removed from each data set.

Example 5

RNA-Seq Analysis

Data sets from an Illumina HiSeq machine were imported into CLC Genomics Workbench (version 6). The standard software tools from CLC Genomics Workbench were used for RNA-Seq analysis. RNA reads were mapped onto a reference *Pichia pastoris* genome. Transcription profiles of 5202 annotated genes were generated across the 12 sample data sets. Based on the transcription profiles, genes with either constitutive or methanol regulated transcription patterns were identified.

Example 6

Protein Expression Analysis

Multiple promoters were inserted into a Promoter Tester Vector, (reporter plasmid, pJ-G-Agal, FIG. 17) to test protein expression. Briefly, an alpha-galactosidase (A-gal) open reading frame (ORF) in the pJ-G-A-gal is used to measure the expression level from a promoter inserted just 5' of the A-gal ORF. Select DNA primers (IDT-DNA, table 3) were used to PCR amplify isolated DNA from *Pichia* genomic DNA (gDNA, BioGrammatics strain wild type *Pichia pastoris* strain Bg10).

TABLE 3

PCR primers for promoters.

| Promoter | SEQ ID NO: | Forward primer | Primer sequence | Primer position on the Promoter sequence |
|---|---|---|---|---|
| SAM | 1 | 11231-F685 | NNNGGTCTCNATCCACGAGTTTCTGGACCGTATC | -685 |
| SAM1 | 1 | 11231-F447 | NNNGGTCTCTATCCGGAAAACGTTAAGAGATG | -447 |
| SAM1 | 1 | 11231-F3 | NNNGGTCTCTATCCCTCTACTAAATTGCCCCAAGTG | -532 |
| Chr1-1351 | 2 | 1351-F1 | NNNGGTCTCNATCCGATGGAGACTCAGTATGATGGGC | -606 |
| Chr1-1351 | 2 | 1351-F2 | NNNGGTCTCNATCCAGTATGATGGGGCAAGGAAAACG | -595 |
| THI4 | 3 | THI4-F1 | NNNGGTCTCNATCCTGGAGACCCTTAACAGGTCG | -404 |
| GPM2 | 4 | GPM2-F1 | NNNGGTCTCNATCCGTTGGGAACTGTGCCCTG | -637 |
| Chr2-0790 | 5 | 790-F1 | NNNGGTCTCNATCCACAGTGGTAGGTCCAACTTGG | -543 |
| Chr3-0842 | 6 | 842-F1 | NNNCGTCTCNATCCGTAGTAGCCTCTCCAGCCTG | -635 |
| Chr1-0269 | 7 | 269-F1 | NNNGGTCTCNATCCTGAAGCCCCTGCAACTACAGAG | -611 |
| Chr2-0207 | 8 | 207-F1 | NNNGGTCTCNATCCGTAGACGACATCCAGAGAAGTAACAG | -632 |
| Chr2-0208 | 9 | 208-F1 | NNNGGTCTCNATCCTCAGGTCAGTCTTGAAGTCCTGAG | -618 |

TABLE 3 -continued

PCR primers for promoters.

| Promoter | SEQ ID NO: | Forward primer | Primer sequence | Primer position on the Promoter sequence |
|---|---|---|---|---|
| Chr2-0809 | 10 | 809-F1 | NNNGGTCTCNATCCTGTGGAATTCCAAAGAAGGGG | -653 |
| Chr4-0069 | 11 | 069-F1 | NNNGGTCTCNATCCGTCCGTGATGTAAAATGAGACTAC | -467 |
| Chr4-0800 | 12 | 800-F1 | NNNGGTCTCNATCCAGTCAACTGGGAGCTACGGT | -490 |
| TEF2 | 13 | TEF2-FF1 | NNNGGTCTCNATCCGATGTGAGGATGCGCTC | -729 |
| Chr3-0476 | 14 | 476-F1 | NNNGGTCTCNATCCTCAATGACCACGGTAACATGAAAAC | -650 |
| GAP |  | GAP-F1 | NNNGGTCTCNATCCAATGGACCAAATTGTTGCAAGGT | -619 |
| DAS |  | 07226F620 | NNNGGTCTCCATCCCTTTGTTGAGCAACA | -382 |
| DAS |  | 07226F518 | NNNGGTCTCGATCCGCCCAAACGAACAG | -483 |
| AOX |  | AOXF1 | NNNGGTCTCCATCCAAAGACGAAAGGTTGAATGA | -931 |

Bg10 gDNA was isolated by breaking the cells by vigorous shaking with 0.5 mm Zirconia/Silica beads (BioSpec Products, Inc.) in the presence of phenol-Chloroform, prior to EtOH precipitation and suspension in a Tris-EDTA solution (10 mM Tris, 1 mM EDTA). PCR was performed for 35 cycles (98° C. for 10 sec, ~55° C. for 10 sec, and 72° C. for ~30 sec) with a proof reading polymerase by standard methods and the manufactures recommendations (New England BioLabs, NEB). After purification of the PCR amplicons (gel isolation and extraction, DNA Clean and Concentrator, Zymo-Research), the restriction enzyme sites strategically placed in the primers were then used to cut and ligate each purified PCR amplicon, independently, into pJ-G-A-gal reporter vector (FIG. 17) by ligation as recommend by the manufacturer (NEB). Standard methods were used to isolate, amplify and purify the each of the resulting pJ-G-A-gal-promoter plasmids. In most cases, the "A" of the reporter start codon is the +1 position relative to the approximately −1, to −1500 base pair position of the reporter (as indicated in table 3) with the primers used to amplify the promoters.

In all cases, the sequence of the promoters in these reporter plasmids was determined using primers 5' and 3' of the insertion site in the vector; sequence was obtained across the entire promoter and the cloning junctions (Genewiz, Inc.), and compared with the respective mRNA sequences to confirm the promoter clone identity. In all cases, the cloning junction between the promoter and the A-gal ORF was designed to position the A-gal ATG start codon, such that is was in the same position as the predicted ATG of the promoters native ORF start codon.

The purified, sequence verified, promoter-reporter constructs were linearized for transformation and integration into the *Pichia* genome of Bg10 *Pichia* cells by electroporation. After restriction enzyme digestion the DNA was cleaned and concentrated to approximately ~200 ng/ul before each construct was independently transformed into electro-competent *Pichia* (Bg10, BioGrammatics, Inc.). The Bg10 cells were made competent by incubation of log phase cells with DTT and subsequent sorbitol washes (*Pichia* Protocols). After electroporation, transformants were selected on YPD with 800 ug/ml G418 and incubated at 30° C. for ~3 days. Cells from isolated colonies were patched to similar YPD-G418 plates, and cells from these patches were used to measure the level of expression from the reporter genes.

Expression of the A-gal ORF, as regulated by the different promoters, was determined measuring the A-gal enzymatic activity. Reporter activity was scored from YPD agar plates made with 100 mM phosphate buffer, pH 6.5, and alpha-X-GAL as a chromogenic substrate. Reporter activity was detected by a blue colored product in, or around, the cells (FIG. 18). Plates 12 and 23 in FIG. 18, panel A, were replica-plated on different carbon sources to plates A and B, respectively, shown in FIG. 18, panels B and C, respectively. Thus, the designations in FIG. 18, panel A of plates 12 and 23 refer to FIG. 18, panels B and C, respectively. The notations of NO:7, NO:8, etc. refer to SEQ ID NOS (i.e., to the promoter used to express α-galactosidase). The level of α-galactosidase expression with the various promoters is noted by 0, +1, +2, +3, +4, and +5 in the eight tables below, with the level of expression increasing from 0 to +5. The tables labeled "12A" correspond to the results shown in FIG. 18, panel B for the various carbon sources. The tables labeled "23B" correspond to the results shown in FIG. 18, panel C for the various carbon sources.

Relative Alpha Galactosidase Expression, Plate 12/A, Glucose

| Promoter (seq ID/name) | FIG. 18 (Panel/row/column) | Carbon Source | Relative A-gal expression (1-5) |
|---|---|---|---|
| No: 7 | A/A/2 | Glucose | 3 |
| No: 7 | A/A/3 | Glucose | 3 |
| No: 7 | A/A/4 | Glucose | 3 |
| No: 7 | A/B/1 | Glucose | 3 |
| No: 8 | A/B/2 | Glucose | 2 |
| No: 8 | A/B/3 | Glucose | 4 |
| No: 8 | A/B/4 | Glucose | 2 |
| No: 8 | A/B/5 | Glucose | 4 |
| Control | A/C/1 | Glucose | 0 |
| No: 8 | A/C/2 | Glucose | 2 |
| No: 5 | A/C/3 | Glucose | 3 |
| No: 10 | A/C/4 | Glucose | 2 |
| No: 10 | A/C/5 | Glucose | 3 |
| No: 10 | A/D/1 | Glucose | 3 |
| No: 14 | A/D/2 | Glucose | 2 |
| No: 14 | A/D/3 | Glucose | 4 |
| No: 14 | A/D/4 | Glucose | 0 |
| No: 14 | A/D/5 | Glucose | 5 |
| Control | A/E/1 | Glucose | 0 |
| Control | A/E/2 | Glucose | 0 |
| No: 12 | A/E/3 | Glucose | 2 |
| No: 12 | A/E/4 | Glucose | 2 |
| No: 12 | A/E/5 | Glucose | 1 |
| 09479 | A/F/1 | Glucose | 3 |
| 09479 | A/F/2 | Glucose | 2 |
| 09479 | A/F/3 | Glucose | 3 |
| No: 13 | A/F/4 | Glucose | 4 |
| UPP-513 | A/F/5 | Glucose | 4 |
| UPP-354 | A/G/1 | Glucose | 4 |
| DAS | A/G/2 | Glucose | 0 |
| 1-0469 | A/G/3 | Glucose | 4 |
| GAP | A/G/4 | Glucose | 3 |
| No: 3 | A/H/1 | Glucose | 2 |
| No: 2 | A/H/2 | Glucose | 0 |
| No: 7 | A/H/3 | Glucose | 0 |
| No: 11 | A/H/4 | Glucose | 3 |

Relative Alpha Galactosidase Expression, Plate 12/A, Glucose

| Promoter (seq ID/name) | FIG. 18 (Panel/row/column) | Carbon Source | Relative A-gal expression (1-5) |
|---|---|---|---|
| No: 11 | A/H/5 | Glucose | 3 |
| No: 3 | A/I/1 | Glucose | 2 |
| No: 3 | A/I/2 | Glucose | 2 |
| No: 3 | A/I/3 | Glucose | 1 |
| No: 3 | A/I/4 | Glucose | 2 |
| No: 3 | A/J/2 | Glucose | 1 |
| No: 3 | A/J/3 | Glucose | 2 |

Relative Alpha Galactosidase Expression, Plate 12/A, Glycerol

| Promoter (seq ID/name) | FIG. 18 (Panel/row/column) | Carbon Source | Relative A-gal expression (1-5) |
|---|---|---|---|
| No: 7 | A/A/2 | Glycerol | 3 |
| No: 7 | A/A/3 | Glycerol | 3 |
| No: 7 | A/A/4 | Glycerol | 3 |
| No: 7 | A/B/1 | Glycerol | 3 |
| No: 8 | A/B/2 | Glycerol | 3 |
| No: 8 | A/B/3 | Glycerol | 4 |
| No: 8 | A/B/4 | Glycerol | 3 |
| No: 8 | A/B/5 | Glycerol | 4 |
| Control | A/C/1 | Glycerol | 0 |
| No: 8 | A/C/2 | Glycerol | 2 |
| No: 5 | A/C/3 | Glycerol | 2 |
| No: 10 | A/C/4 | Glycerol | 2 |
| No: 10 | A/C/5 | Glycerol | 2 |
| No: 10 | A/D/1 | Glycerol | 2 |
| No: 14 | A/D/2 | Glycerol | 2 |
| No: 14 | A/D/3 | Glycerol | 4 |
| No: 14 | A/D/4 | Glycerol | 0 |
| No: 14 | A/D/5 | Glycerol | 5 |
| Control | A/E/1 | Glycerol | 0 |
| Control | A/E/2 | Glycerol | 0 |
| No: 12 | A/E/3 | Glycerol | 2 |
| No: 12 | A/E/4 | Glycerol | 2 |
| No: 12 | A/E/5 | Glycerol | 1 |
| 09479 | A/F/1 | Glycerol | 3 |
| 09479 | A/F/2 | Glycerol | 2 |
| 09479 | A/F/3 | Glycerol | 3 |
| No: 13 | A/F/4 | Glycerol | 3 |
| UPP-513 | A/F/5 | Glycerol | 3 |
| UPP-354 | A/G/1 | Glycerol | 4 |
| DAS | A/G/2 | Glycerol | 0 |
| 1-0469 | A/G/3 | Glycerol | 3 |
| GAP | A/G/4 | Glycerol | 2 |
| No: 3 | A/H/1 | Glycerol | 3 |
| No: 2 | A/H/2 | Glycerol | 0 |
| No: 2 | A/H/3 | Glycerol | 0 |
| No: 11 | A/H/4 | Glycerol | 2 |
| No: 11 | A/H/5 | Glycerol | 3 |
| No: 3 | A/I/1 | Glycerol | 2 |
| No: 3 | A/I/2 | Glycerol | 2 |
| No: 3 | A/I/3 | Glycerol | 1 |
| No: 3 | A/I/4 | Glycerol | 2 |
| No: 3 | A/J/2 | Glycerol | 1 |
| No: 3 | A/J/3 | Glycerol | 2 |

Relative Alpha Galactosidase Expression, Plate 12/A, Methanol plates.

| Promoter (seq ID/name) | FIG. 18 (Panel/row/column) | Carbon Source | Relative A-gal expression (1-5) |
|---|---|---|---|
| No: 7 | A/A/2 | Methanol | 2 |
| No: 7 | A/A/3 | Methanol | 3 |
| No: 7 | A/A/4 | Methanol | 2 |
| No: 7 | A/B/1 | Methanol | 2 |
| No: 8 | A/B/2 | Methanol | 3 |
| No: 8 | A/B/3 | Methanol | 4 |

Relative Alpha Galactosidase Expression, Plate 12/A, Methanol plates.

| Promoter (seq ID/name) | FIG. 18 (Panel/row/column) | Carbon Source | Relative A-gal expression (1-5) |
|---|---|---|---|
| No: 8 | A/B/4 | Methanol | 2 |
| No: 8 | A/B/5 | Methanol | 4 |
| Control | A/C/1 | Methanol | 1 |
| No: 8 | A/C/2 | Methanol | 2 |
| No: 5 | A/C/3 | Methanol | 3 |
| No: 10 | A/C/4 | Methanol | 2 |
| No: 10 | A/C/5 | Methanol | 3 |
| No: 10 | A/D/1 | Methanol | 3 |
| No: 14 | A/D/2 | Methanol | 2 |
| No: 14 | A/D/3 | Methanol | 5 |
| No: 14 | A/D/4 | Methanol | 0 |
| No: 14 | A/D/5 | Methanol | 5 |
| Control | A/E/1 | Methanol | 0 |
| Control | A/E/2 | Methanol | 1 |
| No: 12 | A/E/3 | Methanol | 2 |
| No: 12 | A/E/4 | Methanol | 4 |
| No: 12 | A/E/5 | Methanol | 1 |
| 09479 | A/F/1 | Methanol | 4 |
| 09479 | A/F/2 | Methanol | 2 |
| 09479 | A/F/3 | Methanol | 4 |
| No: 13 | A/F/4 | Methanol | 3 |
| UPP-513 | A/F/5 | Methanol | 3 |
| UPP-354 | A/G/1 | Methanol | 4 |
| DAS | A/G/2 | Methanol | 2 |
| 1-0469 | A/G/3 | Methanol | 3 |
| GAP | A/G/4 | Methanol | 3 |
| No: 3 | A/H/1 | Methanol | 2 |
| No: 2 | A/H/2 | Methanol | 2 |
| No: 2 | A/H/3 | Methanol | 2 |
| No: 11 | A/H/4 | Methanol | 1 |
| No: 11 | A/H/5 | Methanol | 3 |
| No: 3 | A/I/1 | Methanol | 2 |
| No: 3 | A/I/2 | Methanol | 2 |
| No: 3 | A/I/3 | Methanol | 0 |
| No: 3 | A/I/4 | Methanol | 2 |
| No: 3 | A/J/2 | Methanol | 1 |
| No: 3 | A/J/3 | Methanol | 2 |

Relative Alpha Galactosidase Expression, Plate 12-A, Ethanol.

| Promoter (seq ID/name) | FIG. 18 (Panel/row/column) | Carbon Source | Relative A-gal expression (1-5) |
|---|---|---|---|
| No: 7 | A/A/2 | Ethanol | 2 |
| No: 7 | A/A/3 | Ethanol | 2 |
| No: 7 | A/A/4 | Ethanol | 2 |
| No: 7 | A/B/1 | Ethanol | 1 |
| No: 8 | A/B/2 | Ethanol | 0 |
| No: 8 | A/B/3 | Ethanol | 3 |
| No: 8 | A/B/4 | Ethanol | 2 |
| No: 8 | A/B/5 | Ethanol | 4 |
| Control | A/C/1 | Ethanol | 0 |
| No: 8 | A/C/2 | Ethanol | 1 |
| No: 5 | A/C/3 | Ethanol | 2 |
| No: 10 | A/C/4 | Ethanol | 1 |
| No: 10 | A/C/5 | Ethanol | 2 |
| No: 10 | A/D/1 | Ethanol | 2 |
| No: 14 | A/D/2 | Ethanol | 1 |
| No: 14 | A/D/3 | Ethanol | 5 |
| No: 14 | A/D/4 | Ethanol | 0 |
| No: 14 | A/D/5 | Ethanol | 5 |
| Control | A/E/1 | Ethanol | 0 |
| Control | A/E/2 | Ethanol | 0 |
| No: 12 | A/E/3 | Ethanol | 1 |
| No: 12 | A/E/4 | Ethanol | 1 |
| No: 12 | A/E/5 | Ethanol | 0 |
| 09479 | A/F/1 | Ethanol | 3 |
| 09479 | A/F/2 | Ethanol | 2 |
| 09479 | A/F/3 | Ethanol | 3 |
| No: 13 | A/F/4 | Ethanol | 3 |
| UPP-513 | A/F/5 | Ethanol | 3 |
| UPP-354 | A/G/1 | Ethanol | 4 |
| DAS | A/G/2 | Ethanol | 0 |
| 1-0469 | A/G/3 | Ethanol | 3 |
| GAP | A/G/4 | Ethanol | 2 |
| No: 3 | A/H/1 | Ethanol | 2 |
| No: 2 | A/H/2 | Ethanol | 0 |
| No: 2 | A/H/3 | Ethanol | 1 |
| No: 11 | A/H/4 | Ethanol | 2 |
| No: 11 | A/H/5 | Ethanol | 3 |
| No: 3 | A/I/1 | Ethanol | 2 |
| No: 3 | A/I/2 | Ethanol | 1 |
| No: 3 | A/I/3 | Ethanol | 0 |
| No: 3 | A/I/4 | Ethanol | 2 |
| No: 3 | A/J/2 | Ethanol | 1 |
| No: 3 | A/J/3 | Ethanol | 2 |

Relative Alpha Galactosidase Expression, Plate 23/B, Glucose

| Promoter (seq ID/name) | FIG. 18 (Plate B/row/column) | Carbon Source | Relative A-gal expression (1-5) |
|---|---|---|---|
| No: 4 | B/A/1 | Glucose | 0 |
| No: 4 | B/A/2 | Glucose | 0 |
| No: 4 | B/A/3 | Glucose | 0 |
| No: 4 | B/A/4 | Glucose | 0 |
| No: 4 | B/B/1 | Glucose | 0 |
| 11231 | B/B/2 | Glucose | 0 |
| 11231 | B/B/3 | Glucose | 0 |
| No: 1 | B/B/4 | Glucose | 0 |
| No: 1 | B/B/5 | Glucose | 0 |
| No: 1 | B/C/1 | Glucose | 0 |
| No: 14 | B/C/2 | Glucose | 0 |
| No: 14 | B/C/3 | Glucose | 0 |
| No: 14 | B/C/4 | Glucose | 0 |
| No: 14 | B/C/5 | Glucose | 0 |
| No: 14 | B/D/1 | Glucose | 2 |
| No: 14 | B/D/2 | Glucose | 1 |
| No: 2 | B/D/3 | Glucose | 0 |
| No: 2 | B/D/4 | Glucose | 0 |
| No: 2 | B/D/5 | Glucose | 0 |
| No: 2 | B/E/1 | Glucose | 0 |
| No: 2 | B/E/2 | Glucose | 0 |
| No: 2 | B/E/3 | Glucose | 0 |
| No: 2 | B/E/4 | Glucose | 0 |
| No: 2 | B/E/5 | Glucose | 0 |
| UPP-513 | B/F/1 | Glucose | 4 |
| UPP-345 | B/F/2 | Glucose | 4 |
| DAS | B/F/3 | Glucose | 0 |
| 1-0469 | B/F/4 | Glucose | 3 |
| GAP | B/F/5 | Glucose | 4 |
| 09476 | B/G/1 | Glucose | 2 |
| UPP 222 | B/G/2 | Glucose | 3 |
| No: 13 | B/G/3 | Glucose | 4 |
| No: 14 | B/G/4 | Glucose | 4 |
| No: 2 | B/H/1 | Glucose | 0 |
| No: 2 | B/H/2 | Glucose | 0 |
| No: 13 | B/H/3 | Glucose | 4 |
| No: 2 | B/H/4 | Glucose | 0 |
| No: 3 | B/I/2 | Glucose | 0 |
| No: 2 | B/I/3 | Glucose | 0 |
| No: 3 | B/I/4 | Glucose | 0 |
| No: 3 | B/J/3 | Glucose | 0 |

Relative Alpha Galactosidase Expression, Plate 23/B, Glycerol

| Promoter (seq ID/name) | FIG. 18 (Plate B/row/column) | Carbon Source | Relative A-gal expression (1-5) |
|---|---|---|---|
| No: 4 | B/A/1 | Glycerol | 0 |
| No: 4 | B/A/2 | Glycerol | 0 |
| No: 4 | B/A/3 | Glycerol | 0 |
| No: 4 | B/A/4 | Glycerol | 0 |
| No: 4 | B/B/1 | Glycerol | 0 |
| 11231 | B/B/2 | Glycerol | 0 |
| 11231 | B/B/3 | Glycerol | 0 |
| No: 1 | B/B/4 | Glycerol | 0 |
| No: 1 | B/B/5 | Glycerol | 0 |
| No: 1 | B/C/1 | Glycerol | 0 |
| No: 14 | B/C/2 | Glycerol | 0 |
| No: 14 | B/C/3 | Glycerol | 0 |
| No: 14 | B/C/4 | Glycerol | 0 |
| No: 14 | B/C/5 | Glycerol | 0 |
| No: 14 | B/D/1 | Glycerol | 2 |
| No: 14 | B/D/2 | Glycerol | 1 |
| No: 2 | B/D/3 | Glycerol | 0 |
| No: 2 | B/D/4 | Glycerol | 0 |
| No: 2 | B/D/5 | Glycerol | 0 |
| No: 2 | B/E/1 | Glycerol | 0 |
| No: 2 | B/E/2 | Glycerol | 0 |
| No: 2 | B/E/3 | Glycerol | 0 |
| No: 2 | B/E/4 | Glycerol | 0 |
| No: 2 | B/E/5 | Glycerol | 0 |
| UPP-513 | B/F/1 | Glycerol | 4 |
| UPP-345 | B/F/2 | Glycerol | 4 |
| DAS | B/F/3 | Glycerol | 0 |
| 1-0469 | B/F/4 | Glycerol | 3 |
| GAP | B/F/5 | Glycerol | 4 |
| 09476 | B/G/1 | Glycerol | 2 |
| UPP 222 | B/G/2 | Glycerol | 3 |
| No: 13 | B/G/3 | Glycerol | 4 |
| No: 13 | B/G/4 | Glycerol | 4 |
| No: 2 | B/H/1 | Glycerol | 0 |
| No: 2 | B/H/2 | Glycerol | 0 |
| No: 13 | B/H/3 | Glycerol | 4 |
| No: 2 | B/H/4 | Glycerol | 0 |
| No: 3 | B/I/2 | Glycerol | 0 |
| No: 2 | B/I/3 | Glycerol | 0 |
| No: 3 | B/I/4 | Glycerol | 0 |
| No: 3 | B/J/3 | Glycerol | 0 |

Relative Alpha Galactosidase Expression, plate 23-B, Methanol

| Promoter (seq ID/name) | FIG. 18 (Plate/row/column) | Carbon Source | Relative A-gal expression (1-5) |
|---|---|---|---|
| No: 4 | B/A/1 | Methanol | 4 |
| No: 4 | B/A/2 | Methanol | 4 |
| No: 4 | B/A/3 | Methanol | 4 |
| No: 4 | B/A/4 | Methanol | 4 |
| No: 4 | B/B/1 | Methanol | 4 |
| 11231 | B/B/2 | Methanol | 2 |
| 11231 | B/B/3 | Methanol | 3 |
| No: 1 | B/B/4 | Methanol | 4 |
| No: 1 | B/B/5 | Methanol | 5 |
| No: 1 | B/C/1 | Methanol | 4 |
| No: 14 | B/C/2 | Methanol | 3 |
| No: 14 | B/C/3 | Methanol | 2 |
| No: 14 | B/C/4 | Methanol | 1 |
| No: 14 | B/C/5 | Methanol | 0 |
| No: 14 | B/D/1 | Methanol | 2 |
| No: 14 | B/D/2 | Methanol | 1 |
| No: 2 | B/D/3 | Methanol | 3 |
| No: 2 | B/D/4 | Methanol | 3 |
| No: 2 | B/D/5 | Methanol | 3 |
| No: 2 | B/E/1 | Methanol | 4 |
| No: 2 | B/E/2 | Methanol | 2 |
| No: 2 | B/E/3 | Methanol | 3 |
| No: 2 | B/E/4 | Methanol | 3 |
| No: 2 | B/E/5 | Methanol | 3 |
| UPP-513 | B/F/1 | Methanol | 5 |
| UPP-345 | B/F/2 | Methanol | 5 |
| DAS | B/F/3 | Methanol | 3 |
| 1-0469 | B/F/4 | Methanol | 3 |
| GAP | B/F/5 | Methanol | 3 |
| 09476 | B/G/1 | Methanol | 2 |
| UPP 222 | B/G/2 | Methanol | 4 |
| No: 13 | B/G/3 | Methanol | 4 |
| No: 13 | B/G/4 | Methanol | 4 |
| No: 2 | B/H/1 | Methanol | 2 |
| No: 2 | B/H/2 | Methanol | 1 |
| No: 13 | B/H/3 | Methanol | 4 |
| No: 2 | B/H/4 | Methanol | 1 |
| No: 3 | B/I/2 | Methanol | 3 |
| No: 2 | B/I/3 | Methanol | 2 |
| No: 3 | B/I/4 | Methanol | 3 |
| No: 3 | B/J/3 | Methanol | 3 |

Relative Alpha Galactosidase Expression, Plate 23-B, Ethanol

| Promoter (seq ID/name) | FIG. 18 (Plate/row/column) | Carbon Source | Relative A-gal expression (1-5) |
|---|---|---|---|
| No: 4 | B/A/1 | Ethanol | 0 |
| No: 4 | B/A/2 | Ethanol | 0 |
| No: 4 | B/A/3 | Ethanol | 0 |
| No: 4 | B/A/4 | Ethanol | 0 |
| No: 4 | B/B/1 | Ethanol | 0 |
| 11231 | B/B/2 | Ethanol | 0 |
| 11231 | B/B/3 | Ethanol | 0 |
| No: 1 | B/B/4 | Ethanol | 0 |
| No: 1 | B/B/5 | Ethanol | 0 |
| No: 1 | B/C/1 | Ethanol | 0 |
| No: 14 | B/C/2 | Ethanol | 0 |
| No: 14 | B/C/3 | Ethanol | 0 |
| No: 14 | B/C/4 | Ethanol | 0 |
| No: 14 | B/C/5 | Ethanol | 0 |
| No: 14 | B/D/1 | Ethanol | 1 |
| No: 14 | B/D/2 | Ethanol | 0 |
| No: 2 | B/D/3 | Ethanol | 0 |
| No: 2 | B/D/4 | Ethanol | 0 |
| No: 2 | B/D/5 | Ethanol | 0 |
| No: 2 | B/E/1 | Ethanol | 0 |
| No: 2 | B/E/2 | Ethanol | 0 |
| No: 2 | B/E/3 | Ethanol | 0 |
| No: 2 | B/E/4 | Ethanol | 0 |
| No: 2 | B/E/5 | Ethanol | 0 |
| UPP-513 | B/F/1 | Ethanol | 4 |
| UPP-345 | B/F/2 | Ethanol | 4 |
| DAS | B/F/3 | Ethanol | 0 |
| 1-0469 | B/F/4 | Ethanol | 3 |
| GAP | B/F/5 | Ethanol | 4 |
| 09476 | B/G/1 | Ethanol | 2 |
| UPP 222 | B/G/2 | Ethanol | 3 |
| No: 13 | B/G/3 | Ethanol | 4 |
| No: 13 | B/G/4 | Ethanol | 4 |
| No: 2 | B/H/1 | Ethanol | 0 |
| No: 2 | B/H/2 | Ethanol | 0 |
| No: 13 | B/H/3 | Ethanol | 4 |
| No: 2 | B/H/4 | Ethanol | 0 |
| No: 3 | B/I/2 | Ethanol | 0 |
| No: 2 | B/I/3 | Ethanol | 0 |
| No: 3 | B/I/4 | Ethanol | 0 |
| No: 3 | B/J/3 | Ethanol | 0 |

What is claimed is:

1. A method of producing a protein, the method comprising the step of culturing in a culture medium a host cell comprising a first expression cassette comprising a first isolated nucleic acid at least 95% identical to a nucleic acid selected from the group consisting of SEQ ID NO: 1, SEQ ID NO: 3, SEQ ID NO: 5, SEQ ID NO: 6 and a fragment of SEQ ID NO: 1, SEQ ID NO: 3, SEQ ID NO: 5 or SEQ ID NO: 6, operably linked to a heterologous coding sequence encoding a protein, wherein the first isolated nucleic acid comprises the sequence of a methanol inducible *Pichia pastoris* promoter, wherein the fragment extends about 300 nucleotides, about 400 nucleotides, about 500 nucleotides, about 600 nucleotides, or about 700 nucleotides upstream from the 3' end of SEQ ID NO: 1, SEQ ID NO: 3, SEQ ID NO: 5, or SEQ ID NO: 6, wherein the fragment is a continuous fragment of SEQ ID NO: 1, SEQ ID NO: 3, SEQ ID NO: 5, or SEQ ID NO: 6, wherein the fragment comprises a TATA box sequence to direct initiation of transcription, wherein the culturing is done under conditions permitting expression of the protein, and wherein the protein is expressed using the first expression cassette in combination with a second expression cassette, said second cassette comprising
- (a) the heterologous coding sequence encoding the protein operably linked to a second isolated nucleic acid at least 95% identical to a sequence comprising SEQ ID NO: 2 or SEQ ID NO: 4, wherein SEQ ID NO: 2 or SEQ ID NO: 4 have promoter activity; or
- (b) the heterologous coding sequence encoding the protein operably linked to a second isolated nucleic acid at least 95% identical to a sequence comprising SEQ ID NO: 15 or SEQ ID NO: 16, wherein SEQ ID NO: 15 or SEQ ID NO: 16 have promoter activity; or
- (c) the heterologous coding sequence encoding the protein operably linked to a different AOX promoter than SEQ ID NO: 15 or SEQ ID NO: 16, an FLD promoter DAS promoter.

2. The method of claim 1 wherein the first isolated nucleic acid in the first expression cassette is at least 98% identical to a nucleic acid selected from the group consisting of SEQ ID NO: 1, SEQ ID NO: 3, SEQ ID NO: 5, and SEQ ID NO: 6, or at least 98% identical to the fragment thereof.

3. The method of claim 1 wherein the sequence of the first isolated nucleic acid in the first expression cassette is a nucleic acid selected from the group consisting of SEQ ID NO: 1, SEQ ID NO: 3, SEQ ID NO: 5, and SEQ ID NO: 6, or the fragment thereof.

4. The method of claim 1 wherein the sequence of the first isolated nucleic acid in the first expression cassette is a nucleic acid selected from the group consisting of SEQ ID NO: 1, SEQ ID NO: 3, SEQ ID NO: 5, and SEQ ID NO: 6.

5. The method of claim 1 wherein the heterologous coding sequence encodes a protein selected from the group consisting of a toxin, an antibody, a hormone, an enzyme, a growth factor, a cytokine, a structural protein, an immunogenic protein, and a cell signaling protein.

6. The method of claim 1 wherein the heterologous coding sequence encodes an enzyme for use in animal feed.

7. The method of claim 6 wherein the enzyme is selected from the group consisting of a mannanase, an amylase, a glucanase, a protease, a cellulase, and a xylanase.

8. The method of claim 6 wherein the enzyme is a phytase.

9. The method of claim 6 wherein the enzyme is a galactosidase.

10. The method of claim 1 wherein said second expression cassette comprises
- (a) the heterologous coding sequence encoding the protein operably linked to said second isolated nucleic acid having a sequence comprising SEQ ID NO: 2 or SEQ ID NO: 4, wherein SEQ ID NO: 2 or SEQ ID NO: 4 have promoter activity; or
- (b) the heterologous coding sequence encoding the protein operably linked to said second isolated nucleic acid having a sequence comprising SEQ ID NO: 15 or SEQ ID NO: 16, wherein SEQ ID NO: 15 or SEQ ID NO: 16 have promoter activity.

11. The method of claim 1 wherein said first isolated nucleic acid is at least 95% identical to a nucleic acid of SEQ ID NO: 1, or said fragment thereof; and
said second isolated nucleic acid is at least 95% identical to a nucleic acid of SEQ ID NO: 15.

12. A host cell comprising a first expression cassette comprising an first isolated nucleic acid at least 95% identical to a nucleic acid selected from the group consisting of SEQ ID NO: 1, SEQ ID NO: 3, SEQ ID NO: 5, and SEQ ID NO: 6 and a fragment of SEQ ID NO: 1, SEQ ID NO: 3, SEQ ID NO: 5 or SEQ ID NO: 6, operably linked to a heterologous coding sequence encoding a protein, wherein the first isolated nucleic acid comprises the sequence of a methanol inducible *Pichia pastoris* promoter, wherein the fragment extends about 300 nucleotides, about 400 nucleotides, about 500 nucleotides, about 600 nucleotides, or about 700 nucleotides upstream from the 3' end of SEQ ID NO: 1, SEQ ID NO: 3, SEQ ID NO: 5, or SEQ ID NO: 6, wherein the fragment is a continuous fragment of SEQ ID NO: 1, SEQ ID NO: 3, SEQ ID NO: 5, or SEQ ID NO: 6, wherein the fragment comprises a TATA box sequence to direct initiation of transcription, and a second expression cassette, said second cassette comprising
- (a) the heterologous coding sequence encoding the protein operably linked to a second isolated nucleic acid having a sequence comprising SEQ ID NO: 2 or SEQ ID NO: 4, wherein SEQ ID NO: 2 or SEQ ID NO: 4 have promoter activity; or
- (b) the heterologous coding sequence encoding the protein operably linked to a second isolated nucleic acid having a sequence comprising SEQ ID NO: 15 or SEQ ID NO: 16, wherein SEQ ID NO: 15 or SEQ ID NO: 16 have promoter activity; or
- (c) the heterologous coding sequence encoding the protein operably linked to a different AOX promoter than SEQ ID NO: 15 or SEQ ID NO: 16, an FLD promoter.

13. The host cell of claim 12 wherein the first isolated nucleic acid in the first expression cassette is at least 98% identical to SEQ ID NO: 1, SEQ ID NO: 3, SEQ ID NO: 5, or SEQ ID NO: 6, or at least 98% identical to the fragment thereof.

14. The host cell of claim 12 wherein the sequence of the first isolated nucleic acid in the first expression cassette is SEQ ID NO: 1, SEQ ID NO: 3, SEQ ID NO: 5, or SEQ ID NO: 6, or the fragment thereof.

15. The host cell of claim 12 wherein the sequence of the first isolated nucleic acid in the first expression cassette is SEQ ID NO: 1, SEQ ID NO: 3, SEQ ID NO: 5, or SEQ ID NO: 6.

16. The host cell of claim 12 wherein the heterologous coding sequence encodes a protein selected from the group consisting of a toxin, an antibody, a hormone, an enzyme, a growth factor, a cytokine, a structural protein, an immunogenic protein, and a cell signaling protein.

17. The host cell of claim 12 wherein the heterologous coding sequence encodes an enzyme for use in animal feed.

18. The host cell of claim 17 wherein the enzyme is selected from the group consisting of a mannanase, an amylase, a glucanase, a protease, a cellulase, and a xylanase.

19. The host cell of claim 17 wherein the enzyme is a phytase.

20. The host cell of claim 17 wherein the enzyme is a galactosidase.

* * * * *